United States Patent
Houde et al.

(10) Patent No.: US 11,369,739 B2
(45) Date of Patent: *Jun. 28, 2022

(54) METHOD TO PROVIDE INJECTION SYSTEM PARAMETERS FOR INJECTING FLUID INTO PATIENT

(71) Applicant: Medline Industries, LP, Northfield, IL (US)

(72) Inventors: Eric Houde, Queensbury, NY (US); Kirsten Cleveland, South Glens Fall, NY (US)

(73) Assignee: Medline Industries, LP, Northfield, IL (US)

( * ) Notice: Subject to any disclaimer, the term of this patent is extended or adjusted under 35 U.S.C. 154(b) by 850 days.

This patent is subject to a terminal disclaimer.

(21) Appl. No.: 14/159,777

(22) Filed: Jan. 21, 2014

(65) Prior Publication Data

US 2014/0208251 A1    Jul. 24, 2014

Related U.S. Application Data

(63) Continuation-in-part of application No. PCT/US2013/061397, filed on Sep. 24, 2013.

(Continued)

(51) Int. Cl.
*A61M 5/168* (2006.01)
*A61M 5/00* (2006.01)
(Continued)

(52) U.S. Cl.
CPC ........ *A61M 5/16827* (2013.01); *A61M 5/007* (2013.01); *A61M 5/1408* (2013.01);
(Continued)

(58) Field of Classification Search
CPC ...... A61M 5/007; A61M 5/20; A61M 5/1408; A61M 2205/505; A61M 5/16827;
(Continued)

(56) References Cited

U.S. PATENT DOCUMENTS 264,911 A    9/1882 Vines
315,720 A    4/1885 Campbell
(Continued)

FOREIGN PATENT DOCUMENTS

AU    2007273087    1/2008
AU    2009319936    6/2010
(Continued)

OTHER PUBLICATIONS

Herts et al., Power Injection of Contrast Media Using Central Venous Catheters: Feasibility, Safety and Efficacy, American Journal of Roentgenology, vol. 176, Feb. 2001.
(Continued)

*Primary Examiner* — Tadesse Hailu
*Assistant Examiner* — Alvaro R Calderon, IV
(74) *Attorney, Agent, or Firm* — Fitch, Even, Tabin & Flannery LLP

(57) ABSTRACT

Automated injection system disclosed in this application advantageously provides physicians with a simplified interface for selecting fluid sources, such as saline, contrast, or a mixture of both, to inject at high pressures. The injector system may comprise a multi-use subassembly, a single-use subassembly, a fitting to fluidly connect the multi-use and single-use subassemblies, a hand held controller, a user interface, and an injector housing.

11 Claims, 57 Drawing Sheets

Related U.S. Application Data

(60) Provisional application No. 61/754,687, filed on Jan. 21, 2013.

(51) Int. Cl.
*A61M 5/20* (2006.01)
*A61M 5/145* (2006.01)
*A61M 5/14* (2006.01)
*A61M 5/172* (2006.01)
*A61M 5/315* (2006.01)
*A61M 39/00* (2006.01)

(52) U.S. Cl.
CPC ........ *A61M 5/14546* (2013.01); *A61M 5/172* (2013.01); *A61M 5/20* (2013.01); *A61M 5/2066* (2013.01); *A61M 5/31546* (2013.01); *A61M 2039/0027* (2013.01); *A61M 2205/505* (2013.01)

(58) Field of Classification Search
CPC ..... A61M 5/172; A61M 5/14546; A61B 5/02; G06F 19/3406; G06F 19/34; G06F 19/3418
See application file for complete search history.

(56) References Cited

U.S. PATENT DOCUMENTS

| | | |
|---|---|---|
| 317,770 A | 5/1885 | Hardy |
| 320,717 A | 6/1885 | Stanley |
| 338,437 A | 3/1886 | Carruthers |
| 370,134 A | 9/1887 | Flick |
| 2,649,115 A | 8/1953 | Deardorff |
| 3,157,201 A | 11/1964 | Littmann |
| 3,177,707 A | 4/1965 | Tetsios |
| 3,207,179 A | 9/1965 | Robert |
| 3,384,372 A | 5/1968 | Dickens |
| 3,674,009 A | 7/1972 | Williamson |
| 3,701,345 A | 10/1972 | Heilman |
| 3,749,285 A | 7/1973 | Latham, Jr. |
| 3,774,604 A | 11/1973 | Danielsson |
| 3,812,843 A | 5/1974 | Wootten et al. |
| 3,834,372 A | 9/1974 | Turney |
| 3,939,832 A | 2/1976 | Miller |
| 3,957,082 A * | 5/1976 | Fuson ................ A61M 5/1408 128/DIG. 26 |
| 4,006,736 A | 2/1977 | Kranys et al. |
| 4,024,864 A | 5/1977 | Davies et al. |
| 4,059,017 A | 11/1977 | Settlemyer et al. |
| 4,072,292 A | 2/1978 | Banon |
| 4,084,606 A | 4/1978 | Mittleman |
| 4,085,749 A | 4/1978 | Chambron |
| 4,204,535 A | 5/1980 | Pohlmann |
| 4,250,887 A | 2/1981 | Dardik et al. |
| 4,342,315 A | 8/1982 | Jackson |
| 4,370,982 A | 2/1983 | Reilly |
| 4,430,074 A | 2/1984 | Mooring |
| 4,435,171 A | 3/1984 | Goldberg et al. |
| 4,447,230 A | 5/1984 | Gula et al. |
| 4,447,236 A | 5/1984 | Quinn |
| 4,502,488 A | 3/1985 | Degironimo et al. |
| 4,512,764 A | 4/1985 | Wunsch |
| 4,533,346 A | 8/1985 | Cosgrove, Jr. et al. |
| 4,540,027 A | 9/1985 | Forberg |
| 4,551,133 A | 11/1985 | Zegers de Beyl et al. |
| 4,559,036 A | 12/1985 | Wunsch |
| 4,604,090 A | 8/1986 | Reinicke |
| 4,604,093 A | 8/1986 | Brown et al. |
| 4,620,846 A | 11/1986 | Goldberg et al. |
| 4,621,647 A | 11/1986 | Loveland |
| 4,634,431 A | 1/1987 | Whitney et al. |
| 4,648,870 A | 3/1987 | Goldberg et al. |
| 4,653,539 A | 3/1987 | Bell |
| 4,666,429 A | 5/1987 | Stone |
| 4,669,465 A | 6/1987 | Moore et al. |
| 4,677,980 A | 7/1987 | Reilly |
| 4,690,165 A | 9/1987 | Leytes et al. |
| 4,695,271 A | 9/1987 | Goethel |
| 4,699,615 A | 10/1987 | Fischell et al. |
| 4,705,501 A | 11/1987 | Wigness et al. |
| 4,767,406 A | 8/1988 | Wadham et al. |
| 4,769,017 A | 9/1988 | Fath et al. |
| 4,789,000 A | 12/1988 | Aslanian |
| 4,790,193 A | 12/1988 | Moriuchi et al. |
| 4,812,724 A | 3/1989 | Langer et al. |
| 4,813,927 A | 3/1989 | Morris et al. |
| 4,819,653 A | 4/1989 | Marks |
| 4,819,684 A | 4/1989 | Zaugg et al. |
| 4,838,269 A | 6/1989 | Robinson et al. |
| 4,846,806 A | 7/1989 | Wigness et al. |
| 4,854,324 A | 8/1989 | Hirschman et al. |
| 4,861,340 A | 8/1989 | Smith et al. |
| 4,871,353 A | 10/1989 | Thomsen |
| 4,877,956 A | 10/1989 | Priest |
| 4,892,524 A | 1/1990 | Smith |
| 4,908,018 A | 3/1990 | Thomsen |
| 4,915,688 A | 4/1990 | Bischof et al. |
| 4,919,650 A | 4/1990 | Feingold et al. |
| 4,927,411 A | 5/1990 | Pastrone et al. |
| 4,934,375 A | 6/1990 | Cole et al. |
| 4,936,542 A | 6/1990 | Beard |
| 4,952,205 A | 8/1990 | Mauerer et al. |
| 5,014,715 A | 5/1991 | Chapolini |
| 5,020,562 A | 6/1991 | Richmond et al. |
| 5,034,004 A | 7/1991 | Crankshaw |
| 5,053,002 A | 10/1991 | Barlow |
| 5,057,120 A | 10/1991 | Farcot |
| 5,074,334 A | 12/1991 | Onodera |
| 5,084,031 A | 1/1992 | Todd et al. |
| 5,104,387 A | 4/1992 | Pokorney et al. |
| 5,105,820 A | 4/1992 | Moriuchi et al. |
| 5,112,301 A | 5/1992 | Fenton et al. |
| 5,114,423 A | 5/1992 | Kasprzyk et al. |
| 5,127,904 A | 7/1992 | Loo et al. |
| 5,129,887 A | 7/1992 | Euteneuer et al. |
| 5,134,079 A | 7/1992 | Cusack et al. |
| 5,135,026 A | 8/1992 | Manska |
| 5,135,502 A | 8/1992 | Koenig et al. |
| 5,137,514 A | 8/1992 | Ryan |
| 5,139,484 A | 8/1992 | Hazon et al. |
| 5,148,811 A | 9/1992 | Messinger |
| 5,163,902 A | 11/1992 | Lynn et al. |
| 5,163,904 A | 11/1992 | Lampropoulos et al. |
| 5,168,901 A | 12/1992 | Marks |
| 5,171,216 A | 12/1992 | Dasse et al. |
| 5,171,230 A | 12/1992 | Eland et al. |
| 5,190,067 A | 3/1993 | Paradis et al. |
| 5,190,525 A | 3/1993 | Oswald et al. |
| 5,207,642 A | 5/1993 | Orkin et al. |
| 5,217,432 A | 6/1993 | Rudzena et al. |
| 5,232,024 A | 8/1993 | Williams |
| 5,232,449 A | 8/1993 | Stern et al. |
| 5,236,416 A | 8/1993 | McDaniel et al. |
| 5,236,417 A | 8/1993 | Wallis |
| 5,238,026 A | 8/1993 | Goto |
| 5,246,011 A | 9/1993 | Caillouette |
| 5,254,092 A | 10/1993 | Polyak |
| 5,288,290 A | 2/1994 | Brody |
| 5,290,263 A | 3/1994 | Wigness et al. |
| 5,300,029 A | 4/1994 | Denance |
| 5,322,511 A | 6/1994 | Armbruster et al. |
| 5,324,274 A | 6/1994 | Martin |
| 5,328,463 A | 7/1994 | Barton et al. |
| 5,333,607 A | 8/1994 | Kee et al. |
| 5,334,170 A | 8/1994 | Moroski |
| 5,354,284 A | 10/1994 | Haber et al. |
| 5,356,375 A | 10/1994 | Higley |
| 5,357,946 A | 10/1994 | Kee et al. |
| 5,378,229 A | 1/1995 | Layer et al. |
| 5,380,665 A | 1/1995 | Cusack et al. |
| 5,399,172 A | 3/1995 | Martin et al. |
| 5,407,424 A | 4/1995 | Lafontaine et al. |
| 5,417,689 A | 5/1995 | Fine |

(56) References Cited

U.S. PATENT DOCUMENTS

| | | |
|---|---|---|
| 5,423,751 A | 6/1995 | Harrison et al. |
| 5,431,185 A | 7/1995 | Shannon et al. |
| 5,443,450 A | 8/1995 | Kratoska et al. |
| 5,445,141 A | 8/1995 | Kee et al. |
| 5,445,616 A | 8/1995 | Kratoska et al. |
| 5,451,208 A | 9/1995 | Goldrath |
| 5,454,792 A | 10/1995 | Tennican et al. |
| 5,466,227 A | 11/1995 | Kessenich |
| 5,485,831 A | 1/1996 | Holdsworth et al. |
| 5,490,837 A | 2/1996 | Blaeser et al. |
| 5,496,273 A | 3/1996 | Pastrone et al. |
| 5,496,311 A | 3/1996 | Abele et al. |
| 5,501,674 A | 3/1996 | Trombley et al. |
| 5,515,851 A | 5/1996 | Goldstein |
| 5,520,666 A | 5/1996 | Choudhury et al. |
| 5,533,978 A | 7/1996 | Teirstein |
| 5,536,247 A | 7/1996 | Thornton |
| 5,545,141 A | 8/1996 | Eld |
| 5,551,849 A | 9/1996 | Christiansen |
| 5,562,614 A | 10/1996 | O'Donnell |
| 5,569,208 A | 10/1996 | Woelpper et al. |
| 5,573,515 A | 11/1996 | Wilson et al. |
| 5,575,767 A | 11/1996 | Stevens |
| 5,575,779 A | 11/1996 | Barry |
| 5,578,059 A | 11/1996 | Patzer |
| 5,586,579 A | 12/1996 | Diehl |
| 5,593,385 A | 1/1997 | Harrison et al. |
| 5,601,651 A * | 2/1997 | Watabe ............... C23C 16/455 118/715 |
| 5,611,340 A | 3/1997 | Souza et al. |
| 5,611,784 A | 3/1997 | Barresi et al. |
| 5,618,268 A | 4/1997 | Raines et al. |
| 5,628,306 A | 5/1997 | Kee |
| 5,640,995 A | 6/1997 | Packard et al. |
| 5,662,612 A | 9/1997 | Niehoff |
| 5,665,074 A | 9/1997 | Kelly |
| 5,681,339 A | 10/1997 | McEwen et al. |
| 5,697,899 A | 12/1997 | Hillman et al. |
| 5,697,904 A | 12/1997 | Raines et al. |
| 5,730,731 A | 3/1998 | Mollenauer et al. |
| 5,733,259 A | 3/1998 | Valcke et al. |
| 5,738,662 A | 4/1998 | Shannon et al. |
| 5,739,508 A * | 4/1998 | Uber, III ............... A61M 5/172 235/375 |
| 5,743,872 A | 4/1998 | Kelly |
| 5,752,918 A | 5/1998 | Fowler et al. |
| 5,779,666 A | 7/1998 | Teirstein |
| 5,788,215 A | 8/1998 | Ryan |
| 5,792,102 A | 8/1998 | Mueller-Spaeth |
| 5,800,383 A | 9/1998 | Chandler et al. |
| 5,800,397 A | 9/1998 | Wilson et al. |
| 5,800,408 A | 9/1998 | Strauss et al. |
| 5,806,519 A | 9/1998 | Evans et al. |
| 5,827,219 A | 10/1998 | Uber et al. |
| 5,830,180 A | 11/1998 | Chandler et al. |
| 5,830,194 A | 11/1998 | Anwar et al. |
| 5,833,706 A | 11/1998 | St Germain |
| 5,840,026 A * | 11/1998 | Uber, III ............... A61B 8/06 600/431 |
| 5,842,468 A | 12/1998 | Denyer et al. |
| 5,843,051 A | 12/1998 | Adams et al. |
| D404,717 S | 1/1999 | Duchon et al. |
| 5,860,938 A | 1/1999 | Lafontaine et al. |
| 5,865,805 A | 2/1999 | Ziemba |
| 5,868,710 A | 2/1999 | Battiato et al. |
| 5,879,627 A | 3/1999 | Tanihata |
| 5,882,343 A | 3/1999 | Wilson et al. |
| 5,882,348 A | 3/1999 | Winterton et al. |
| 5,885,216 A | 3/1999 | Evans et al. |
| 5,894,093 A | 4/1999 | Ferguson et al. |
| 5,911,708 A | 6/1999 | Teirstein |
| 5,913,844 A | 6/1999 | Ziemba et al. |
| 5,916,165 A | 6/1999 | Duchon et al. |
| 5,925,016 A | 7/1999 | Chornenky et al. |
| 5,925,022 A | 7/1999 | Battiato et al. |
| 5,928,197 A | 7/1999 | Niehoff |
| 5,934,888 A | 8/1999 | Marka et al. |
| 5,964,714 A | 10/1999 | Lafontaine |
| 5,976,112 A | 11/1999 | Lyza |
| 5,988,587 A | 11/1999 | Duchon et al. |
| 5,993,779 A | 11/1999 | Mori |
| 6,001,112 A | 12/1999 | Taylor |
| 6,017,318 A | 1/2000 | Gauthier et al. |
| 6,030,368 A | 2/2000 | Anwar et al. |
| 6,063,052 A | 5/2000 | Uber et al. |
| 6,083,205 A | 7/2000 | Bourne et al. |
| 6,099,502 A | 8/2000 | Duchon et al. |
| 6,099,511 A | 8/2000 | Devos et al. |
| 6,110,144 A | 8/2000 | Choh et al. |
| 6,117,102 A | 9/2000 | Schwartz et al. |
| 6,135,153 A | 10/2000 | Cleland et al. |
| 6,139,570 A | 10/2000 | Saadat et al. |
| 6,139,571 A | 10/2000 | Fuller et al. |
| 6,146,360 A | 11/2000 | Rogers et al. |
| 6,158,467 A | 12/2000 | Loo |
| 6,171,276 B1 | 1/2001 | Lippe et al. |
| 6,176,843 B1 | 1/2001 | Dicaprio et al. |
| 6,209,568 B1 | 4/2001 | Guarneri |
| 6,221,045 B1 | 4/2001 | Duchon et al. |
| 6,238,372 B1 | 5/2001 | Zinger et al. |
| 6,242,472 B1 | 6/2001 | Sekins et al. |
| 6,295,990 B1 | 10/2001 | Lewis et al. |
| 6,315,762 B1 | 11/2001 | Recinella et al. |
| 6,325,777 B1 | 12/2001 | Zadno-Azizi et al. |
| 6,325,778 B1 | 12/2001 | Zadno-Azizi et al. |
| 6,344,030 B1 | 2/2002 | Duchon et al. |
| 6,355,014 B1 | 3/2002 | Zadno-Azizi et al. |
| 6,361,528 B1 | 3/2002 | Wilson et al. |
| 6,371,942 B1 | 4/2002 | Schwartz et al. |
| 6,397,098 B1 * | 5/2002 | Uber, III ............... A61B 6/481 600/431 |
| 6,416,496 B1 | 7/2002 | Rogers et al. |
| 6,447,481 B1 | 9/2002 | Duchon et al. |
| 6,454,779 B1 | 9/2002 | Taylor |
| 6,457,488 B2 | 10/2002 | Loo |
| 6,471,674 B1 | 10/2002 | Emig |
| 6,488,659 B1 | 12/2002 | Rosenman |
| 6,520,937 B2 | 2/2003 | Hart et al. |
| 6,537,268 B1 | 3/2003 | Gibson et al. |
| RE38,074 E | 4/2003 | Recinella et al. |
| 6,544,232 B1 | 4/2003 | McDaniel |
| 6,866,654 B2 | 3/2005 | Callan et al. |
| 7,094,216 B2 | 8/2006 | Trombley et al. |
| 7,172,572 B2 | 2/2007 | Diamond et al. |
| 7,267,667 B2 | 9/2007 | Houde |
| 7,326,186 B2 | 2/2008 | Trombley, III |
| 7,975,922 B2 | 7/2011 | Fago |
| 8,082,018 B2 | 12/2011 | Duchon et al. |
| 8,192,397 B2 | 6/2012 | Griffiths |
| 8,197,466 B2 | 6/2012 | Yokota |
| 8,992,489 B2 * | 3/2015 | Spohn ............... A61M 5/007 137/460 |
| 9,011,377 B2 | 4/2015 | Schriver et al. |
| 9,101,708 B2 | 8/2015 | Small et al. |
| 9,192,711 B2 | 11/2015 | Barnes |
| 9,220,834 B2 | 12/2015 | Vilks |
| 9,238,099 B2 | 1/2016 | Kalafut et al. |
| 9,259,526 B2 | 2/2016 | Barron et al. |
| 9,302,044 B2 | 4/2016 | Kalafut et al. |
| 9,336,352 B2 | 5/2016 | Humeniuk |
| 9,352,105 B2 | 5/2016 | Hieb et al. |
| 9,364,634 B2 | 6/2016 | Adams et al. |
| 9,398,894 B2 | 7/2016 | Patrick et al. |
| 9,399,112 B2 | 7/2016 | Shevgoor et al. |
| 9,421,330 B2 | 8/2016 | Kalafut et al. |
| 9,433,730 B2 * | 9/2016 | Schriver ........... A61M 5/16827 |
| 9,457,140 B2 | 10/2016 | Barron et al. |
| 9,554,826 B2 | 1/2017 | Lee-Sepsick et al. |
| 9,566,381 B2 | 2/2017 | Barron et al. |
| 9,861,742 B2 * | 1/2018 | Schriver ........... A61M 5/16827 |
| 9,949,704 B2 * | 4/2018 | Kalafut ............... A61B 6/481 |
| 10,279,112 B2 * | 5/2019 | Houde ............... A61M 5/1452 |
| 2001/0044618 A1 | 11/2001 | Recinella et al. |
| 2002/0022807 A1 | 2/2002 | Duchon et al. |

(56) References Cited

U.S. PATENT DOCUMENTS

| | | | |
|---|---|---|---|
| 2002/0038105 A1 | 3/2002 | Schwartz et al. | |
| 2002/0065467 A1* | 5/2002 | Schutt | A61B 5/055 600/454 |
| 2002/0095117 A1 | 7/2002 | Wilson et al. | |
| 2002/0123716 A1* | 9/2002 | VanDiver | A61M 5/1452 604/65 |
| 2002/0143294 A1 | 10/2002 | Duchon et al. | |
| 2002/0151854 A1 | 10/2002 | Duchon et al. | |
| 2002/0183616 A1 | 12/2002 | Toews et al. | |
| 2002/0198496 A1* | 12/2002 | Duchon | A61B 6/481 604/154 |
| 2003/0018252 A1* | 1/2003 | Duchon | A61B 6/481 600/432 |
| 2003/0028145 A1* | 2/2003 | Duchon | A61B 6/481 604/151 |
| 2003/0052787 A1* | 3/2003 | Zerhusen | G06Q 30/04 340/573.1 |
| 2003/0125618 A1* | 7/2003 | Houde | A61M 5/007 600/431 |
| 2003/0125673 A1* | 7/2003 | Houde | F16K 11/0856 604/246 |
| 2004/0010229 A1* | 1/2004 | Houde | A61M 5/007 604/151 |
| 2004/0064041 A1* | 4/2004 | Lazzaro | A61M 5/14546 600/432 |
| 2004/0082904 A1* | 4/2004 | Houde | A61M 39/223 604/33 |
| 2004/0143212 A1 | 7/2004 | Trombley, III et al. | |
| 2004/0143225 A1 | 7/2004 | Callan et al. | |
| 2004/0162484 A1* | 8/2004 | Nemoto | A61B 6/485 600/420 |
| 2004/0199076 A1* | 10/2004 | Nemoto | A61M 5/14546 600/432 |
| 2004/0242996 A1 | 12/2004 | Trombley, III et al. | |
| 2004/0254525 A1* | 12/2004 | Uber, III | A61M 5/007 604/67 |
| 2005/0059924 A1* | 3/2005 | Katz | A61M 5/14228 604/20 |
| 2005/0070848 A1* | 3/2005 | Kim | A61M 5/2053 604/140 |
| 2005/0104444 A1 | 5/2005 | Callan et al. | |
| 2005/0230575 A1* | 10/2005 | Zelenski | A61G 7/0503 248/176.1 |
| 2005/0234407 A1* | 10/2005 | Spohn | A61M 5/007 604/253 |
| 2005/0234428 A1* | 10/2005 | Spohn | A61M 5/007 604/533 |
| 2006/0079768 A1 | 4/2006 | Small et al. | |
| 2006/0079842 A1 | 4/2006 | Small et al. | |
| 2006/0079843 A1 | 4/2006 | Brooks et al. | |
| 2006/0178632 A1 | 8/2006 | Trombley, III et al. | |
| 2007/0083152 A1* | 4/2007 | Williams, Jr. | A61M 5/172 604/65 |
| 2007/0100282 A1* | 5/2007 | Small | A61M 5/14566 604/151 |
| 2007/0129705 A1 | 6/2007 | Trombley, III et al. | |
| 2007/0161970 A1* | 7/2007 | Spohn | A61M 5/007 604/533 |
| 2007/0197963 A1* | 8/2007 | Griffiths | A61M 5/007 604/97.01 |
| 2007/0213662 A1* | 9/2007 | Kalafut | A61M 5/14546 604/96.01 |
| 2007/0225661 A1 | 9/2007 | Ash et al. | |
| 2007/0282263 A1 | 12/2007 | Kalafut et al. | |
| 2008/0021371 A1* | 1/2008 | Rubinsky | A61B 18/1492 604/20 |
| 2008/0086087 A1* | 4/2008 | Spohn | A61M 5/007 604/151 |
| 2008/0091142 A1 | 4/2008 | Trombley, III et al. | |
| 2008/0172006 A1* | 7/2008 | Hicks | A61M 39/24 604/249 |
| 2008/0177126 A1* | 7/2008 | Tate | A61M 5/14 600/5 |
| 2009/0076383 A1 | 3/2009 | Toews et al. | |
| 2009/0112164 A1* | 4/2009 | Reilly | A61M 5/16827 604/151 |
| 2009/0149743 A1* | 6/2009 | Barron | A61M 5/007 600/431 |
| 2009/0163860 A1 | 6/2009 | Patrick et al. | |
| 2009/0171191 A1 | 7/2009 | Patrick et al. | |
| 2009/0171193 A1 | 7/2009 | Patrick et al. | |
| 2009/0171194 A1 | 7/2009 | Patrick et al. | |
| 2009/0171316 A1 | 7/2009 | Patrick et al. | |
| 2009/0208385 A1* | 8/2009 | Howorth | A61M 5/007 422/179 |
| 2009/0221914 A1* | 9/2009 | Barrett | A61M 5/007 600/431 |
| 2009/0234226 A1 | 9/2009 | Nemoto | |
| 2009/0275829 A1* | 11/2009 | Agarwal | A61M 5/007 600/433 |
| 2009/0312740 A1* | 12/2009 | Kim | A61M 25/10188 604/500 |
| 2010/0113887 A1* | 5/2010 | Kalafut | A61M 5/007 600/300 |
| 2010/0114040 A1* | 5/2010 | Schriver | A61M 5/1407 604/246 |
| 2010/0114064 A1* | 5/2010 | Kalafut | A61B 5/411 604/508 |
| 2010/0130935 A1 | 5/2010 | Hieb et al. | |
| 2010/0174183 A1* | 7/2010 | Schwartz | A61M 25/007 600/433 |
| 2010/0204574 A1* | 8/2010 | Duchon | A61B 6/481 600/432 |
| 2010/0217121 A1* | 8/2010 | Nemoto | A61B 6/481 600/432 |
| 2010/0293496 A1* | 11/2010 | Lafferty | A61M 5/14546 715/772 |
| 2011/0016392 A1* | 1/2011 | Humeniuk | A61M 5/14546 715/705 |
| 2011/0060219 A1 | 3/2011 | Small et al. | |
| 2011/0130745 A1 | 6/2011 | Shevgoor et al. | |
| 2011/0208047 A1 | 8/2011 | Fago | |
| 2011/0306932 A1 | 12/2011 | Patrick et al. | |
| 2011/0313401 A1 | 12/2011 | Ash et al. | |
| 2012/0016233 A1 | 1/2012 | Kalafut et al. | |
| 2012/0016234 A1 | 1/2012 | Nemoto et al. | |
| 2012/0022502 A1 | 1/2012 | Adams et al. | |
| 2012/0029433 A1* | 2/2012 | Michaud | A61M 5/1413 604/151 |
| 2012/0035471 A1* | 2/2012 | Lee-Sepsick | A61B 17/42 600/432 |
| 2012/0053457 A1 | 3/2012 | Fago | |
| 2012/0078218 A1 | 3/2012 | Barnes | |
| 2012/0123257 A1* | 5/2012 | Stokes, Jr. | A61M 5/1782 600/432 |
| 2012/0130236 A1 | 5/2012 | Nystrom | |
| 2012/0204997 A1 | 8/2012 | Winn et al. | |
| 2012/0253182 A1 | 10/2012 | Patrick et al. | |
| 2012/0253269 A1 | 10/2012 | Patrick et al. | |
| 2013/0030290 A1* | 1/2013 | Nemoto | A61M 5/14566 600/432 |
| 2013/0053692 A1 | 2/2013 | Barron et al. | |
| 2013/0066201 A1 | 3/2013 | Duchon et al. | |
| 2013/0066202 A1 | 3/2013 | Barron et al. | |
| 2013/0067416 A1 | 3/2013 | Barron et al. | |
| 2014/0052009 A1 | 2/2014 | Nystrom et al. | |
| 2014/0081214 A1 | 3/2014 | Hieb et al. | |
| 2014/0088494 A1* | 3/2014 | Shearer, Jr. | A61M 5/00 604/67 |
| 2014/0088559 A1 | 3/2014 | Fago | |
| 2014/0180084 A1 | 6/2014 | Vilks | |
| 2014/0224829 A1* | 8/2014 | Capone | B05B 11/3015 222/23 |
| 2014/0249485 A1 | 9/2014 | Trombley, III et al. | |
| 2014/0276040 A1* | 9/2014 | Schriver | A61M 5/16827 600/432 |
| 2015/0005715 A1 | 1/2015 | Cowan et al. | |

(56) References Cited

U.S. PATENT DOCUMENTS

| | | | | |
|---|---|---|---|---|
| 2015/0202362 A1* | 7/2015 | Wolff | ............... | A61M 5/14232 604/152 |
| 2015/0217042 A1* | 8/2015 | Schriver | ............ | A61M 5/1407 600/432 |
| 2016/0051753 A1 | 2/2016 | Barnes | | |

FOREIGN PATENT DOCUMENTS

| | | |
|---|---|---|
| AU | 2009319939 | 6/2010 |
| AU | 2011308664 | 5/2013 |
| CA | 2583726 | 4/2006 |
| CA | 2657479 | 1/2008 |
| CA | 2713221 | 9/2009 |
| CA | 2744693 | 6/2010 |
| CN | 101039711 | 9/2007 |
| CN | 101355975 | 1/2009 |
| CN | 101612046 | 12/2009 |
| CN | 101612426 | 12/2009 |
| CN | 101612427 | 12/2009 |
| CN | 101960458 | 1/2011 |
| CN | 102264413 | 11/2011 |
| CN | 102264414 | 11/2011 |
| CN | 102365106 | 2/2012 |
| CN | 103209729 | 7/2013 |
| CN | 103313753 | 9/2013 |
| CN | 103379928 | 10/2013 |
| CN | 103550845 | 2/2014 |
| CN | 104307067 | 1/2015 |
| EP | 0345396 | 12/1989 |
| EP | 0346950 | 12/1989 |
| EP | 0702966 | 3/1996 |
| EP | 1090650 | 4/2001 |
| EP | 1091164 | 4/2001 |
| EP | 1401519 | 3/2004 |
| EP | 1521606 | 4/2005 |
| EP | 1835959 | 9/2007 |
| EP | 2037982 | 3/2009 |
| EP | 2231230 | 9/2010 |
| EP | 2301605 | 3/2011 |
| EP | 2301606 | 3/2011 |
| EP | 2301608 | 3/2011 |
| EP | 2314335 | 4/2011 |
| EP | 2370128 | 10/2011 |
| EP | 2392379 | 12/2011 |
| EP | 2416821 | 2/2012 |
| EP | 2468350 | 6/2012 |
| EP | 2469437 | 6/2012 |
| EP | 2621577 | 8/2013 |
| EP | 2675497 | 12/2013 |
| EP | 2934623 | 10/2015 |
| FR | 2757772 | 7/1998 |
| FR | 2804609 | 8/2001 |
| GB | 2274148 | 7/1994 |
| JP | 2004194721 A * | 7/2004 ............ A61M 5/145 |
| JP | 2004538052 | 12/2004 |
| JP | 2008515603 | 5/2008 |
| JP | 2008521506 | 6/2008 |
| JP | 2009011856 | 1/2009 |
| JP | 2009061284 | 3/2009 |
| JP | 2009516577 | 4/2009 |
| JP | 2009542414 | 12/2009 |
| JP | 2010514502 | 5/2010 |
| JP | 2011516111 | 5/2011 |
| JP | 2011147796 | 8/2011 |
| JP | 2011218194 | 11/2011 |
| JP | 2012509739 | 4/2012 |
| JP | 2012509741 | 4/2012 |
| JP | 2012091010 | 5/2012 |
| JP | 2012091012 | 5/2012 |
| JP | 2012091013 | 5/2012 |
| JP | 2012091014 | 5/2012 |
| JP | 2012101069 | 5/2012 |
| JP | 2012148145 | 8/2012 |
| JP | 2012523276 | 10/2012 |
| JP | 2013240720 | 12/2013 |
| JP | 2013545547 | 12/2013 |
| JP | 2014111185 | 6/2014 |
| JP | 2014138870 | 7/2014 |
| JP | 2014138871 | 7/2014 |
| JP | 2014144348 | 8/2014 |
| JP | 2014176645 | 9/2014 |
| JP | 2014195743 | 10/2014 |
| JP | 2014204999 | 10/2014 |
| JP | 2015027578 | 2/2015 |
| JP | 2016032764 | 3/2016 |
| JP | 2016093697 | 5/2016 |
| KR | 20080081286 | 9/2008 |
| KR | 20110110109 | 10/2011 |
| KR | 20110110110 | 10/2011 |
| KR | 20130101594 | 9/2013 |
| KR | 101658900 | 9/2016 |
| RU | 2011126168 | 1/2013 |
| RU | 2011126169 | 1/2013 |
| WO | WO9924094 | 5/1999 |
| WO | WO9924095 | 5/1999 |
| WO | WO0006233 | 2/2000 |
| WO | WO0016849 | 3/2000 |
| WO | WO0059569 | 10/2000 |
| WO | WO02096487 | 12/2002 |
| WO | WO03039646 | 5/2003 |
| WO | WO2006044409 | 4/2006 |
| WO | WO2006058280 | 6/2006 |
| WO | WO2007062315 | 5/2007 |
| WO | WO2007100396 | 9/2007 |
| WO | WO2007116865 | 10/2007 |
| WO | WO2008008221 | 1/2008 |
| WO | WO2008085421 | 7/2008 |
| WO | WO2009041004 | 4/2009 |
| WO | WO2009086182 | 7/2009 |
| WO | WO2009114285 | 9/2009 |
| WO | WO2010062804 | 6/2010 |
| WO | WO2010062807 | 6/2010 |
| WO | WO2010110429 | 9/2010 |
| WO | WO2010117922 | 10/2010 |
| WO | WO2012040249 | 3/2012 |
| WO | WO2012044897 | 4/2012 |
| WO | WO2012064866 | 5/2012 |
| WO | WO2012071314 | 5/2012 |
| WO | WO2012112347 | 8/2012 |
| WO | WO2014028103 | 2/2014 |
| WO | WO2014099985 | 6/2014 |

OTHER PUBLICATIONS

Goldstein et al., A Novel Automated Injection System for Angiography, Journal of Interventional Cardiology, vol. 14, No. 2, 2001, pp. 147-152.

Mueller et al., Prevention of Contrast Media-Associated Nephropathy: Randomized Comparison of 2 Hydration Regimens in 1620 Patients Undergoing Coronary Angioplasty, Arch Internal Medicine, vol. 162, 2002, pp. 329-336.

Costa, More Than Skin Deep: An Overview of Iodinated Contrast Media, The Journal of the Association of Vascular Access, vol. 8, No. 4, 2003, pp. 34-39.

Schoellnast et al., Aortoiliac Enhancement During Computed Tomography Angiography with Reduced Contrast Material Does and Saline Solution Flush: Influence on Magnitude and Uniformity of the Contrast Column, Investigative Radiology, vol. 39, No. 1, Jan. 2004, pp. 20-26.

Utsunomiya et al., Cardiac 16-MDCT for Anatomic and Functional Analysis: Assessment of a Biphasic Contrast Injection Protocol, American Journal of Roentgenology, vol. 187, Sep. 2006.

Kaluski et al., Automated Contrast Injectors for Angiography: Devices, Methodology, and Safety, Catheterization and Cardiovascular Interventions, vol. 74, Apr. 29, 2009, pp. 459-464.

Buerke et al., Automatic MDCT Injectors: Hygiene and Efficiency of Disposable, Prefilled, and Multidosing Roller Pump Systems in Clinical Routine, American Journal of Roentgenology, vol. 197, Aug. 2011, pp. W226-W232.

(56) References Cited

OTHER PUBLICATIONS

Written Opinion of the Internation Searching Authority for PCT/US13/61397 (dated 2013).
Leslie et al., A New Simple Power Injector, American Journal of Roentgenology, vol. 128, Mar. 1977, pp. 381-384.
McCarthy et al., The Use of a Flow Rate Injector for Contrast-Enhanced Computed Tomography, Radiology, vol. 151, Jun. 1984, p. 800.
Thompson, A Practical Approach to Modern Imaging Equipment, 1985, pp. 142-153.
Tortorici et al., Advanced Radiographic and Angiographic Procedures With an Introduction to Specialized Imaging, 1995, pp. 123-127.
Prince et al., 3D Contrast MR Angiography, 1997 pp. 18-21.
Dec. 11, 2013 PCT-US-13-061397 IPRP.
Dec. 17, 2013 PCT-US-13-061397 ISR.
Dec. 17, 2013 PCT-US-13-061397 WOSA.

\* cited by examiner

SHELL OPTIONS 685

Saline 85 mL / 120 mL

Contrast 45 mL / 120 mL

Vent 705 | Purge 707 | Fill 709

Vent 711 | Purge 713 | Fill 715

Installed 35 min. ago 703

Disable Auto Refill Option 719 | Remove Cartridge 721

Figure 50

SOURCE OPTIONS 683

Saline 85 mL / 120 mL — Edit 723

Contrast 45 mL / 120 mL — Edit 725

Replace Sources 727

Figure 51

PATIENT OPTIONS 687

Saline 85 mL / 120 mL

Edit Fluid Maximums 729

Contrast 45 mL / 120 mL

Edit Fluid Maximums 731

Figure 52

METHOD TO PROVIDE INJECTION SYSTEM PARAMETERS FOR INJECTING FLUID INTO PATIENT

CROSS REFERENCE TO RELATED APPLICATIONS

This application claims priority under 35 U.S.C. 119(e) to U.S. provisional patent application 61/754,687, filed Jan. 21, 2013, and claims priority under 35 U.S.C. 120 as a continuation-in-part of PCT/US13/61397 filed Sep. 24, 2013, of which are incorporated herein by reference.

FIELD OF THE INVENTION

The disclosure generally relates to fluid dispensing machines and, more particularly, relates to fluid injection systems and methods used to automatically inject various fluids, such as saline, contrast, or a mixture of both, into a patient.

BACKGROUND

During medical procedures fluids of different types need to be injected into human tissue and vascular structures. Various medical procedures require a radiographic image of a vascular structure to be obtained by injecting radiographic contrast material through a procedure catheter into a hollow anatomical structure, such as a blood vessel, artery, vein, or heart chamber. X-rays are then passed through the region of the body in which the contrast material was injected. The X-rays are absorbed by the contrast material causing a radiographic outline or image of the hollow anatomical structure containing the contrast material. The x-ray images of the hollow anatomical structures filled with the contrast material are usually recorded on memory, such as on film or videotape, and displayed on a fluoroscope monitor. When a series of different fluids are to be administered, or a series of injections are required, it is often necessary to flush one fluid from the injection line before the next fluid is administered. For example, during angioplasty, the procedure catheter is often flushed with saline before and/or after the addition of contrast solution. Further, it is also necessary to purge any injection lines of air and to prevent the reintroduction of air into the lines.

The injection of the contrast or other fluids can be performed either manually or automatically. In both injection procedures, a procedure catheter is inserted into a hollow anatomical structure, which in turn is connected to a fluid line leading to a valve or manifold which is in fluid communication with an injector or syringe. The plunger of the injector or syringe is then either manually or automatically depressed to inject fluid through the fluid line, through the procedure catheter, and into the patient.

The most commonly used apparatus for these types of procedures involves the connection of a catheter to a valve or manifold having a number of stopcock valves. Movement of fluids between selected fluid sources, other apparatus, and to the procedure catheter and patient is typically accomplished with a syringe or other manual injection device. The physician is typically required to selectively open and close the valves or manifold to control the source, path and direction of the fluid flow during a procedure. The physician may also be required to draw fluid, take a blood sample, remove waste, inject medication, or flush fluid out of the injection device repeatedly during a procedure.

Because a physician is required to manipulate a number of stopcock valves during a procedure to achieve a desired flow path to or from the procedure catheter, it takes training to learn how to properly operate one of the prior art manifolds. Further, because it may not be immediately evident from looking at the manifold which way the fluid is flowing, it is easy to make an improper connection resulting in no unintended fluid delivery into the patient. Because a number of stopcock valves are involved in the prior art manifolds, the handles must be small so as to not cause interference with one another. However, the small handles can be difficult to grasp and manipulate. Additionally, physicians often develop a "tactile feel" for infusing fluids through catheters with the syringe or other injection device, maintaining the infusion pressure within desired pressure ranges to avoid damaging catheters, vessel dissection, damaging catheter balloons or unintentional damage to any hollow anatomical structures while still achieving flows sufficient for contrast-enhanced imaging.

In certain situations, it is necessary to dilute the concentration of contrast being injected into a patient. For example, in those patients with renal insufficiency incapable of processing concentrated contrast through their system, or in cases where a large amount of contrast is used, such as complicated coronary interventions (PTCA) or peripheral (PTA) cases with runoffs, direct injections of contrasts, are not desired. Accordingly, it may be necessary to mix the contrasts and saline prior to injection to arrive at the appropriate dilution percentage. The goal is to obtain a dilution percentage that is safe for the patient and still provides a clear image. Such processes are necessarily slow and are currently difficult to achieve using known injectors in the art. There is a need in the art to easily mix contrast and saline in-line and control the dilatation of the concentration of contrast being injection; thereby preventing unnecessary contrast from entering the patient's body and also reducing overall contrast used allowing for a cost saving by the hospital.

To address these issues, an improved automated fluid management system has been developed and is disclosed herein. Automated injection system disclosed in this application advantageously provide physicians with a simplified process for selecting fluid sources to inject into hollow anatomical structures at high pressures up to 1400, and typically between 900-1200 psi.

Traditional injection procedures for coronary injections as commonly known in the art may include the use of a manifold, as described above, for controlled injections of both saline and contrast. If high volume injections are then required the manifold may be removed and the user may have to then attached an automated injectors to the procedure catheter. Therefore, a need in the art exists, of which this invention satisfies, for an automated injector that can be used with controlled injection of both saline and contrast. An advantage of this system is incorporating the ability to perform controlled injections historically done by manifolds together the ability to simultaneously automate injection of contrast, saline, or a mixture of both in-lines at high pressures.

SUMMARY OF THE INVENTION

In accordance with one aspect of the disclosure, an injection system is provided which may comprise of a multi-use subassembly, a single-use subassembly, a fitting to fluidly connect the multi-use and single-use subassemblies, a hand held controller, a user interface, and an injector. The multi-use subassembly may comprise a protective shell, at least one power actuated syringe, and at least one automated rotary valve, a venting system, and high pressure tubing. The single-use subassembly may comprise high pressure tubing, pressure protection valve, pressure transducer, and a catheter connection. In this embodiment, the multi-patient subassembly may be capable of multiple injections for a single patient, multiple patients, whereas the single-use subassembly may be capable of multiple injections for a single patient.

In accordance with another aspect of the disclosure, an injection system may also comprise a portable cart and a mounting system. The mounting system comprises different mounting subassemblies, including but not limited to, a cart mounting option, a rail or bed mounting option, and a ceiling or wall mounting option.

In yet another embodiment of the invention, the injection system may comprise a multi-use subassembly, a single-use subassembly, a hand held controller, a user interface, an injector housing, and a fitting to fluidly connect the multi-use and single-use subassemblies for single patient use only. In this embodiment, the multi-use subassembly and single-use subassembly may both be capable of multiple injections but for only a single patient use. The purpose of this embodiment is so the injection system may be used in combination with a contrast source intended for single patient use only.

Key advantages of this invention include an improved monitor/user interface system to facilitate automated and preset and/or customizable injections; ability to simultaneously inject a mixture of fluids (such as a mixture of saline and contrast) in line and in real time; interchangeable multi-use disposables to facilitate setup and preparation of injection system; an automated purge system; a special rotary valve for automated fill and injection; convex faced syringe barrel; enhanced rear barrel support means, hand controller providing user with a tactile or haptic feel during injections, and a side exit port syringe barrel used to shorten the shell and decrease overall injector footprint.

DESCRIPTION OF THE DRAWINGS

FIG. 50 is an illustration of a Shell Option Screen of the display of the system of FIG. 2.

FIG. 51 is an illustration of a Source Options Screen of the display of the system of FIG. 2.

FIG. 52 is an illustration of a Patient Options Screen of the display of the system of FIG. 2.

DETAILED EMBODIMENTS

Figure 1:
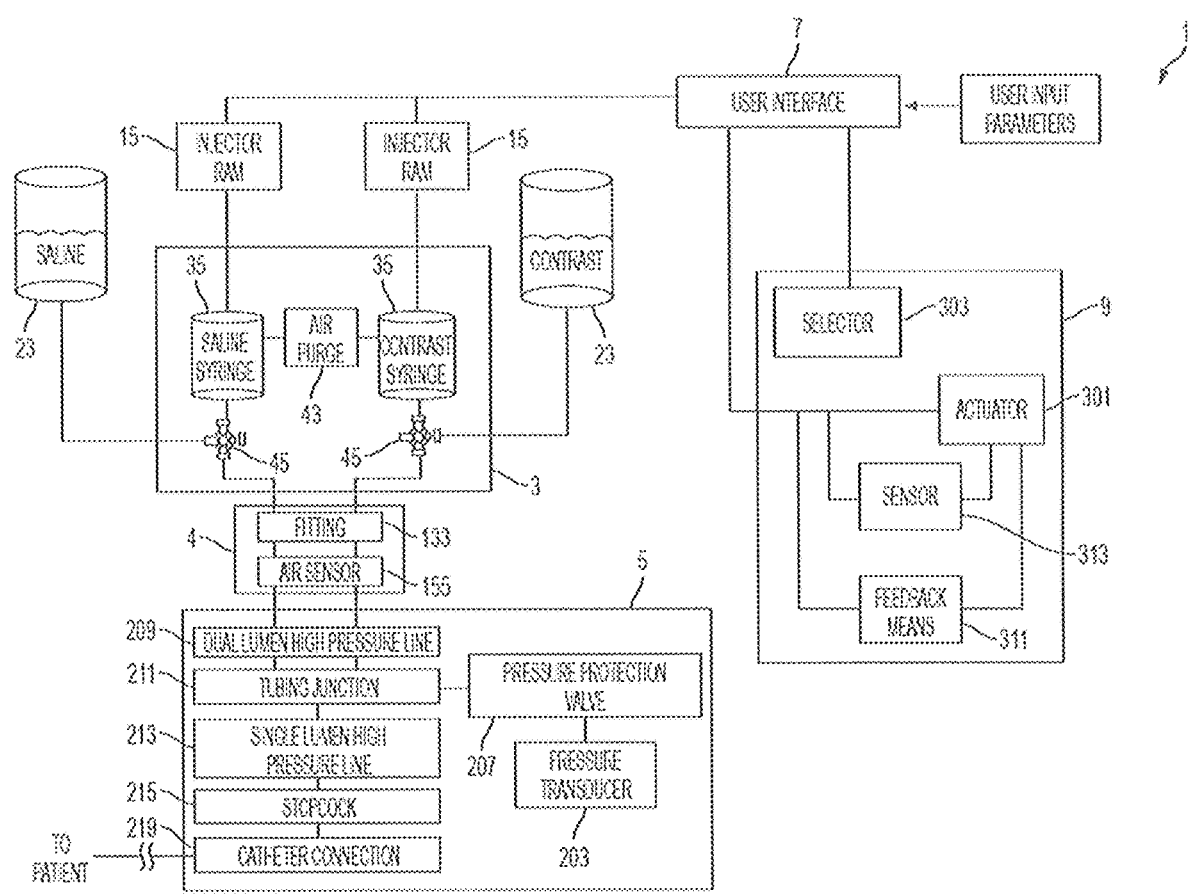
FIG. 1 is a schematic drawing of one embodiment of the injection system.

As seen in FIG. 1, a schematic of the automated fluid injection system 1 is shown. The injector system 1 is comprised of various components or subassemblies that may be combined together to form the overall system 1. The injector system 1 may allow the user to monitor invasive pressures or vascular blood pressure monitoring and perform dual injections of contrast, saline, a mixture of contrast and saline, or any other fluid, with the ability for variable mixing during medical procedures. The injection system 1 is capable of injecting fluids from the barrel 35 at both low and high pressures, for example any pressure up to 1,400 PSI or the pressure required by maximum catheter specifications as currently known in the art. The injector system 1 may include, but is not limited to, the user interface 7, a hand controller 9, at least one injector ram 15, at least one fluid source 23, a multi-use subassembly 3, a fitting housing 4, and a single-use subassembly 5. The hand controller 9 may further comprise, but is not limited to, a selector 303, an actuator 301, a sensor 313, and a feedback means 311. The multi-use subassembly 3 may further comprise, but is not limited to, at least one syringe barrel 35, an air purge or venting system 43, at least one automated valve 45. The fitting housing 4 may further comprise, but is not limited to, a fitting 133 and an air sensor 155. The single-use subassembly 5 may further comprise, but is not limited to, a dual lumen high pressure line 209, a tubing junction 211, a pressure protection valve 207, a disposable pressure transducer 203, a single lumen high pressure line 213, a stopcock 215 and a catheter connection 219. The single-use subassembly 5 may be in fluid connection with a procedure catheter (not shown). As described in more detail below, the various components and subassemblies shown in the schematic of FIG. 1 may change depending on the needs of the user.

Figure 2:
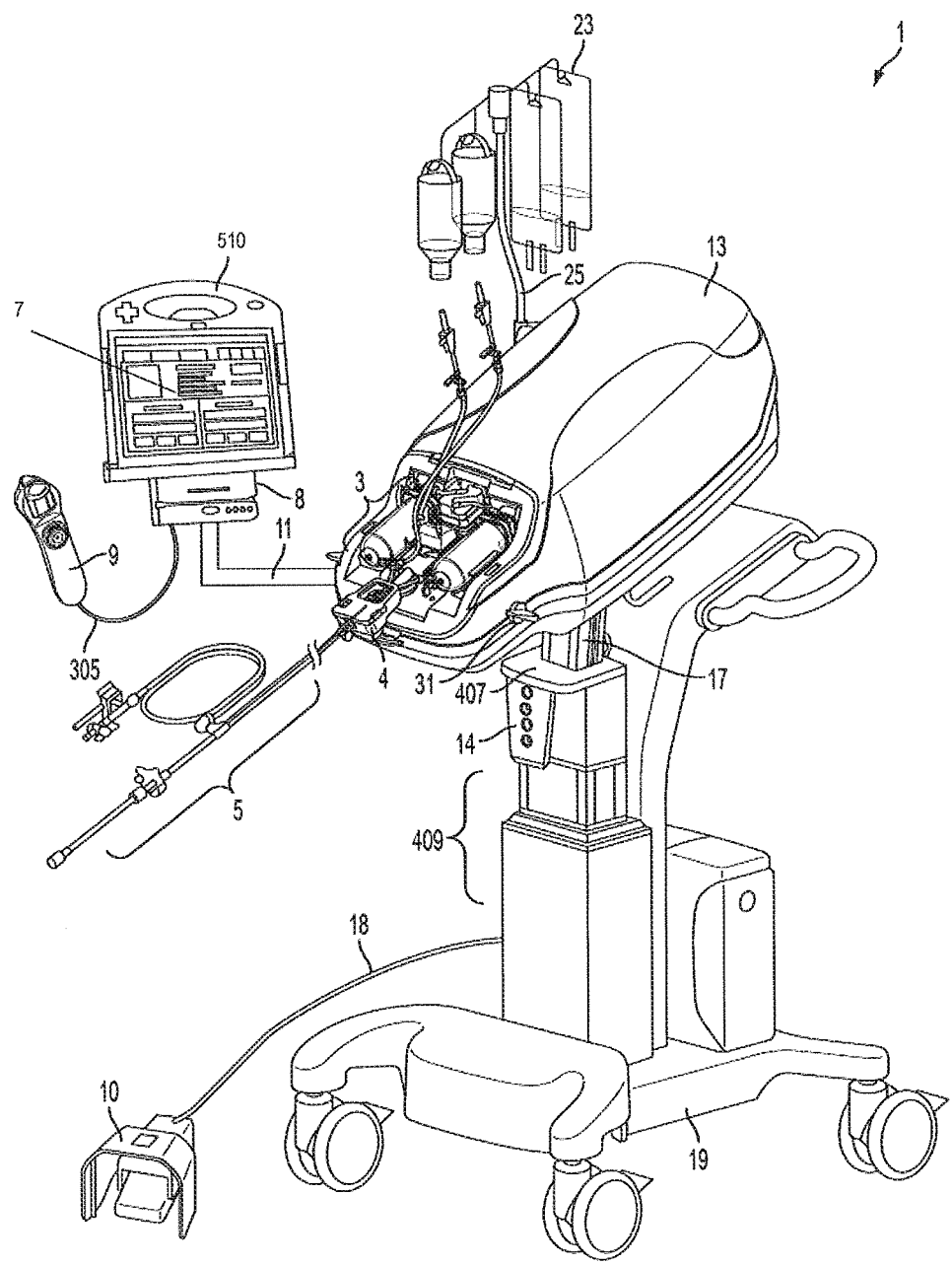
FIG. 2 is a side perspective view of the injection system.
Figure 3A:
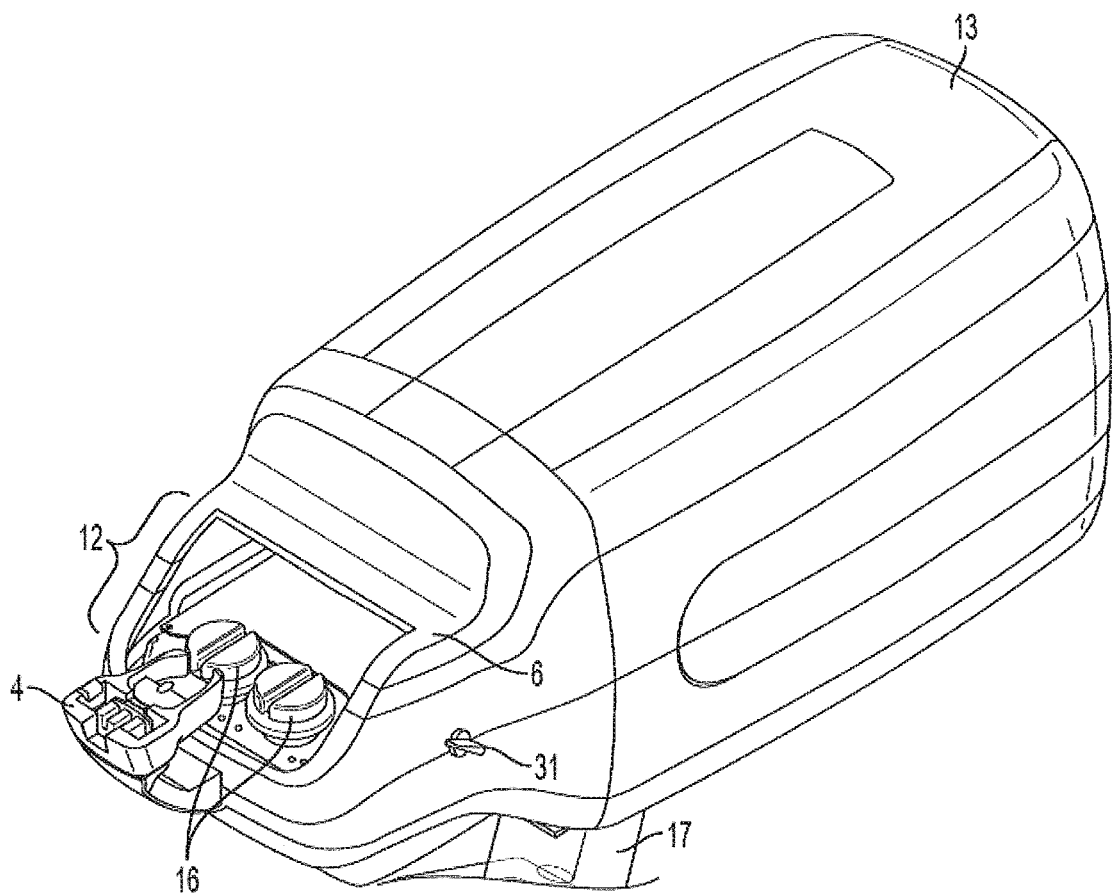
FIG. 3a is a side perspective view of the injector with cover closed; 3b is a side perspective view of the injector with the cover open.
Figure 3B:
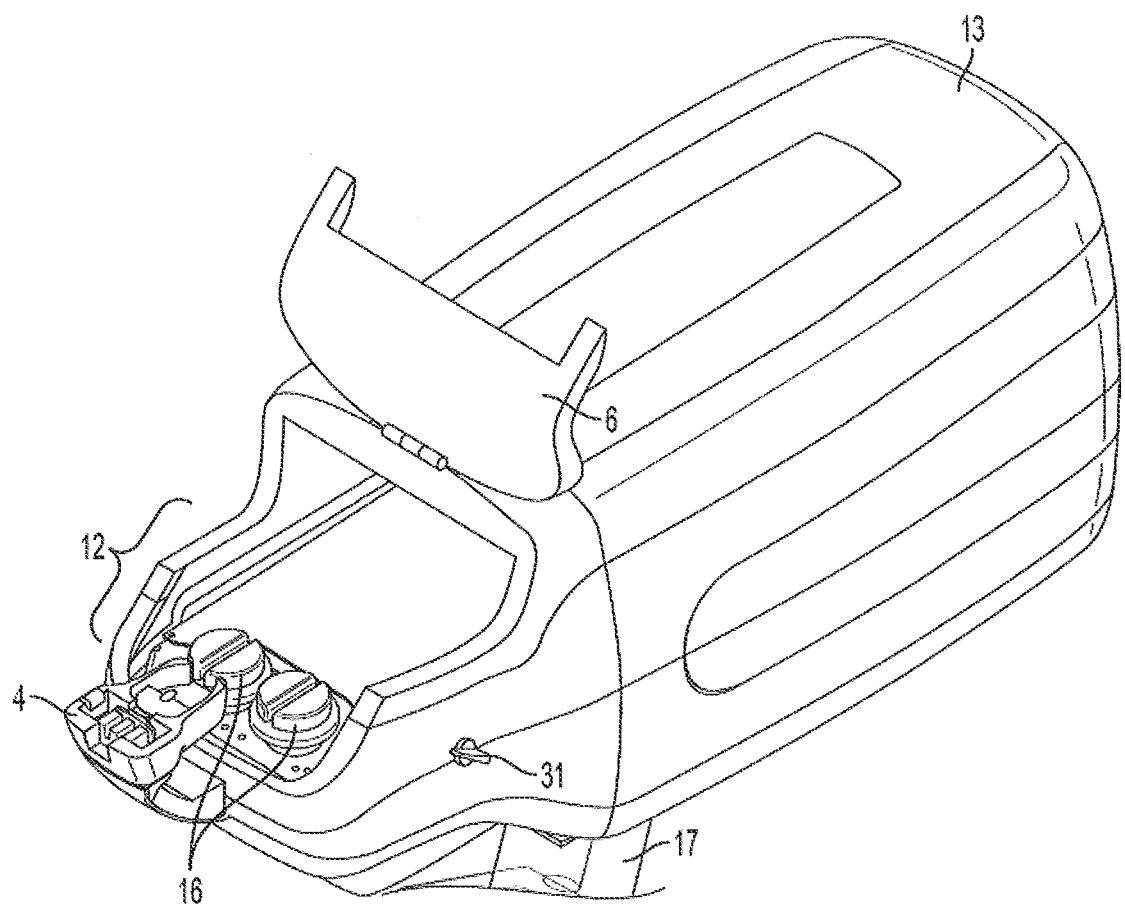
Figure 4:
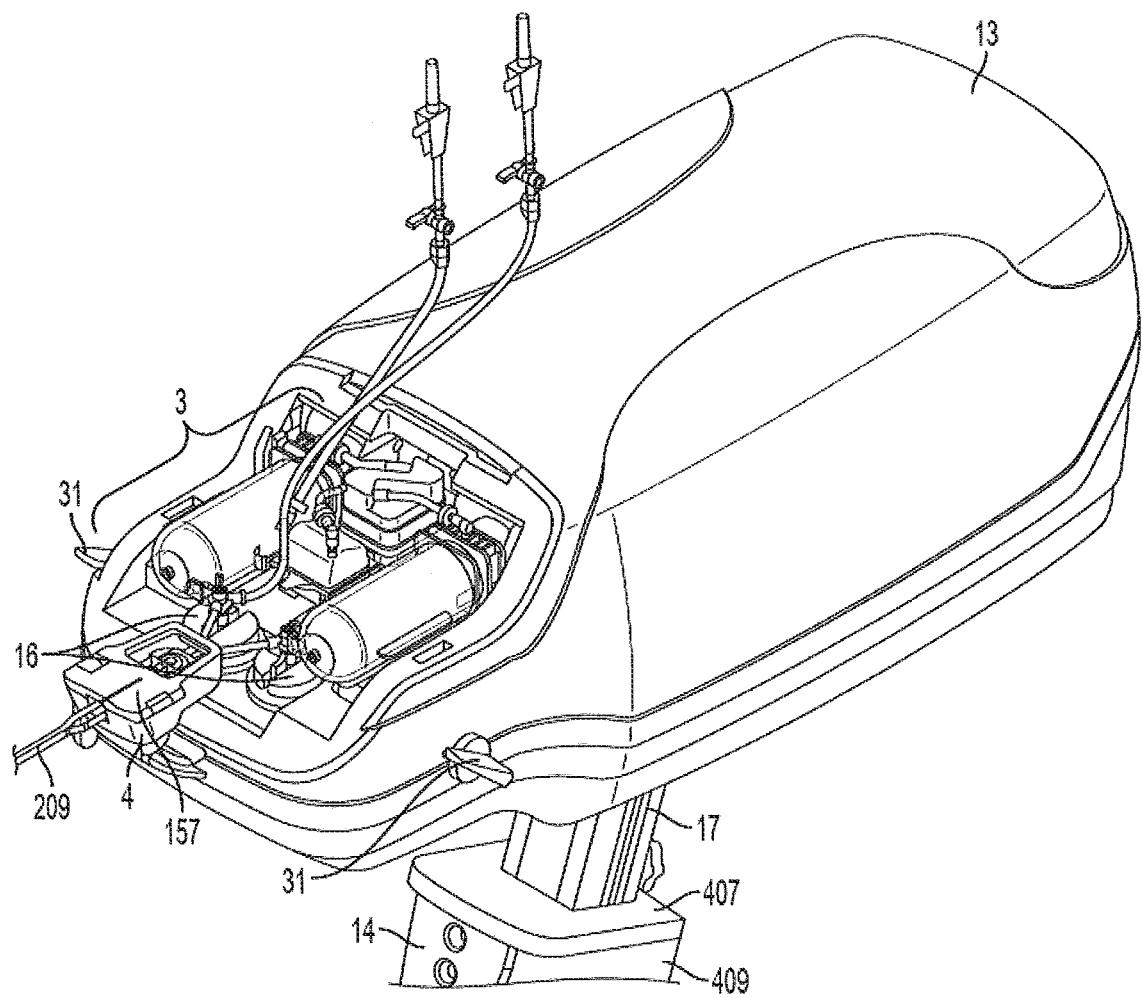
FIG. 4 is a side perspective view of the injector after the multi-use subassembly has been placed.

FIGS. 2-4 depicts one embodiment of the injector system 1. The injector system 1 may comprise of various components or subassemblies including, but not limited to, a multi-use subassembly 3, a single-use subassembly 5, a user interface 7, a hand controller 9, an injector housing 13, fluid source 23, a foot pedal 10, cover 6, locking handles 31, and a cart 19. For the sole purpose of clarity the cover 6 has been removed from FIGS. 2 and 4. The injector system 1 may also comprise a mount finger 14, a mounting plate 407, a connection arm 17, and a motorized base 409. The connection arm 17 is used to securely attach the injector housing 13 to a mount plate 407. A key feature of the injector system 1 is the interchangeable mounting system, described in more detail below, that allows the injector to be secured to various securement structures including, but not limited to, a cart 19, a bed rail 411 (as seen FIGS. 35-40), or a ceiling or wall mount (not shown).

The fluid sources 23 containing either saline or contrast may be secured to the housing 13 with a source arm 25. The arm 25 may be hinged or pivotally connected to the housing 13. The arm 25 may be collapsible or foldable to allow the user to reduce the footprint of the injector housing 13 when not in use. The user interface 7 may be securely attached to the housing 13 by an interface arm 11 that pivotally extends or retracts. It is advantageous that the user interface 7 is able to swing, pivot, or otherwise be manipulated in multiple directions during a procedure. It is common for the injector housing 13 to be placed away from the user during a procedure due to limited space, for example on the opposite side of the bed, so having the ability to manipulate the interface 7 in various directions is an advantage over injectors currently known in the art. The interface may have an identification card swipe 8. The hand controller 9 may be connected to the user interface 7 using various techniques, as described below, including a control cable 305. Similarly, the foot pedal 10 may be connected to user interface 7 using various techniques including a control cable 18.

The interface 7 is intended to control and display various aspects of operating the injector including, but not limited to, setting injection parameters, automated purging of system, automated injection, displaying real time injection status, and providing a user friendly interface for injector. Various selection tabs on the interface 7 may become highlighted, flash, grayed out, or have a visual indicator in order to depict and verify to the user that tab has been selected. An advantage of user interface 7 is that it reduces the user learning curve by programming the interface 7 to make it easier for users to navigate the system and simplify or automate the purging and injection sequences so to reduce possible user error. The interface 7 may be interactive via a touch screen so that user can select an option simply by pressing a visual aid on the screen. Alternatively, interface 7 may be voice activated or controlled via voice commands so instead of physically pressing a screen or tablet computer a user may control interface 7 using a head set or other similar voice command device.

The interface 7 may be software based and incorporated onto a touch screen tablet, PC, or a digital application used on a smart phone. Additionally, interface 7 may provide a shorter or faster setup time allowing for more time to conduct procedures. Interface 7 may provide for automatic syringe refill and air purging. The automatic refill option minimizes waste by allowing user to input a required amount of contrast, saline, or other fluid to be used per case.

User may also be able to define a maximum limit for total contrast or saline that can be injected into the patient with integrated warning signals to notify user when maximum has been reached.

The interface 7 may have a card swipe 8 or identification card reader as known in the art, as seen in FIG. 2. The purpose of the card swipe 8 is to allow the user to simply swipe their hospital identification card and the interface will automatically bring up preset settings. These settings may be changed at any time but having the ability to automatically call up preset settings may save the user time.

As seen in FIG. 3a-FIG. 4, housing 13 has a loading area 12 that the multi-use subassembly 3 may be placed or inserted into during setup. FIG. 3a shows the loading area 12 without the multi-use subassembly 3 in place. The loading area 12 has at least one valve actuator 16. The valve actuator 16 is designed so that the tab 46 of the automated valve 45 (see FIG. 4) may fit securely within the valve actuator 16. The movement of the valve actuator 16 is controlled by the interface 7 or hand controller 9. As described in more detail below, when the valve actuator 16 moves or rotates it simultaneously moves or rotates the valve tab 46 thereby controlling the position automated valve 45. The loading area 12 also may comprise a fitting housing 4 used to securely enclose the fitting that connects the multi-use assembly 3 to the single-use assembly 5. The loading area 12 may also comprise visual identifiers (not shown). The visual identifiers may include at least one light or LED (not shown) used to provide visual identification to the user of the current status of the injector. For example, the loading area 12 may have two visual identifiers in the form of different colored LEDs (not shown), one color to represent contrast and one color to represent saline. Each LED may be placed adjacent to the automated valve 16. Each LED may light up and provide user notice during injection of fluid or filing, purging, or venting of a barrel. For example, if just saline is being injected then only the corresponding LED is activated; if just contrast is being injected then only the corresponding LED may be activated; if both contrast and saline is being injected both LEDs may be activated.

Multi-use subassembly 3 may be inserted into loading area 12 and secured to the injector via a locking means such as a cover 6. To load the multi-use subassembly 3 into the loading area 12 the user must unlock the cover 6 by rotating the locking handles 31 and lifting the cover 6 away from the loading area 12, as seen in FIG. 3b. Once the cover 6 has been lifted, the user may place the multi-use subassembly 3 on the loading area 12 of the injector housing 13. The multi-use subassembly 3 is secured to the loading area 12 and injector housing 13 by placing the securement ridge 59 of barrels 35 into the rear barrel support means 79, as described in more detail below. Once the multi-use subassembly 3 is in place on the loading area 12 the user may close the cover 6 and rotate the locking handles 31 to securely enclose the multi-use subassembly 3 to the injector housing, as seen in FIG. 4.

Figure 5:
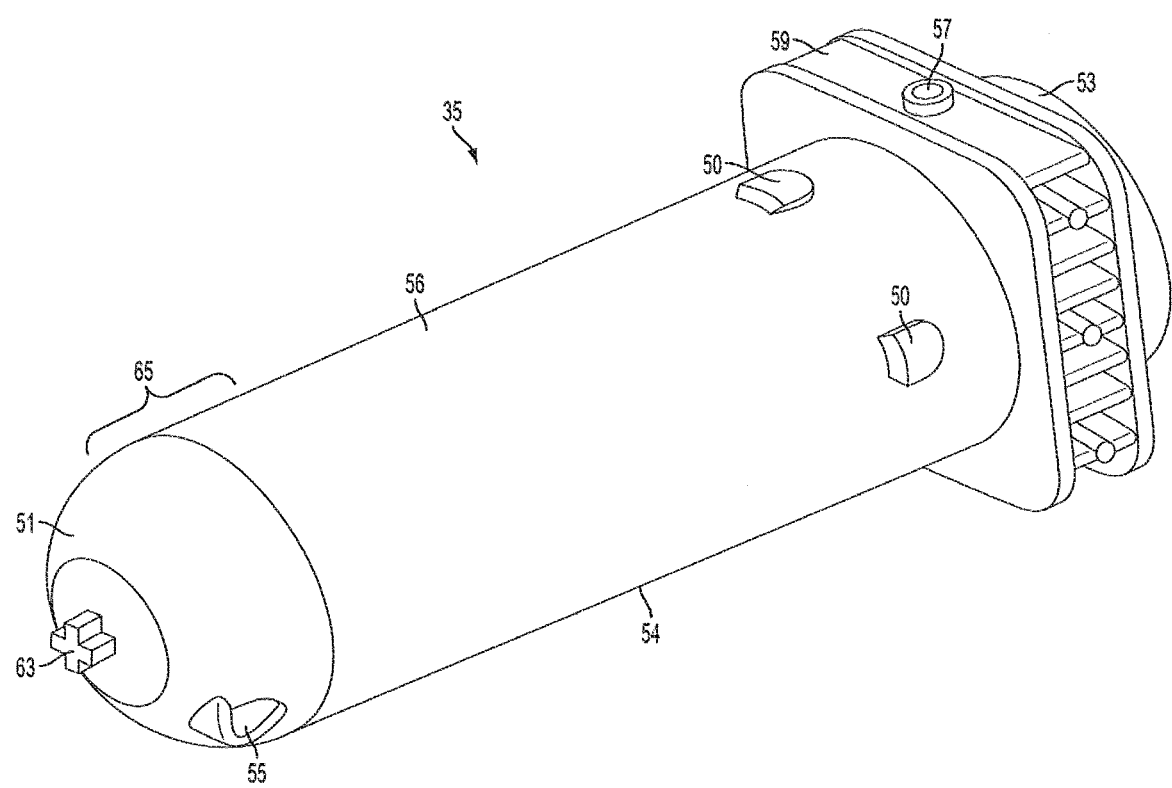
FIG. 5 is a side perspective view of the syringe barrel.
Figure 6:
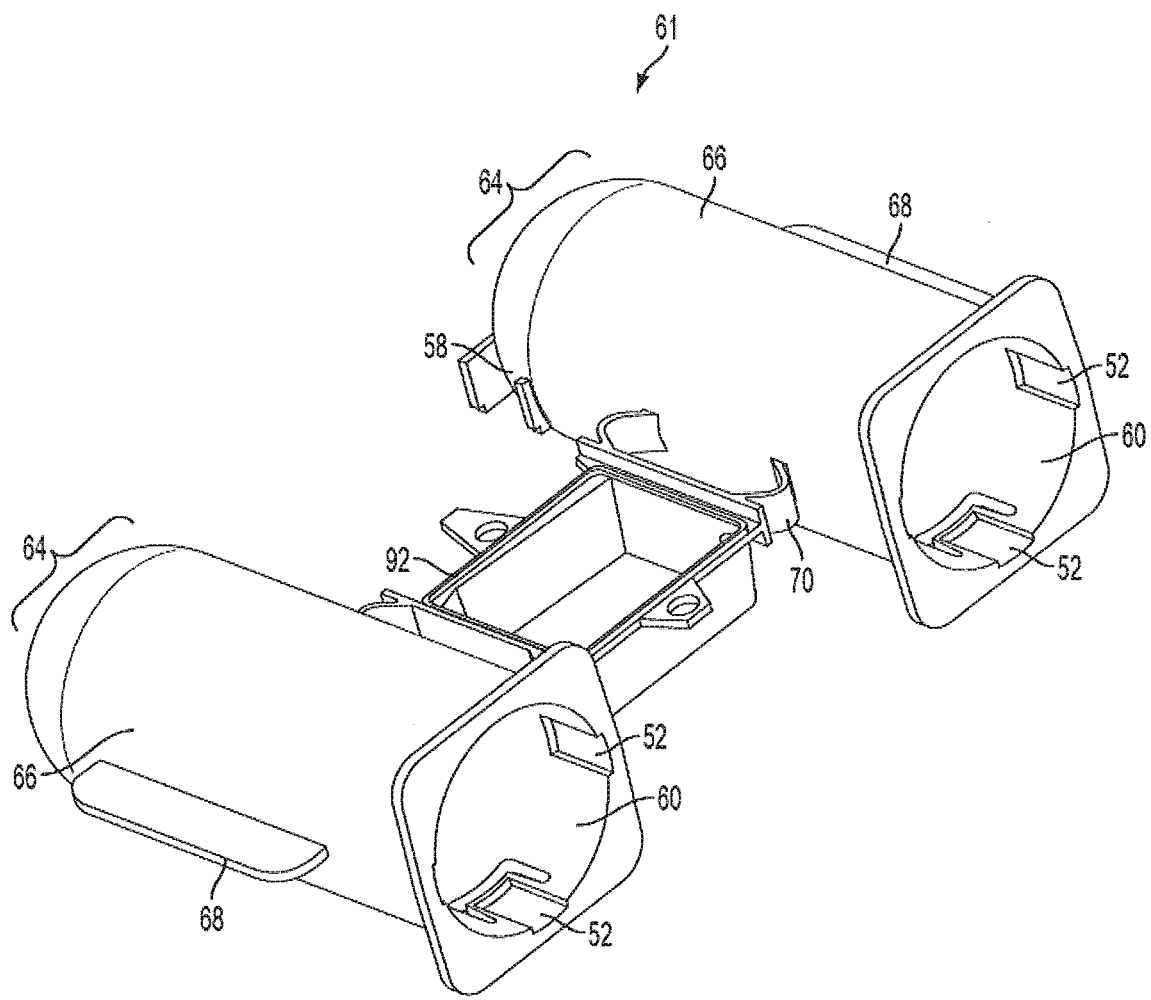
FIG. 6 is a rear perspective view of the outer protective shell.
Figure 7:
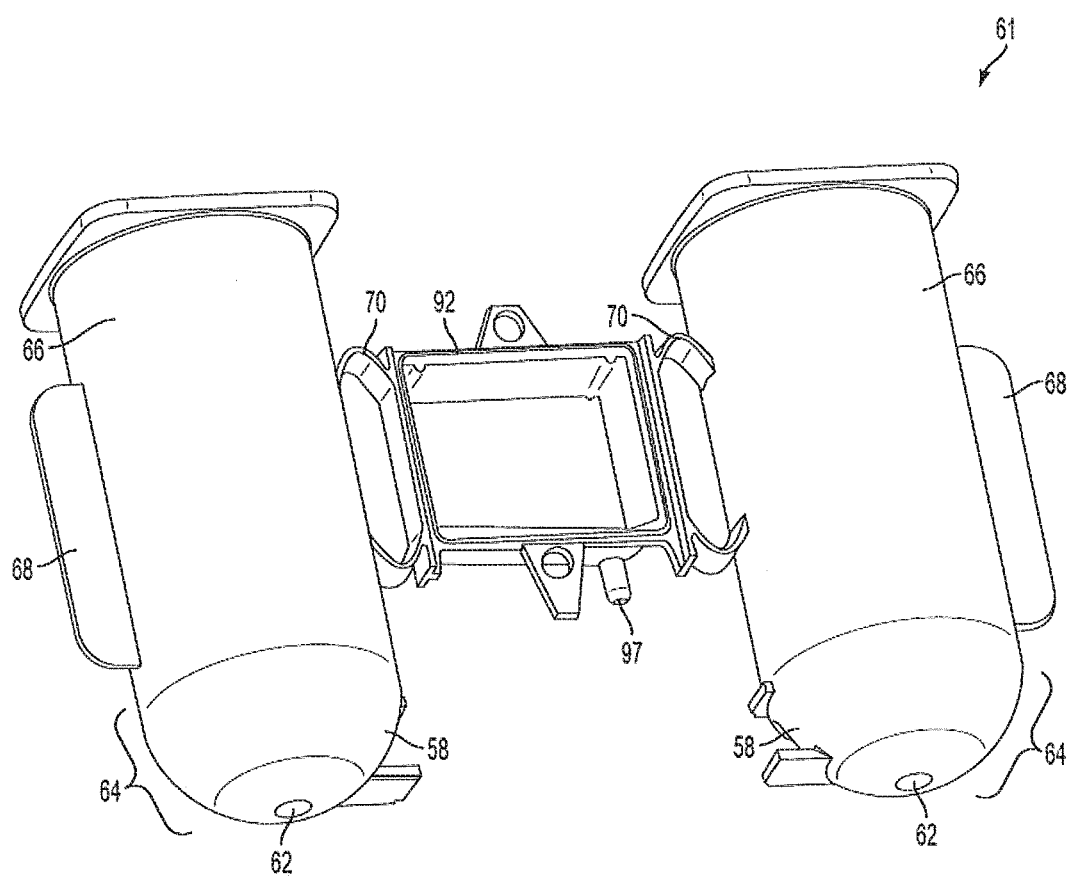
FIG. 7 is a side top perspective view of the outer protective shell.

The multi-use subassembly 3 may comprise of at least one syringe barrel 35 as seen in FIG. 5. Barrel 35 may further comprise a front end 51, back end 53, a first port 55, a second port 57, a securement ridge 59, an alignment nub 63, and anti-rotation means. The front end section 51 of syringe barrel 35, and similarly the front end section 64 of protective shell 61 as seen in FIG. 6-7, may be a semi-spherical convex, rounded, or bullet shape. An advantage of front end sections 51 having a semi-spherical or convex front profile is a reduction in stress points or risers. Stress risers occur at corners and/or sharp angles on injection-molded devices. By eliminating the sharp corners present in a conical shaped barrel, the component will be less prone to premature, stress-induced failures under high pressure conditions generated by power injection. An advantage of this design is an increase in strength that allows barrel 35 to be used multiple times under high pressure conditions. The front face 51 of barrel 35 also shortens overall barrel length—relative to standard conical shaped syringe barrels known in the art—allowing for smaller multi-use subassembly 3 and small injector footprint. It is advantageous for the injector to have a reduced footprint and overall smaller size because the procedure room in which injector is user becomes very crowded and space becomes limited. The design of this embodiment helps reduce overall size of injector thereby providing more room around the injector for hospital personnel to freely move. Syringe barrel 35 may be made from various materials able to withstand high temperatures or pressures including, but not limited to, clear polycarbonate, clear abs, or ultem.

The securement ridge 59 may be located towards the back end 53 of the barrel and extend radially a selected distance around the barrel 35. The securement ridge 59 may be injection molded together with barrel 35 to create a single piece component. Securement ridge 59 is shaped to fit within the rear barrel support means, as described in more detail below. The purpose of the securement ridge 59 is to provide additional support to the barrel 35 and also a means for securely connecting or attaching the barrel 35 to the injector housing 13. During injections the barrel 35 may come under high forces so it is important that the securement ridge 59 can withstand such forces because the ridge 59 may be the connection point for securely attaching barrel 35 to injector.

Figure 8:
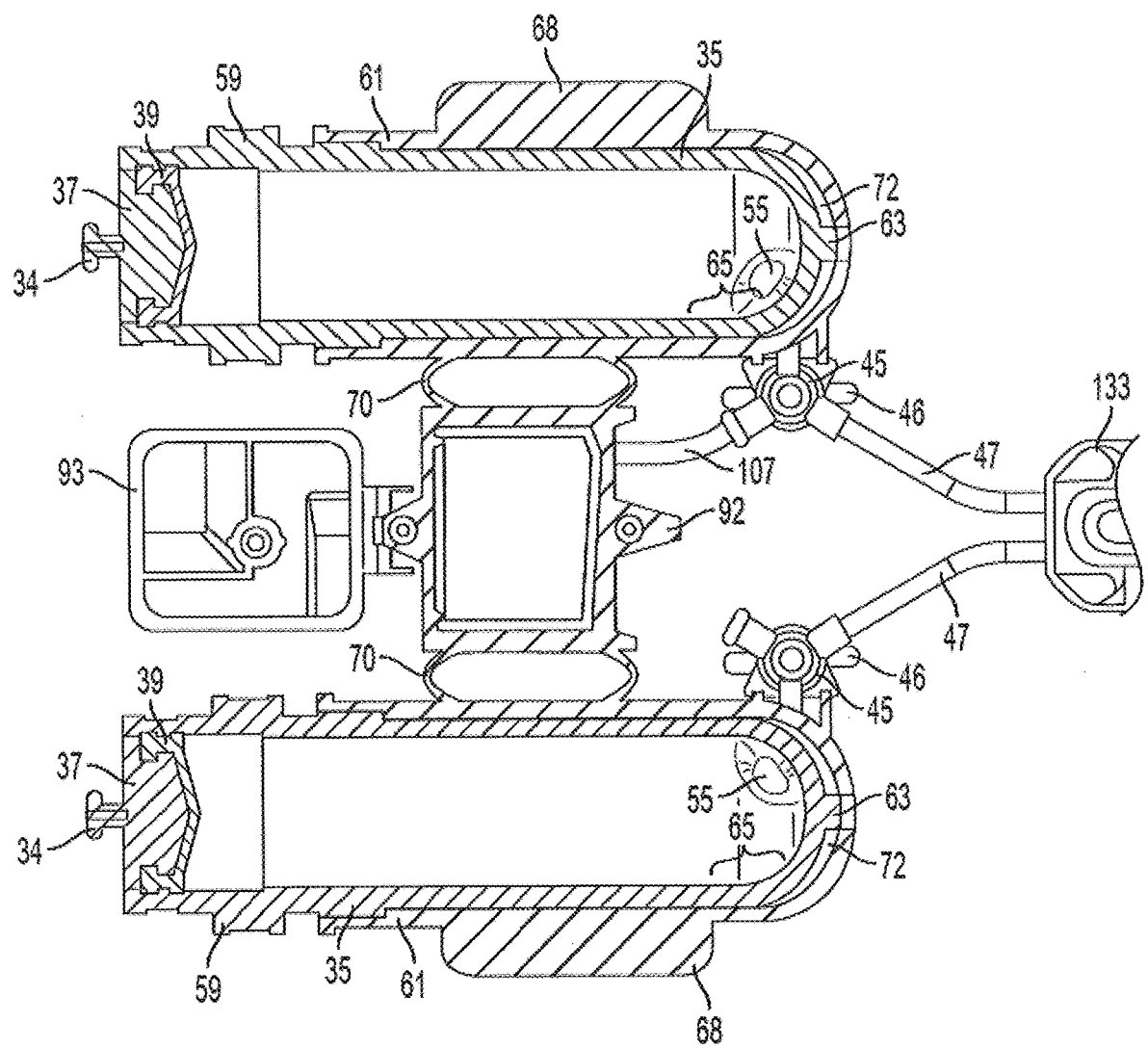
FIG. 8 is a top cross-section view of the multi-use subassembly.

The first port 55 is used to fill and inject fluids from the syringe barrel 35. The first port 55 can be located along the front end 51 of syringe barrel 35 and provides a fluid communication channel between the automated valve and interior of barrel body. In one embodiment, as shown in FIGS. 5 and 8, the first port 55 is positioned towards the front end 51 and bottom wall 54 and below the center axis of barrel 35.

Figure 12:
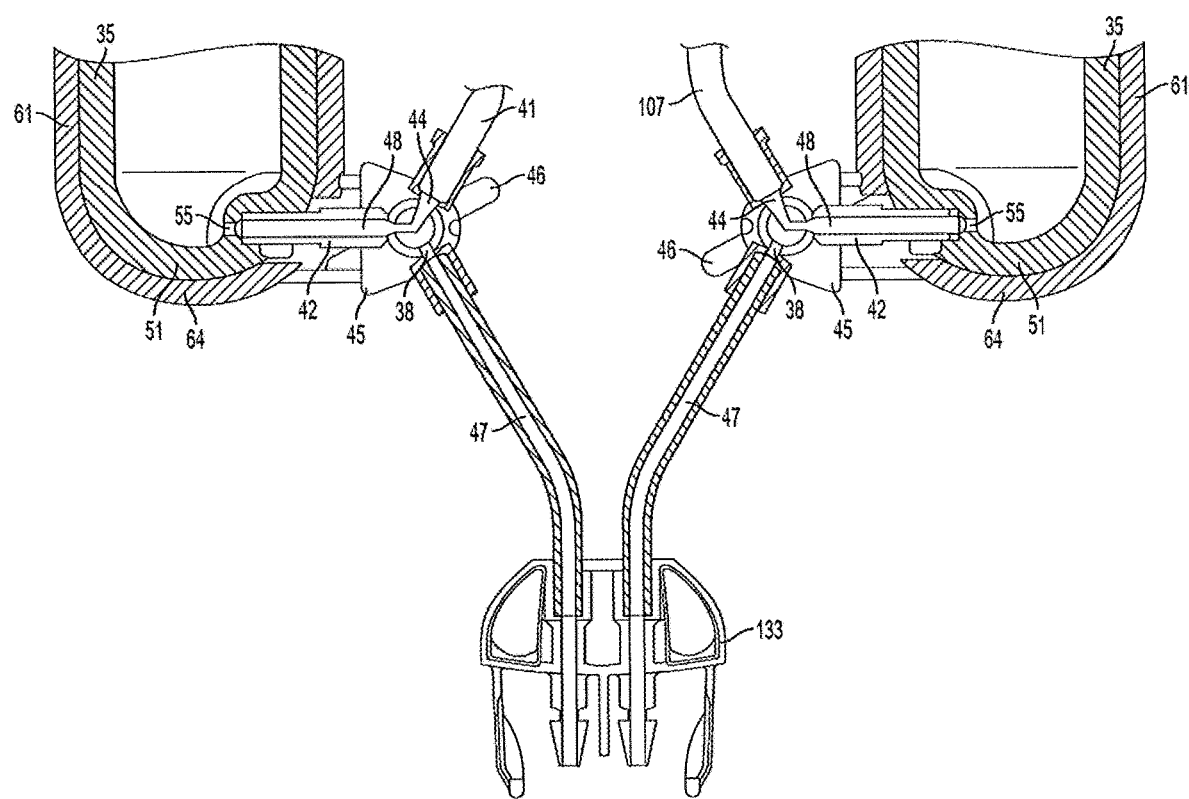
FIG. 12 is a partial top cross-sectional view of the multi-use subassembly.

First port 55 may be positioned on the front face 51 near the transition zone 65 between the barrel body and the front face 51. An advantage of positioning the first port 55 along the side wall of syringe barrel 35 is shortening the overall barrel length, thereby allowing for a smaller multi-use subassembly 3. Additionally, when the first port 55 is positioned along the side wall of barrel 35 the port 55 may be located a selected distance proximal to the tapering zone 65, an area along front end 51 of syringe where barrel 35 transitions from straight side wall to shaped end face, thereby reducing the risk of barrel cracking or fatigue. First port 55 of syringe barrel 35 may be inverted into the barrel 35, as seen in FIG. 12. An advantage of this design allows barrel 35 to be front loaded into the shell 61, as will be described in detail later.

The second port 57 located on top surface of securement ridge 59 is used for purging or venting the barrel 35 of unwanted air, as described in more detail below. The second port 57 may be located along the top of the securement ridge 59 as seen in FIG. 5. The second port 57 may provide fluid communication between inside the barrel chamber and a one-way check valve 113a, 113b of the venting system, as described in more detail below. Alternatively, the second port 57 may be located on the top wall 56 of the barrel 35 towards the back end 53 of the syringe barrel 35.

Referring now to FIG. 6-7, the system may include an outer protective shell 61 as a means of additional support intended to prevent syringe barrel 35 from over expansion, cracking, leaking or bursting during use. The protective shell 61 may include, but not limited to, a convex shaped front end 64, port holes 58, anti-rotation grooves 52 along the inner wall 60, alignment holes 62, placement tabs 68, connection arms 70, and the bottom half 92 of the fill chamber. Shell 61 may comprise two separate enclosure containers 66. The shell 61 is designed so each barrel 35 may be independently placed inside an enclosure container 66. Each container 66 has a port hole 58 that aligns with the first port 55 of the barrel 35. At least one connection arm 70 extending off each container 66 may securely attach to the bottom half 92 of the fill chamber, thereby connecting both containers 66 to form a single shell 61. The fill chamber 92 is part of the venting system 43 and is described in more detail below. Each container 66 may have a placement tab 68 so user may grip or hold the shell 61 during insertion or removal from injection housing 13. Shell 61 may be made from various materials able to withstand high temperatures or pressures including, but not limited to, clear polycarbonate or ultem.

The multi-use subassembly 3 may contain anti-rotation means to prevent the barrel 35 from twisting or rotating out of alignment during an injection or manufacture/assembly of the multi-use subassembly 3. As seen in FIG. 5-7, the barrel 35 and shell 61 are separate components and the anti-rotation means is used to ensure that the barrel 35 remains aligned within the shell 61 during use. The anti-rotation means on the barrel 35 may include an alignment nub 63 along the front end 51 and raised notches 50 along the outer surface of the barrel 35. The anti-rotation means of the shell 61 may include an alignment hole 62 along the front end 64 and groove 52 on inner wall 60, as seen in FIG. 6-7. The alignment nub 63 is designed to align with and abut or be received into a corresponding alignment hole 62 of the shell 61. Similarly, the raised notch 50 along barrel 35 outer surface aligns and fits within grooves 52 of shells 61 inner wall 60, thus properly aligning the outer surface of barrel 35 and inner wall 60 of shell 61. While it is important to prevent the barrel 35 from become out of alignment, an expansion gap may exist between the outer diameter of the barrel 35 and inner wall 60 of the shell 61 to permit certain expansion that may occur during use. For example, as seen in FIG. 8 an expansion gap 72 may exist towards front end of barrel. The purpose for an expansion gap 72 is to allow the barrel 35 to expand or stretch a predetermined amount during injections but prevent the barrel 35 from overexpansion or overstretching to the point of failure. Therefore the size of expansion gap 72 may vary depending on how much room the syringe barrel 35 needs to expand or stretch but yet still be reinforced by shell 61 to prevent failure.

Figure 9:
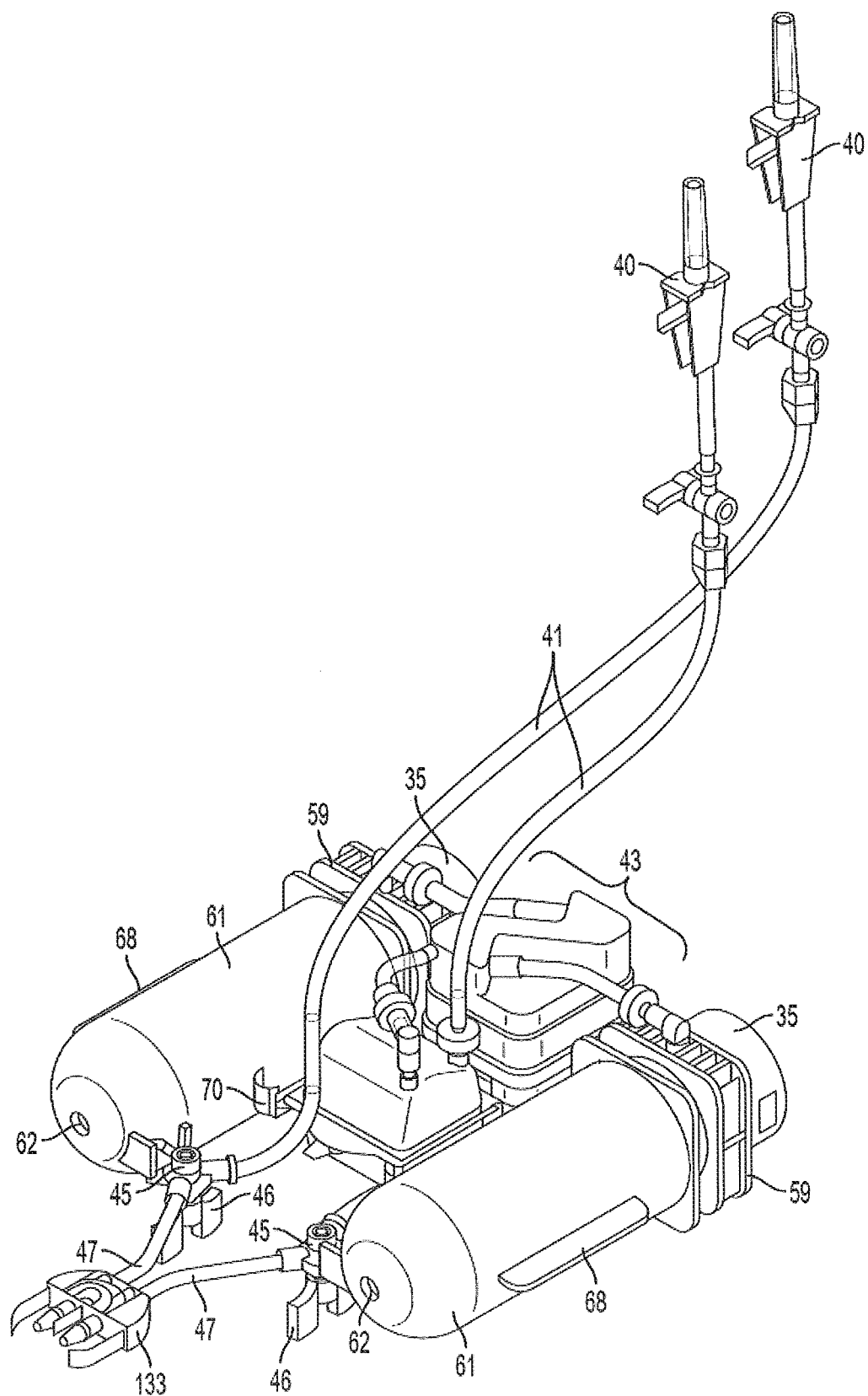
FIG. 9 is a side perspective view of the multi-use subassembly.
Figure 10:
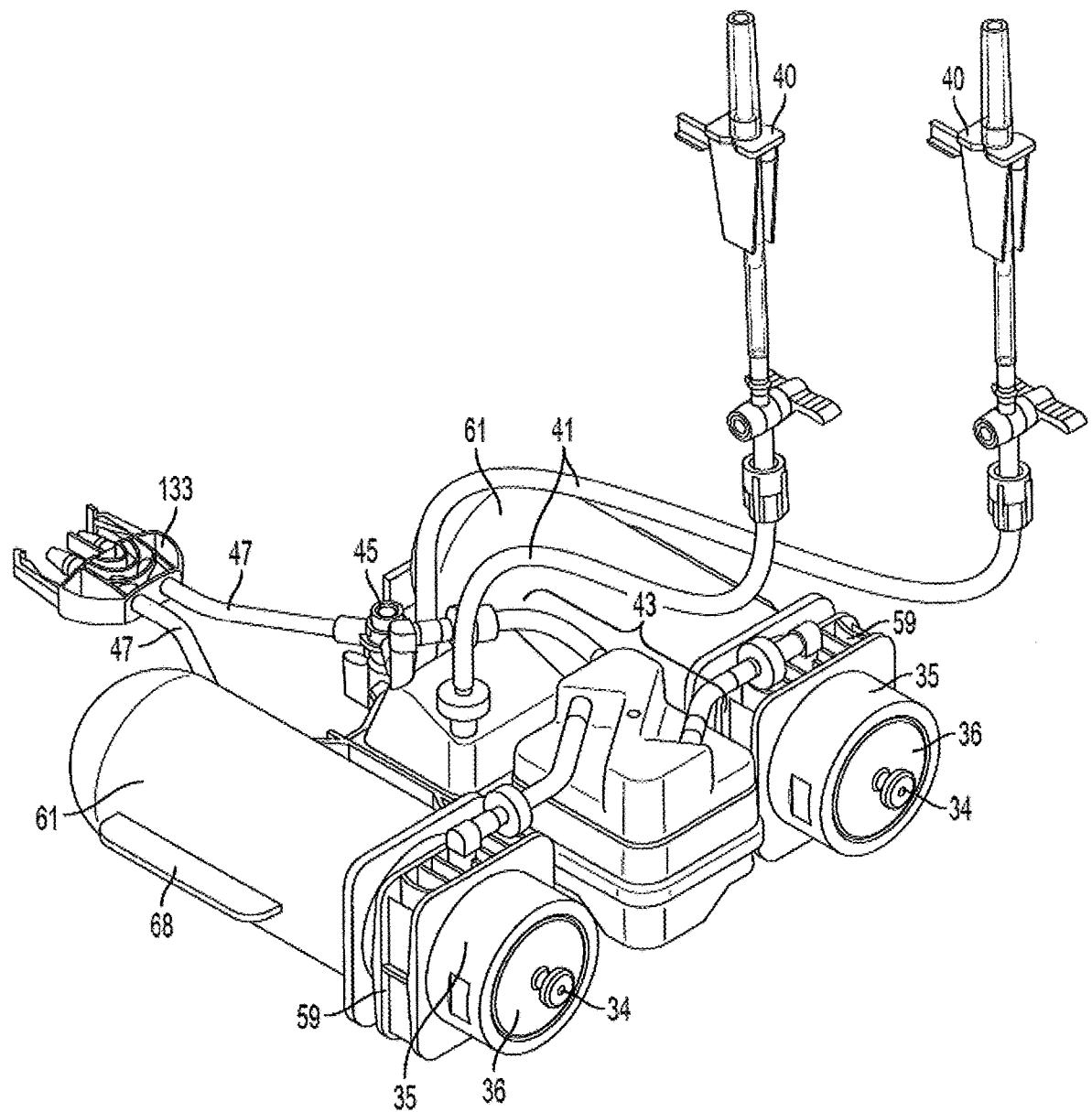
FIG. 10 is a rear perspective view of the multi-use subassembly.
Figure 11:
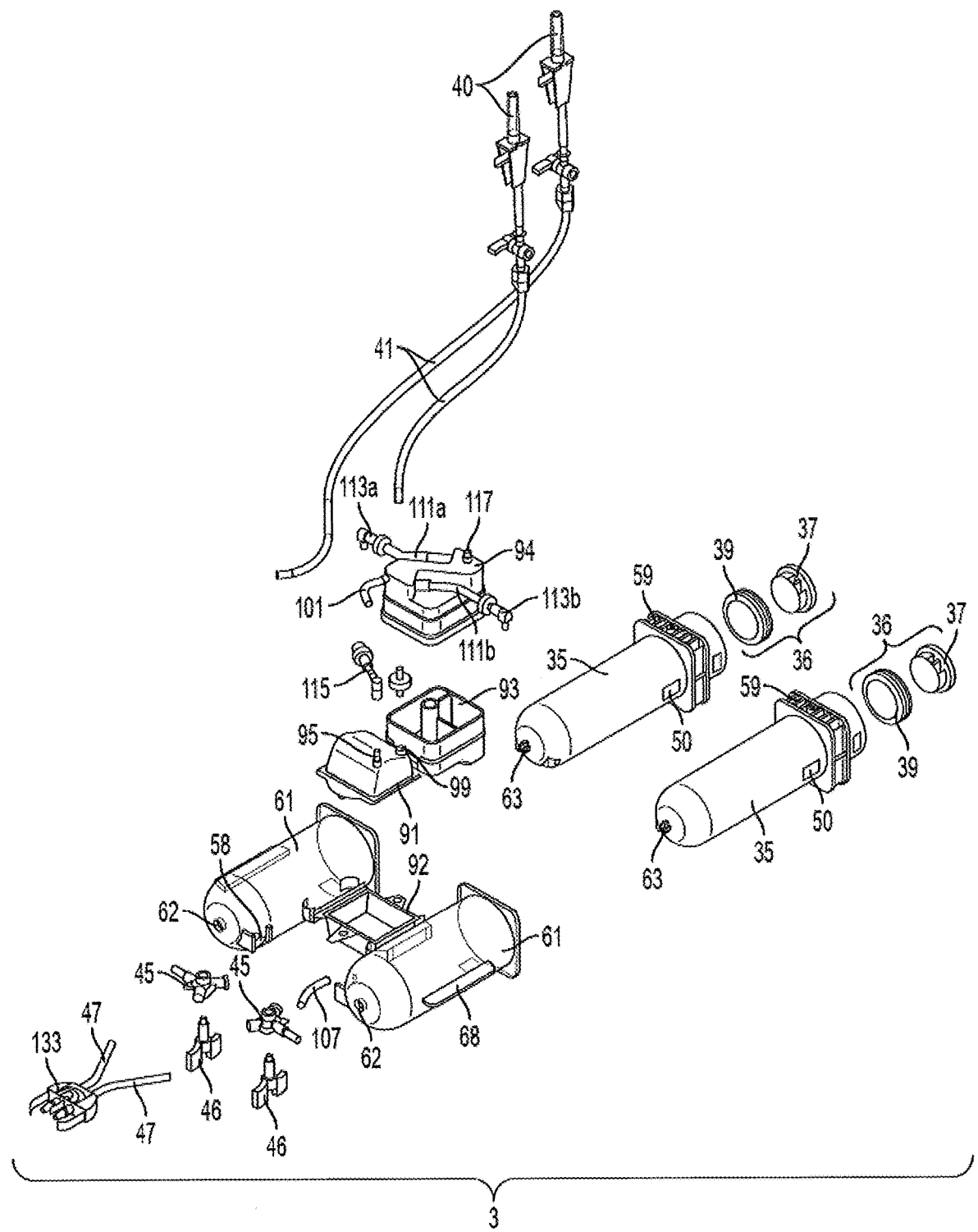
FIG. 11 is an exploded perspective view of the multi-use subassembly.

Referring to FIGS. 9-11, one embodiment of the entire multi-use subassembly 3 with all of its components is shown. The multi-use subassembly 3 of this embodiment may comprise two syringe barrels 35 securely enclosed within an outer protective shell 61, a venting system 43, automated valves 45, and tubing lines 47, 41. The ridges 59 are not enclosed by the shell 61 because the ridges 59 may attach to the rear securement means 79, as described in more detail below. The automated valves 45 fluidly connect the barrels 35 to the fill tubing 41 or connection tube 107 and injection tubing 47. The fill tubing 41, connection tube 107 and injection tubing 47 may incorporate flexible, large inner diameter high pressure tubing to enable user to visualize any trapped air in tubing sets and achieve desired high pressure flow rates while maintaining flexibility. The fill tube 41 may contain bag spikes 40 as known in the art to fluidly connect the fill tubes 41 with the fluid sources. Injection tubing 47 may be fluidly connect the barrels 35 to the fitting 133. Dedicated fluid lines may minimize fluid waste and injection fluid lag. The tubing lines 41, 47 may be either clear or have a specific color to represent the type of fluid present. For example, the tube carrying saline may have a blue line or tint along its length so the user may easily visualize the tubing line corresponding to the delivery of saline.

As seen in FIG. 11, plunger 36 may comprise of a plunger body 37, cover 39 and securement nub 34. As described in more detail below, the securement nub 34 along the rear wall of body 37 may be used when securing the multi-use subassembly 3 to the injector housing 13. Plunger cover 39 may be sized so it can freely slide along inner wall of barrel 35 while all sides of cover 39 converge on or abut against the inner wall of barrel 35.

As seen in FIG. 12-15, the multi-use subassembly 3 may include specially designed automated valves 45. Automated valve 45 may be a Y-shaped rotary valve. The automated valves 45 may include a valve stem 42, valve tab 46, and may be comprised of three different channel elements: a fill channel 44, an injection channel 38, and a barrel channel 48. Valve stem 42 is inserted and securely attached to first port 55 of the barrel 35. Stem 42 may be secured by adhesive or other known methods in the art. The barrel channel 48 connects to first port 55 of barrel 35 via valve stem 42. The fill channel 44 of one barrel 35 may be connected to tubing line 41 which may be in fluid connection to fluid source 23 (saline, contrast, and other fluid being injected) or a fill chamber 90. For example, barrel 35 containing saline may have fill channel 44 fluidly connected to tubing line 41 which is in direct fluid communication with saline source. Alternatively, the fill channel 44 of other barrel 35, such as barrel 35 containing contrast fluid, may be in fluid communication with connection tube 107 which in turn is in fluid communication with fill chamber outlet port 97, as described in more detail below. The injection channel 39 may be connected to injection tubing 47.

The valve 45 must be able to withstand high pressures during injection of fluids. The Y-shaped valve 45 as shown may have angles up to one hundred and twenty degrees between the fill channel 44, injection channel 38, and barrel channel 48. This valve 45 design is an improvement upon valves commonly used in the art, which may be known as "T-valves" or "90 degree valves" which have ports separated by only ninety degrees. An advantage of valve 45 is to maximize the ceiling surface area between fluid paths over a traditional ninety degree valve. For example, the Y-shaped valve 45 is an increase of the ceiling surface area between first port barrel channel 48 and injection channel 38 and between fill channel 44 and barrel channel 48 because each port is separated by at least one hundred and twenty degrees. This greater ceiling surface provides superior protection against valve 45 failure during high pressure injections because stress on the valve may be more evenly dispersed. Also, unlike a traditional T-shaped or ninety degree valve, which may require fluid to take a sharp ninety degree turn during an injection, the Y-shaped valve 45 may provide for a less severe and smoother transition or turn for fluid to travel. Thus, Y-shaped valve 45 has less of a chance for leaking, cracking, or failure during high pressure fluid flow because stress on valve 45 is more evenly distributed and flow of fluid is less turbulent.

Figure 13:
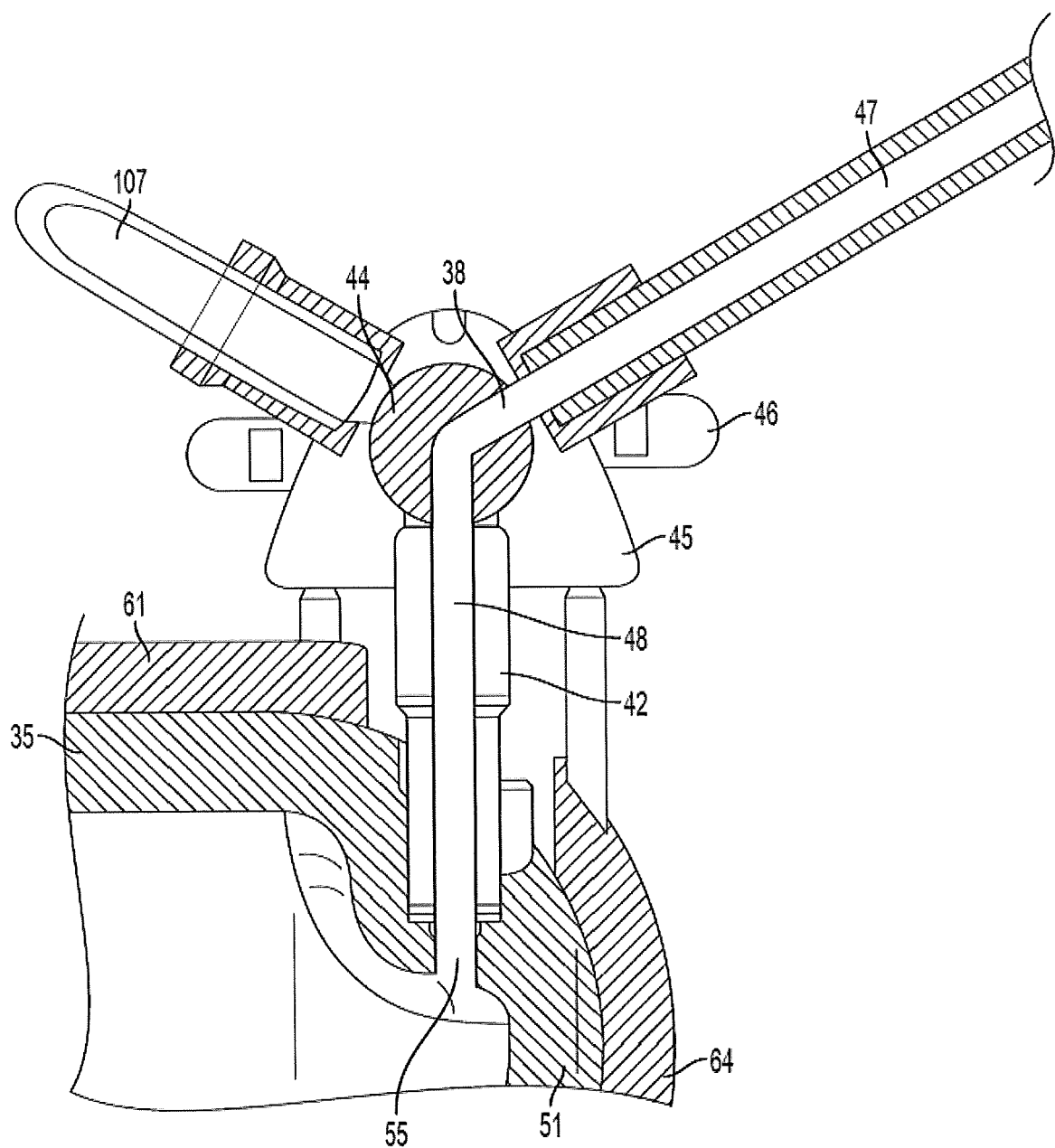
FIG. 13 is a partial top cross-sectional view of the automated valve in the inject position.
Figure 14:
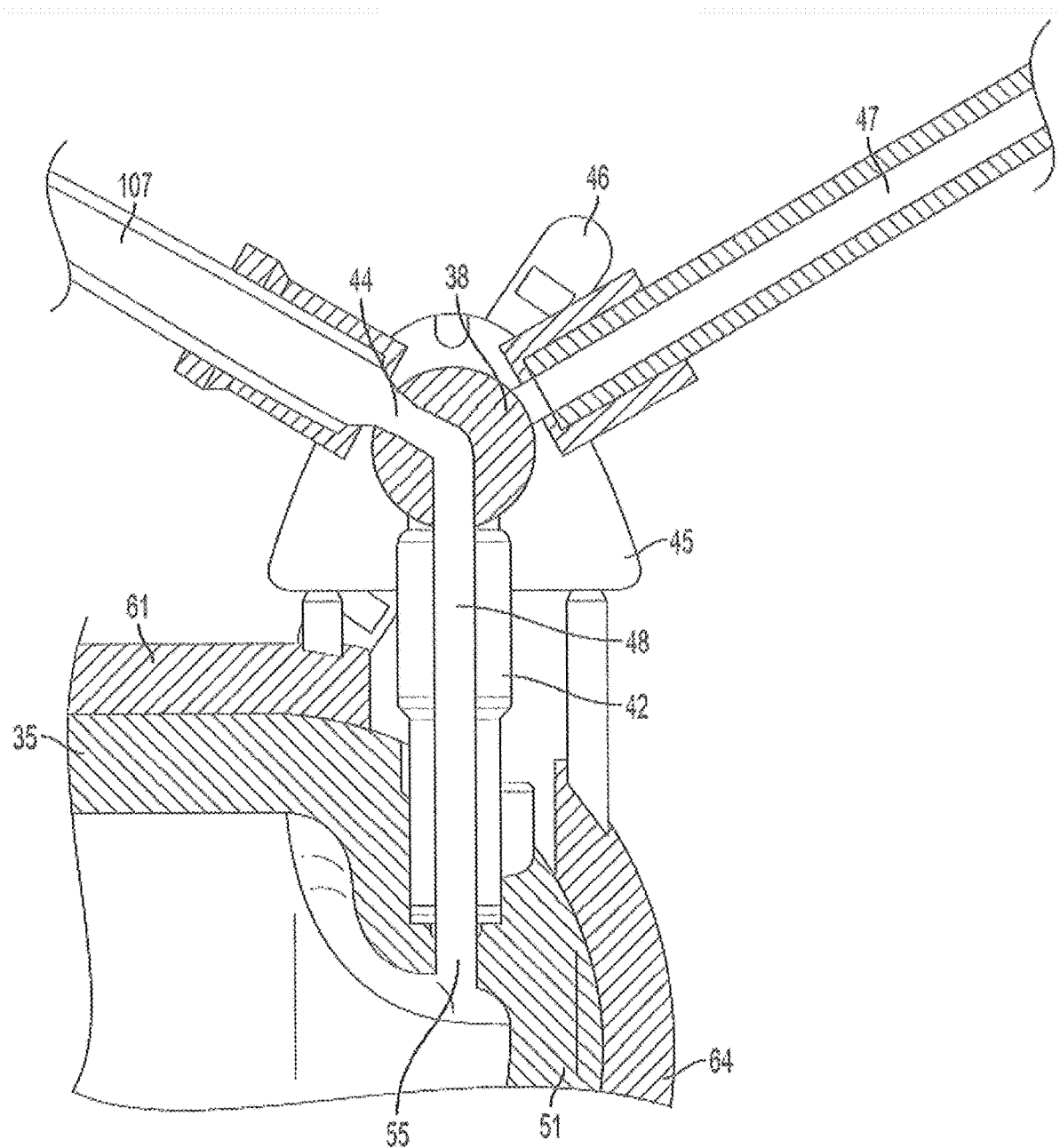
FIG. 14 is a partial top cross-sectional view of the automated valve in fill or purge position.
Figure 15:
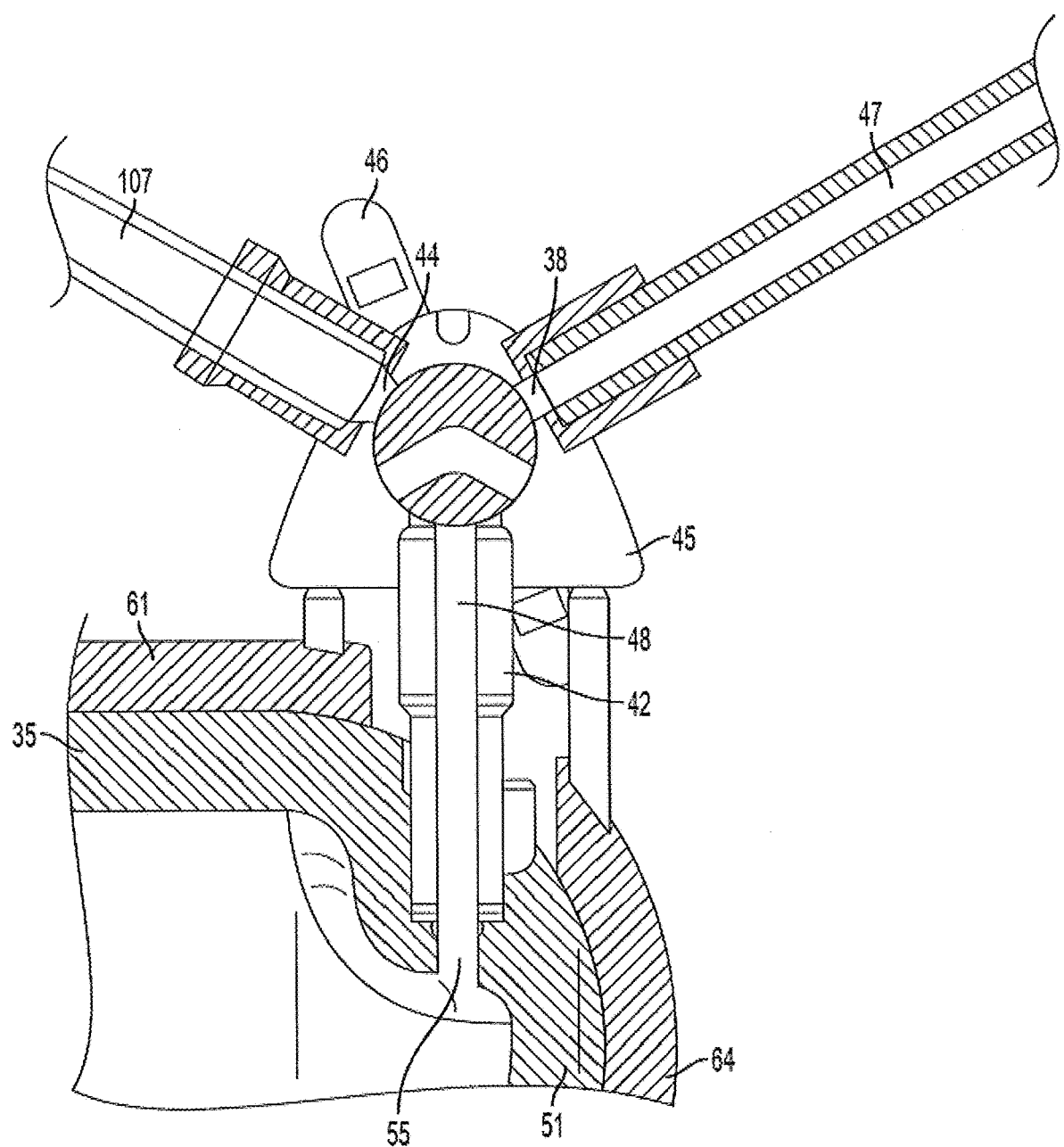
FIG. 15 is a partial top cross-sectional view of the automated valve in a closed position.

The valve 45 has an injection setting, a fill setting, or a closed setting. The movement of the tab 46 controls changing between the settings. The tab 46 is controlled by the valve actuator 16 (see FIG. 3a), which in turn is controlled by the user interface 7. As the user selects a certain function on the interface 7 this causes the valve actuator 16 to automatically rotate. As the actuator 16 rotates this causes the tab 46 to simultaneously rotate, thereby changing the valve setting. As seen in FIG. 13, the valve 45 is shown in the injection position with open fluid communication between the barrel channel 48 and the injection channel 38. The injection position allows for fluid to be injected into the patient by establishing a flow path from the barrel 35 through the injection channel 48 to the injection tubing 47 which is in fluid communication with fitting and single-use subassembly. As seen in FIG. 14, the valve 45 is in the fill position with open fluid communication between the fill channel 44 and barrel chamber. The fill position is used to fill the barrel chamber by allowing fluid to travel from the fluid source 23 or fill chamber 90 into the barrel 35 and may also be used during venting. As seen in FIG. 15, the valve 45 is in a closed position with no open fluid communication between any of the ports. A closed position may be used when the single-use subassembly needs to be changed or when injector is shut down for an extended time.

Referring to FIGS. 11 and 16-18, the multi-use subassembly also includes a venting system 43 used to purge barrel 35 of trapped or unwanted air. The injection system must be primed before use to avoid any air being injected into the patient. The priming stage includes filling the syringe barrel 35 of the multi-use subassembly 3 with fluid from the fluid reservoirs and then filling the single-use subassembly with fluid. During priming air may become trapped within the syringe barrel 35 or in any the fluid lines, therefore it is important to remove this air through the venting system 43 prior to injecting fluid into the patient.

The venting system 43 comprises a fill chamber having a top half 91 and bottom half 92, the fill chamber may have several ports including: an inlet port 99, an outlet port 97, and an overflow port 95. Venting system may also include a waste chamber 96 having a top half 94 and bottom half 93, and several ports including a first inlet port 101, a second inlet port 103, a third inlet port 105, and an outlet port 117.

The fill chamber may be used to fill one of the syringe barrels 35 with fluid, such as contrast, and prevent back pressure buildup within the fluid source. It is common for contrast fluid sources to be packaged in hard glass medical grade containers that may be susceptible to a buildup of reverse or negative pressure leading to leaks or cracking in the fluid connection. For example, if the barrel 35 containing contrast was in direct fluid communication with contrast source then during the purging sequence pressure from the syringe barrel 35 may build and travel back up stream towards the contrast fluid source. Since the contrast fluid source may be a hard glass container that does not allow for expansion, any buildup of negative pressure may lead to leaks or damaging the fluid connection between the injector and contrast source. Therefore, the fill chamber 91 acts as a pressure release or pressure buffer to prevent the unwanted pressure buildup within the contrast fluid source. Conversely, the saline fluid source is commonly packaged in a flexible medical grade pouch or bag that is expandable and able to withstand reverse or negative pressure without causing leakage or failure in fluid connections. Therefore, it is possible for the barrel 35 containing saline to be in direct fluid communication with saline source because any negative pressure during purging will simply expand the flexible saline bag and not impact the connections between saline source and injector.

Figure 17:
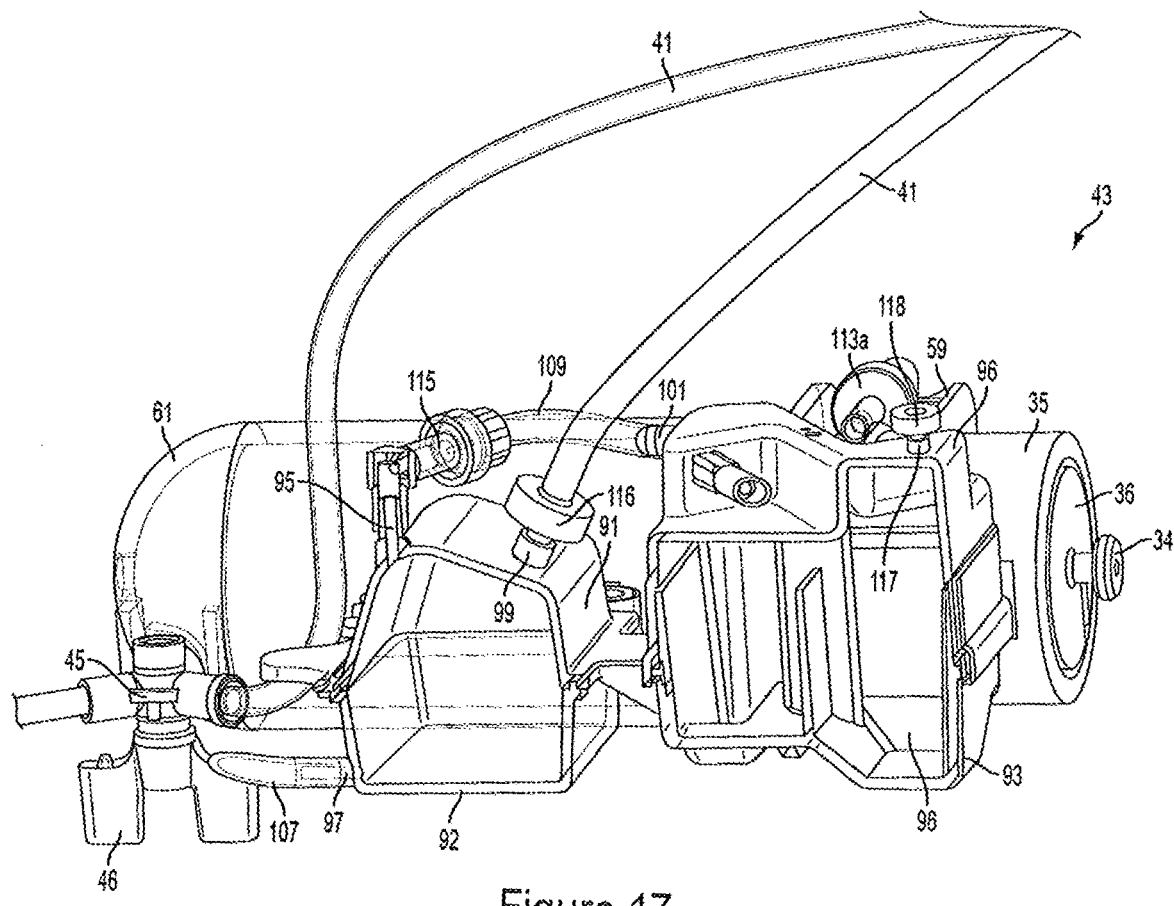
FIG. 17 is a cross-sectional view of the multi-use subassembly highlighting the venting system.

To more clearly understand the function of the fill chamber the process of filling the barrel 35 with contrast will now be described in detail. As seen in FIG. 17, the fill line 41 for fluid source, preferably contrast, is connected to the fill chamber inlet port 99 having a one-way check valve 116. As the plunger 36 of the contrast barrel 35 retracts back during the venting sequence, as described in more detail below, negative pressure is created within the barrel 35. The negative pressure draws and pulls the contrast from its source along the fill tubing 41 before passing through the fill one-way check valve 116 and into the fill chamber 92. The negative pressure within barrel 35 will pull or force contrast collected within fill chamber to pass through the fill chamber outlet port 97, through a connection tube 107 into the valve fill channel 45 and then through first port 55 into the barrel 35, as seen in FIG. 12. Referring back to FIG. 17, the inlet port 99 may have a standard one-way check valve 116 preventing air from exiting the inlet port 99 and traveling back up line towards the contrast source, thereby preventing the unwanted buildup of negative pressure within the contrast fluid source. During venting it may be necessary for any excess contrast in the fill chamber 92 to be forced through the fill chamber overflow port 95 and one-way check valve 115 then along the overflow connection tube 109 and into the first inlet port 101 of waste chamber 96. The reason the excess contrast will back flow through the fill chamber overflow port 95 rather than through the fill line 41 to the contrast fluid source is because the one-way check valve 116 prevents reverse flow from the fill chamber 92 to fluid sources, thereby protecting against additional waste of the entire fluid source.

Figure 16:
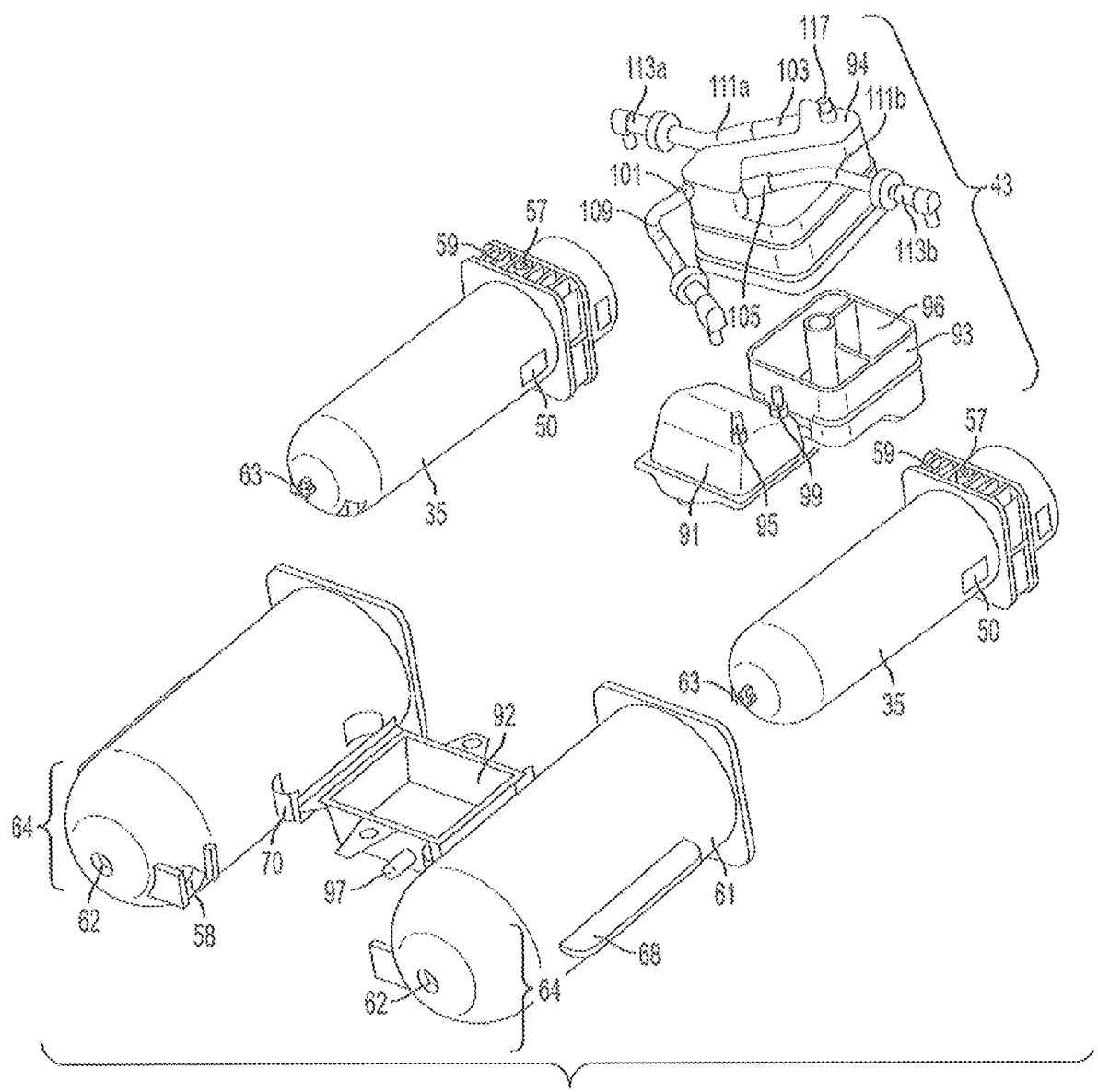
FIG. 16 is an exploded view of the multi-use subassembly highlighting the venting system.

The waste chamber 96 is intended to allow air to escape from the barrel while also collecting any saline, contrast, or other fluid that is removed during the purging process. If the injector 1 is tilted at a range of 5-40 degrees relative to the horizontal axis of the base, as shown in FIG. 2, any air remaining within barrel will be forced to the top rear of the syringe barrel 35, near the location of the second port 57. Referring to FIG. 16, air is forced through the second port 57 of barrel 35, through a waste one-way check valve 113(a), 113(b) along waste connection tubing 111(a), 111(b) and then into either the second 103 or third 105 waste chamber inlet ports. Then excess air passes through the waste chamber outlet port 117 which is open to atmosphere. The waste chamber outlet port 117 may have a standard one-way check valve 118, as shown in FIG. 17, to only allow air to escape from the waste chamber 96 and prevent unwanted air from entering the system through the outlet port 117.

Figure 18:
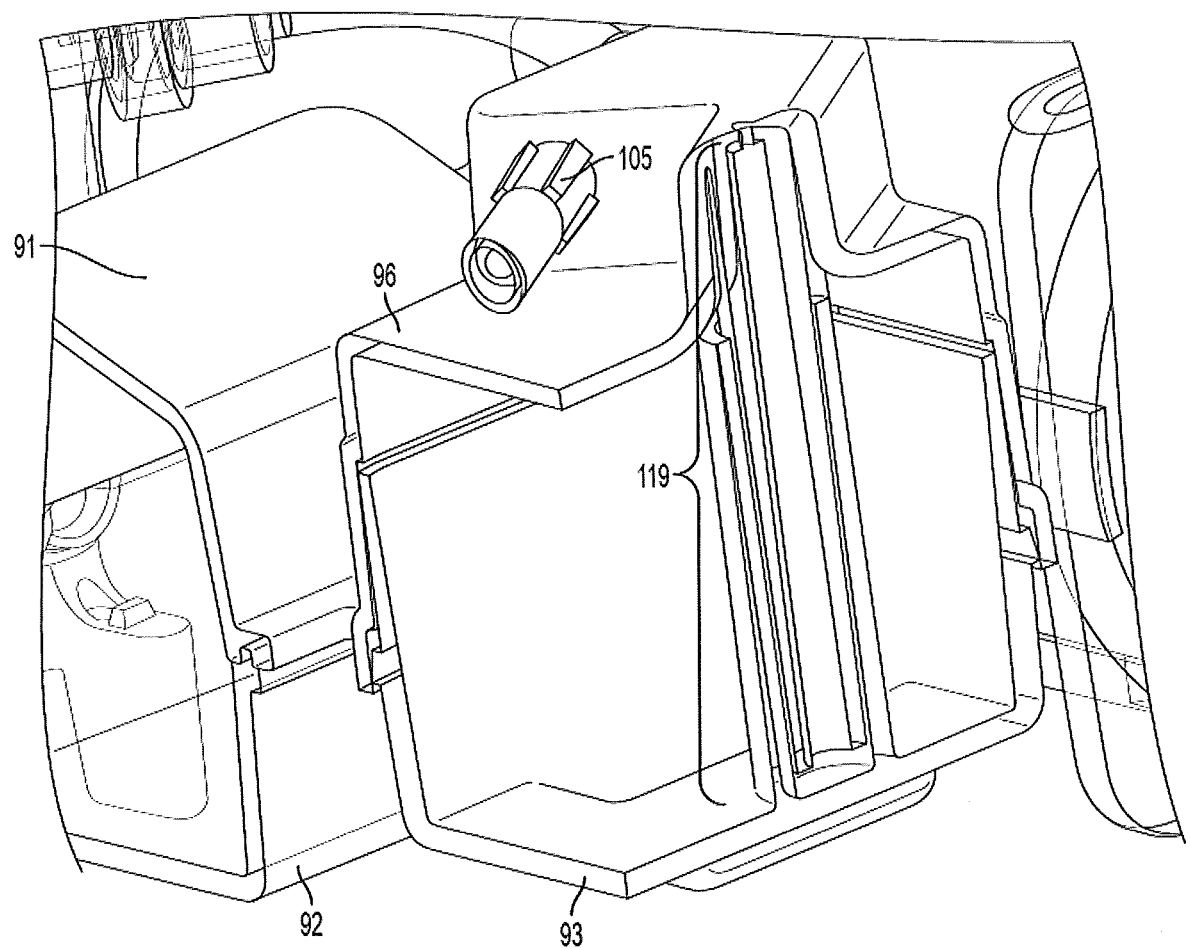
FIG. 18 is a partial perspective cross-sectional view of the venting system.

The waste chamber 96 may contain multiple fluid columns 119 to increase the total surface area of the waste chamber 96, as seen in FIG. 18. The purpose of the multiple fluid columns 119 is to increase the overall surface area of the waste chamber 96 while thereby increasing the amount of fluid the waste chamber 96 is able to hold without increasing the overall size of the waste chamber 96. The fluid columns 119 increase overall distance the fluid must travel before it enters the waste chamber 96, thereby increasing total waste capacity without increasing the size of the waste chamber 96. As fluid enters the waste chamber it must travel up and down each fluid column 119 before it actually enters the chamber and collects along the bottom surface 93.

Figure 19:
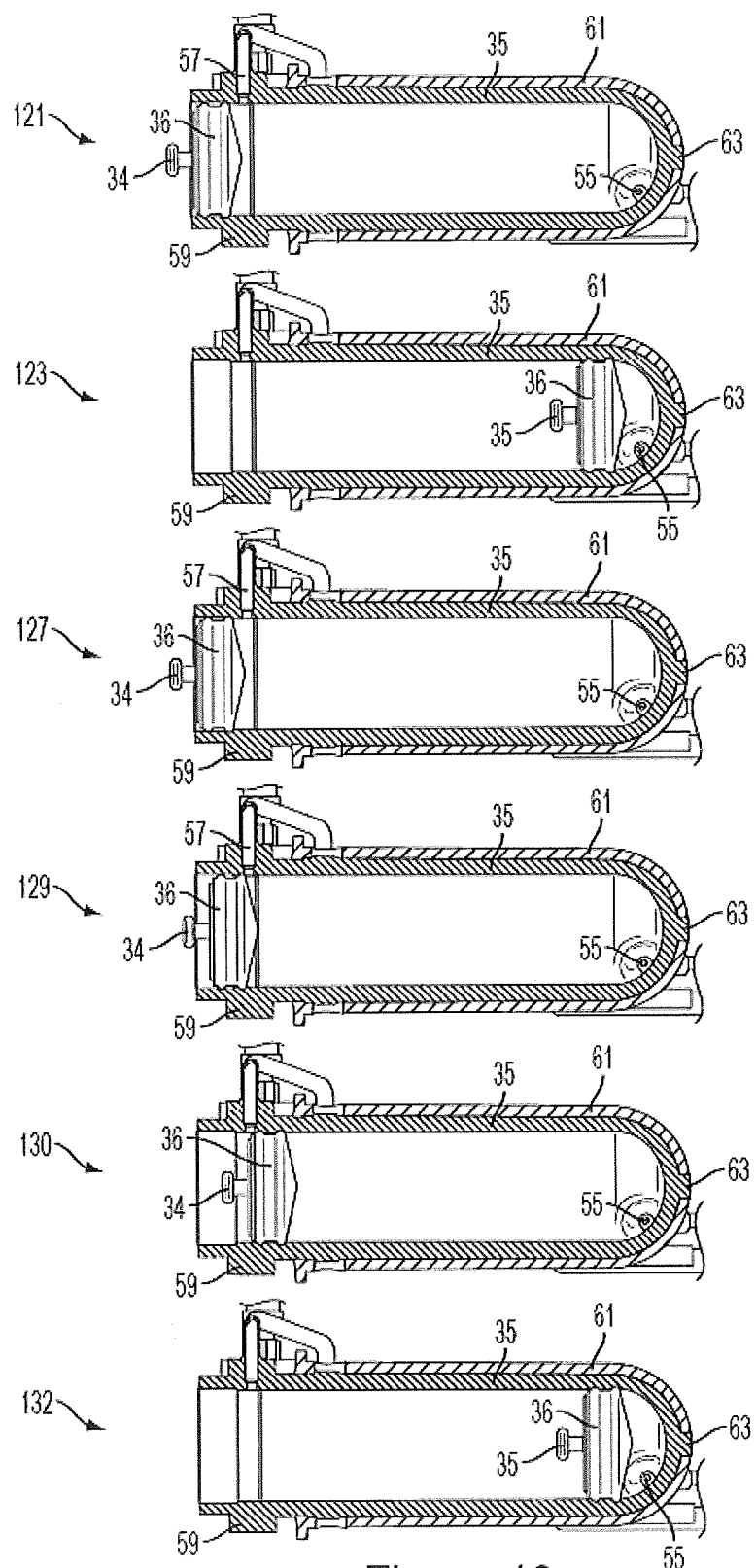
FIG. 19 are partial side cross-sectional views of syringe barrel and plunger position during venting.

During the automated injection sequence the system may stop plunger before it reaches the front end 51 of barrel 35, thereby leaving a reservoir of predetermined volume of fluid (5-10 mL) within barrel chamber captured between the plunger and the front end 51 of the barrel 35, as seen in step 123 of FIG. 19. The purpose of this reservoir of predetermined volume of fluid is if any excess air is trapped inside barrel chamber after purging the air will be forced along the top wall 56 of the barrel 35 because injector housing 13 may be tilted at a 5-40 degree angle along the horizontal axis.

As seen in FIG. 19, the method of injecting fluid into a hollow anatomical structure using the injector system disclosed herein may include several steps. The movement of air or fluid inside the barrel 35 chamber is controlled by the movement of the plunger 36. The movement of the plunger 36 may be controlled by the injector ram. For example, the plunger securement nub 34 may be securely attached to the rear support means and in turn the injector ram, as described in more detail below, so plunger movement is controlled as injector ram advances forward or retracts back. The purging sequence 121 may start with plunger 36 at proximal most end of barrel 35 and the valve 45 is rotated into the inject position, as seen in FIG. 13, so the barrel channel 48 is in fluid communication with the injection channel 38. The barrels 35 may be purged prior to being connected to the procedure catheter. Next, plunger 36 is pushed forward 123 towards front of barrel 35 causing any trapped air in barrel 35 to be expelled through first port 55 and through valve 45 and tubing 47 and then fitting 133, as also seen in FIG. 12, which is open to atmosphere. Next, the valve 45 is rotated to fill position, as seen in FIG. 14, so the barrel channel 48 is in fluid communication with the fill channel 44. Plunger 36 is then retracted to a first purge position 127 which is a first selected distance proximal from the second port 57. While plunger 36 is in first purge position 127 fluid may be filling the syringe barrel 35 through port 55. The rate at which fluid fills syringe barrel 35 depends on the fluid's viscosity, for example contrast may take a longer time to fill syringe barrel 35 than saline due to contrast's higher viscosity. Once fluid has filled the syringe barrel 35 the plunger 36 may be advanced forward slightly to a second purge position 129 a second selected distance proximal from second port 57. While plunger 36 is in second purge position 129 any trapped air still remaining in barrel 35 will be forced out of barrel 35 through second port 57. After all air has been removed the valve 45 is rotated into the inject position, as seen in FIG. 13, and the plunger 36 is advanced distally beyond the second port 57 to the inject position 130. During injection, plunger 36 is advanced distally causing fluid to be advanced through port 55 into lines 47, as show in FIG. 12. After injection is complete 132 the user may select to either refill the barrel 35 or put the injector in standby mode. If the user elects to refill the barrel 35 then the valve 45 may be rotated to fill position, as seen in FIG. 14, and injector would repeat fill and purge steps 123, 127, 129 and 130. Alternatively, if user elects to put injector in standby mode then valve 45 may be moved to closed or off position, as seen in FIG. 15. Standby mode may be used between procedures of multiple patients or if the injector is not going to be used for an extended period of time.

As seen in FIGS. 20-23, the injector system 1 may comprise a rear barrel support means 79. The purpose of the rear barrel support means 79 is to securely attach and hold the securement ridge 59 of barrel 35 to the injector housing 13. The rear barrel support means 79 may comprise multiple support flanges 85, 83, a plunger lock means 88, and a top flange (not shown). The rear barrel support means 79 may be part of the injector housing 13 and adjacent to the injector rams 15.

The injector rams 15 may be a mechanism capable of advancing and withdrawing the plunger inside the barrel chamber. The injector rams 15 may be mechanical arms or pistons that push and retract the plunger 36 of barrel 35. For example, in this embodiment the injector rams 15 may be motorized pistons that are advanced forward toward the front face of the barrel during an injection and are withdrawn back towards rear support means 79 during a fill or purge sequence. The movement of the injector rams 15 may be controlled by electronic signals sent from either the user interface or the hand controller. For example, the user may input injection parameters into the user interface or choose different selections on hand controller and then an electronic signal is sent from user interface or hand controller to the injector rams 15. Depending on the type of electronic signal sent the movement of the injector rams 15 may be either forward or rearward. The injector rams 15 may include a sensor 87 to measure how much force or pressure is being transferred to the plunger 36 as the plunger 36 is moved forward and rearward. The ram sensor 87 may measure the amount of force exerted onto the barrel 35 by the rams 15. The ram sensor 87 may be comprised of a known sensor in the art. This sensor 87 is in electronic communication with the user interface 7. The interface 7 uses the information from sensor 87 to measure at what pressure or force the injector is operating and ensuring this is correctly correlated with the user inputs.

Figure 20:
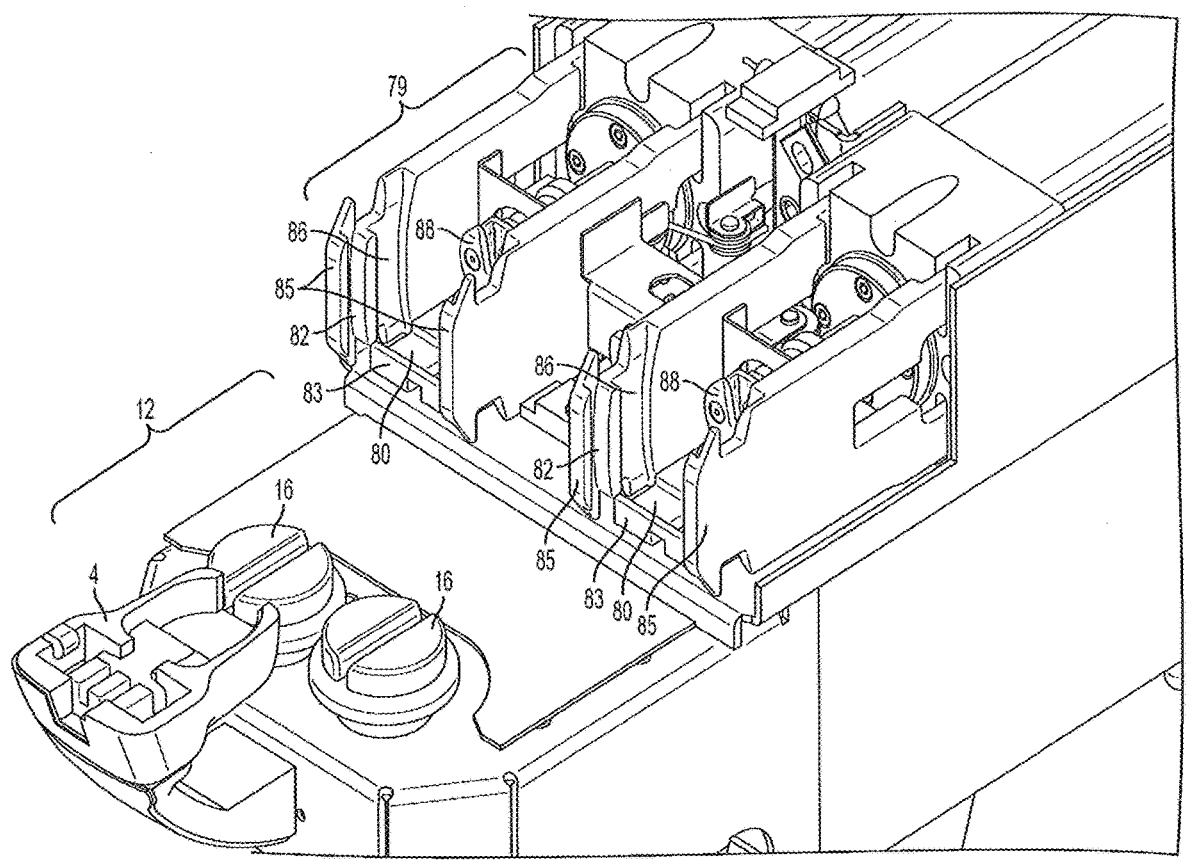
FIG. 20 is a side perspective view of the injector housing, specifically the syringe support means.
Figure 21:
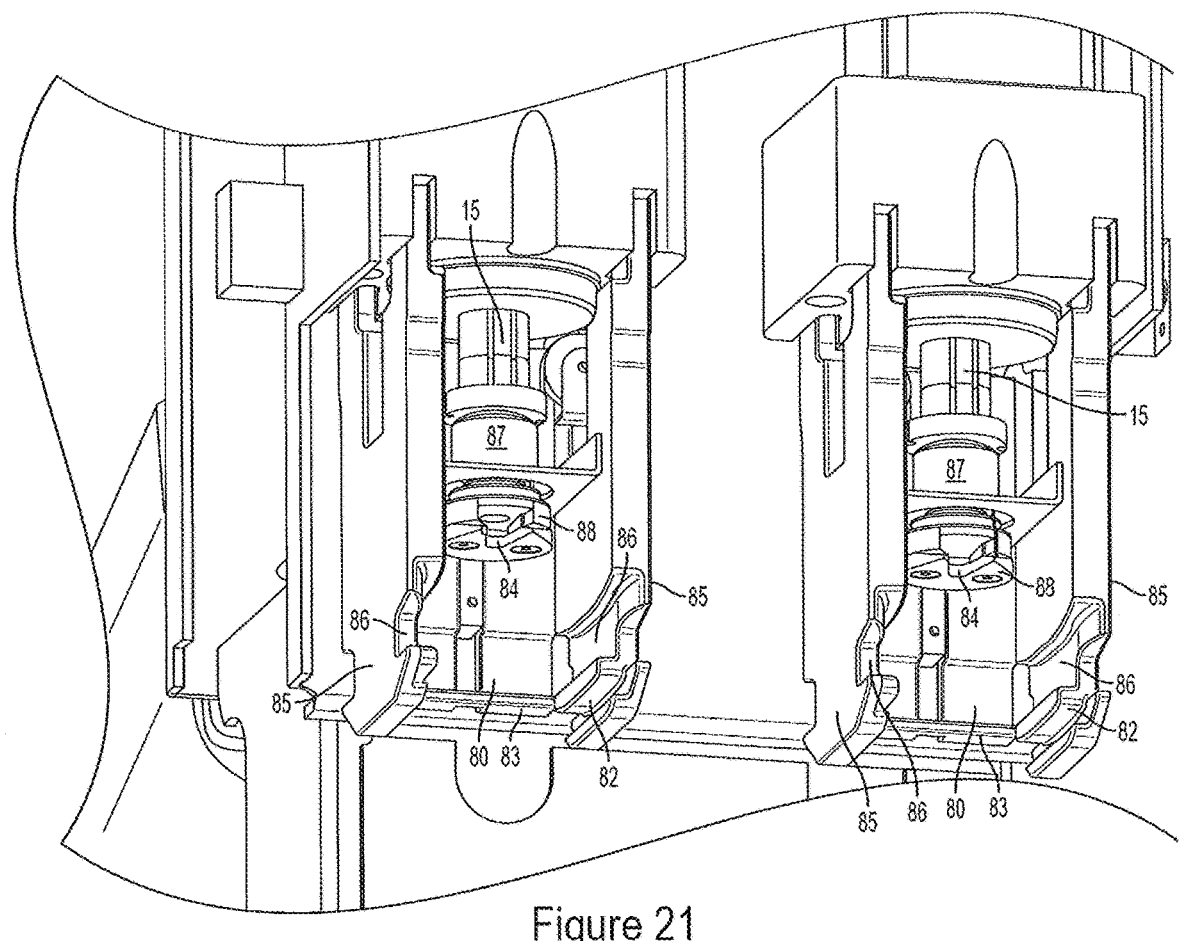
FIG. 21 is a top perspective view of the injector housing, specifically the syringe support means.

The support flanges may include, but not limited to, a top flange (not shown), at least one bottom flange 83, and at least two side flanges 85. If a top flange (not shown) is used, it may be connected to support means 79 via a hinge so during setup the top flange is able to be lifted up and away from the side flanges 85 and bottom flange 83. The flanges 83, 85 are intended to be shaped and size to securely enclose the securement ridge 59 of barrel 35, as shown in FIG. 20. The flanges 83, 85 may have a barrel groove 86 and a shell groove 82. Grooves 82, 86 may consist of an indent or step along the ends of the flanges 83, 85. The sides of the securement ridge 59 may align with and be slid into the ridge grooves 86 of the side flanges 85. Additionally, the shell 61 may have a rear ridge 28 that securely fits within shell groove 82. The bottom flange 83 may also have a groove 80 that aligns with the bottom of the securement ridge 59. In addition to flanges for support, the rear barrel support means 79 may also include a plunger lock means 88. The plunger lock means 88 is intended to securely attach to the plunger securement nub 34 on the rear end of the plunger body 37. The lock means 88 may have a notch 84 that is shaped to receive the securement nub 34.

Figure 22:
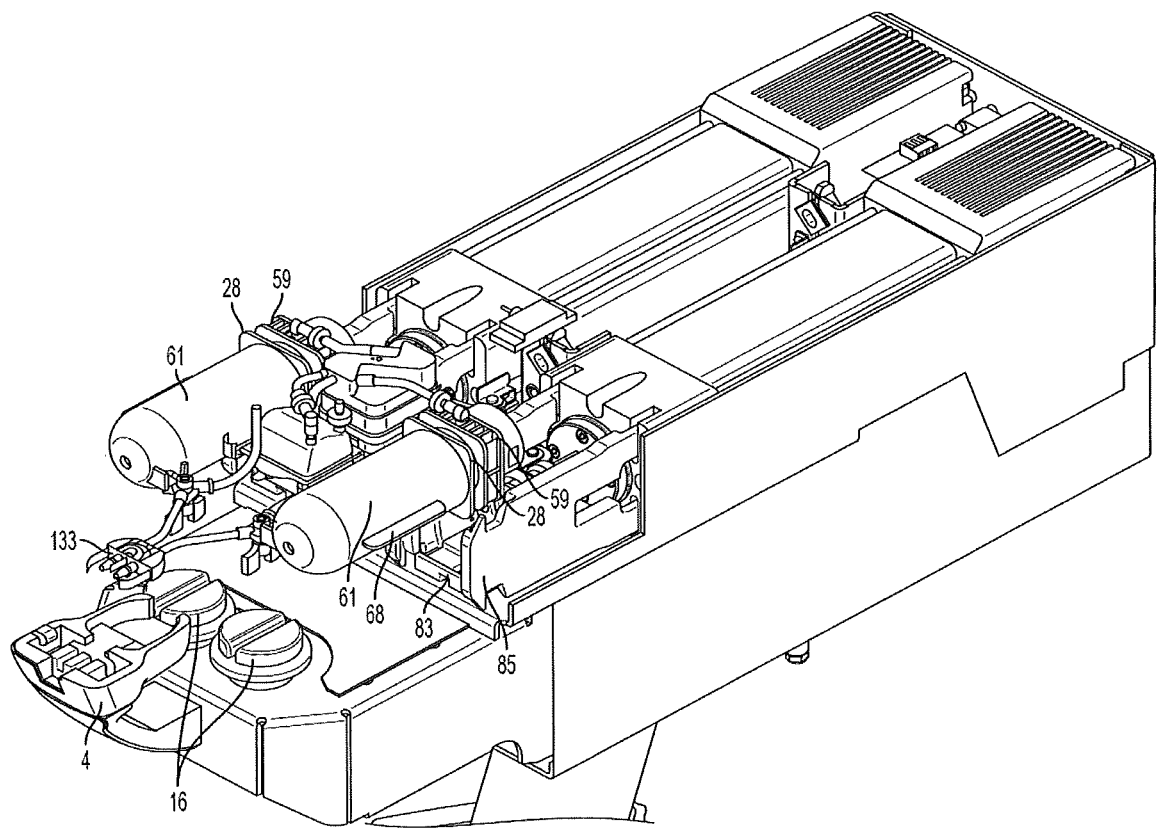
FIG. 22 is a side perspective view of the injector housing, specifically the syringe support means and the multi-use subassembly.
Figure 23:
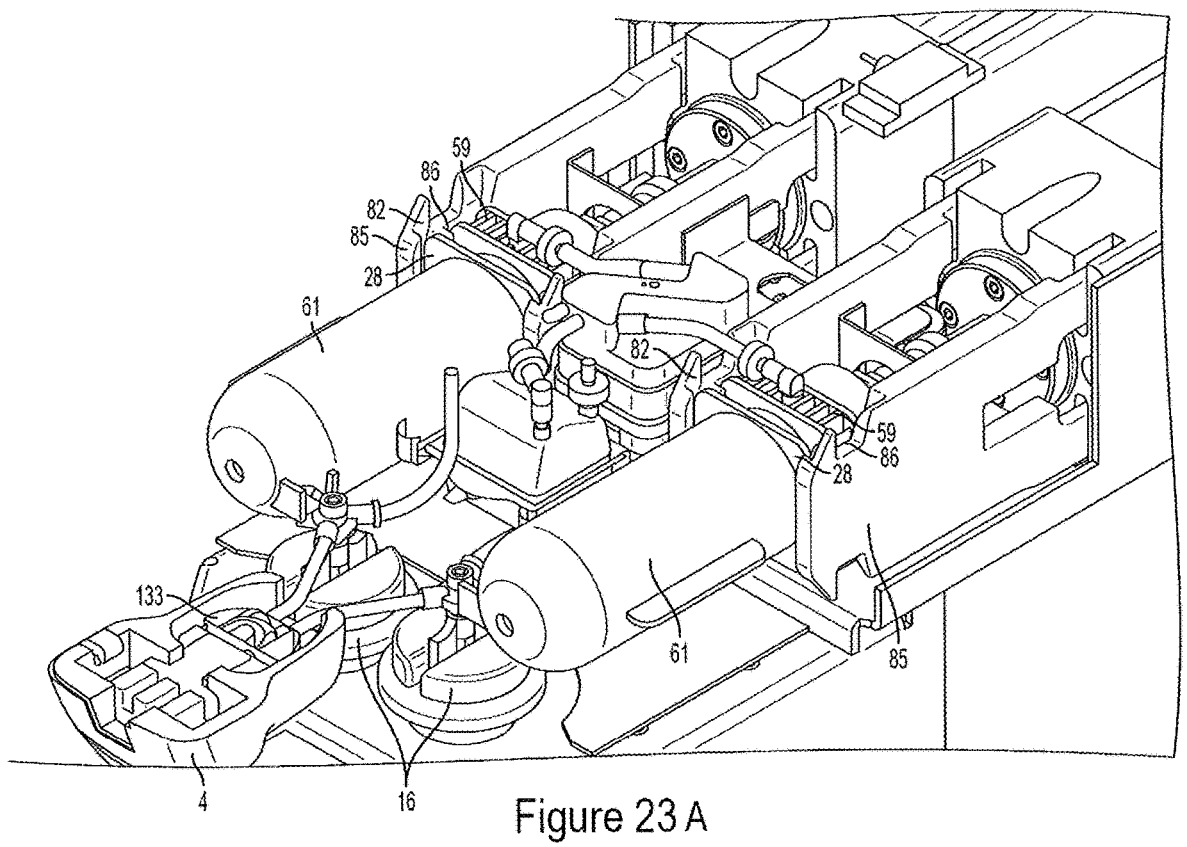
FIG. 23A is a side perspective view of the injector housing, specifically the syringe support means and the multi-use subassembly.
FIG. 23B is a side perspective view of the injector housing, specifically the syringe support means and the multi-use subassembly with lift support.
Figure 23:
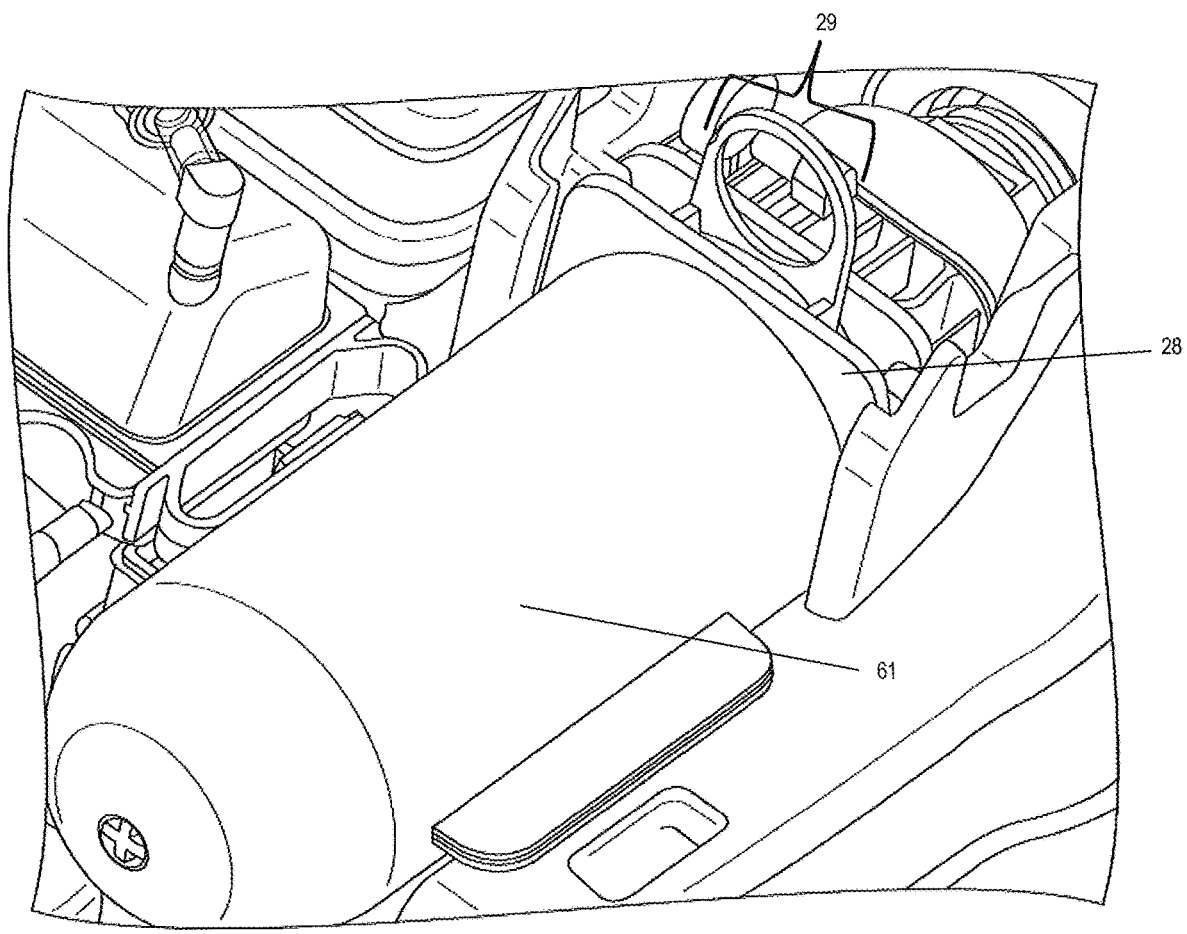

As seen in FIG. 22-23A, the rear support means 79 is intended to simplify system setup. The system allows the user to simply align the securement ridge 59 over the rear barrel support means 79 and then push the multi-use subassembly 3 in place. First, the user may hold onto the side tabs 68 of shell 61 and align the securement ridge 59 with ridge grooved 86 and shell ridge 28 with shell groove 82 of side flanges 85. Next, the multi-use subassembly may be push downward to align the plunger securement nub 34 with the notch 84 of the plunger lock means 88. Finally, the user may continue to push down on the multi-use subassembly 3 until the bottom side of the securement ridge 59 is aligned with the grooved 80 of bottom flange 83. An advantage of the rear support means is that once the user aligns the securement ridge 59 with the rear barrel support means 79 all of the other components of the multi-use subassembly 3 are automatically align into proper position making the setup process faster and overall injector more user friendly. For example, once the securement ridge 59 is over the rear barrel support means 79 the valve tabs 46 will also be aligned over the valve actuator 16. Upon proper placement of the multi-use subassembly 3 into the rear barrel support means 79 the user may hear an audio feedback, such as a sound or a "click", or have a tactile feedback response. After multi-use subassembly 3 has been positioned inside the rear barrel support means 79 the user may push down or close the top flange (not shown) or the cover 6, thereby locking and securing the multi-use subassembly 3 to the injector.

As seen in FIG. 23B, the shell ridge 28 may further comprise a lift support 29. The lift support 29 provides the user with a means for lifting the shell 61 from the injector housing. For example, after a high powered injection the shell 61 may be difficult to remove and replace. Therefore, the life support 29 may provide the user with an additional area to grasp onto and assist the user with faster removal of the shell. The lift support 29 may be a separate piece of material that is securely attached to the shell ridge 28 by ordinary means known in the art. The lift support 29 may take the form of a ring, key hole, circle, or other shape that allows a user to easily grasp onto.

Referring now to FIG. 24-27, the multi-use subassembly 3 and single-use subassembly 5 may be connected by a specially designed fitting 133. It is known in the art to use standard luer type connectors for injection systems. Such standard luer connections require the user to twist or rotate a luer at each connection point. The purpose of the fitting 133 for this injection system is to allow the user to quickly connect the multi-use assembly to the single-use assembly. The connection makes the setup simpler, more reliable, and decreases overall setup time. Rather than using standard luer type connection the injection system may use a specially designed "snap fit" or "quick connect" fitting 133 to connect the multi-use subassembly 3 and the single-use subassembly 5. The fitting 133 may also comprise a dust cap or other protective means for preventing contamination of the fluid lines.

Figure 24:
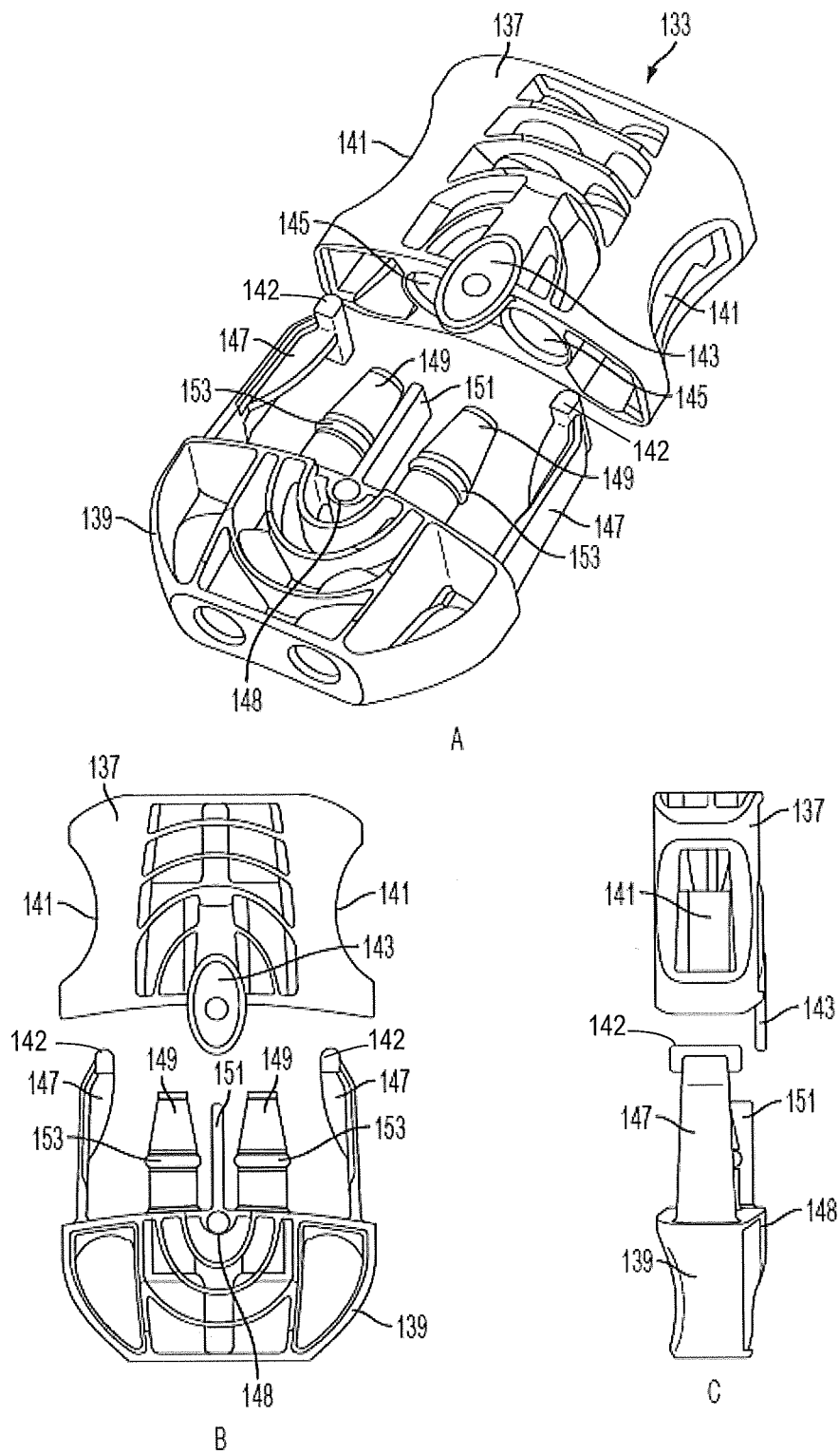
FIG. 24a is a side perspective view of the quick connect fitting.
FIG. 24b is a top perspective view of the quick connect fitting.
FIG. 24c is an additional side perspective view of the quick connect fitting.
Figure 28:
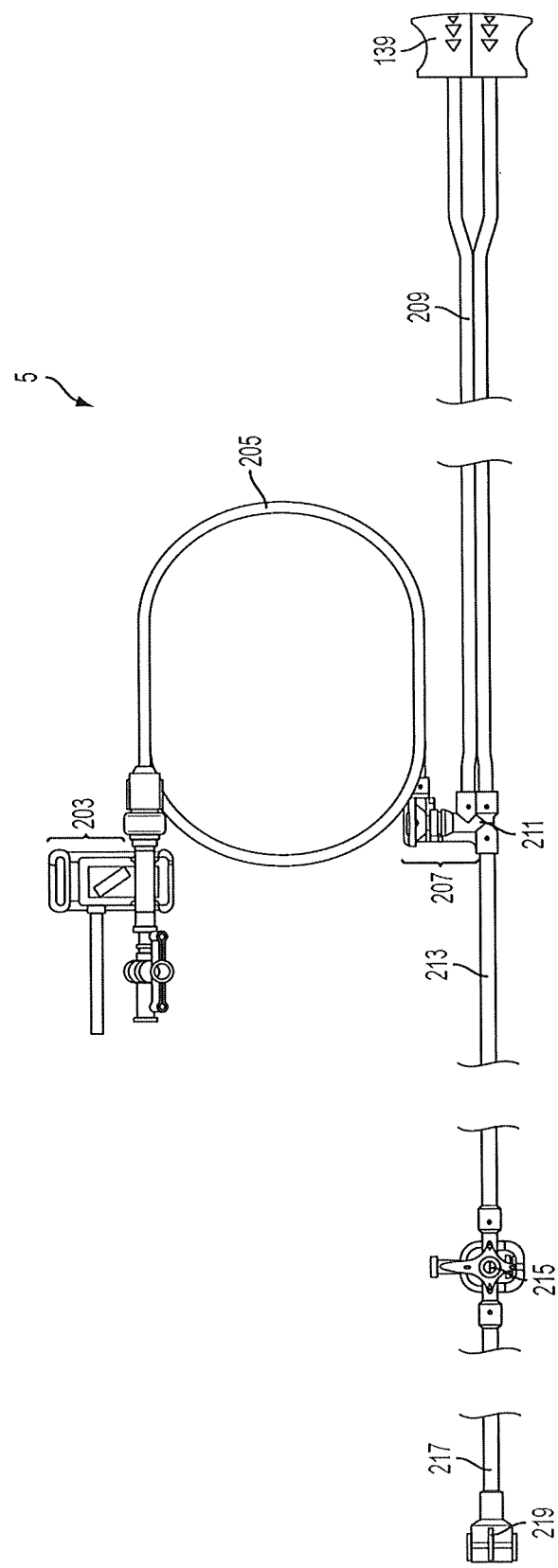
FIG. 28 is a side view of the single-use subassembly.
Figure 29:
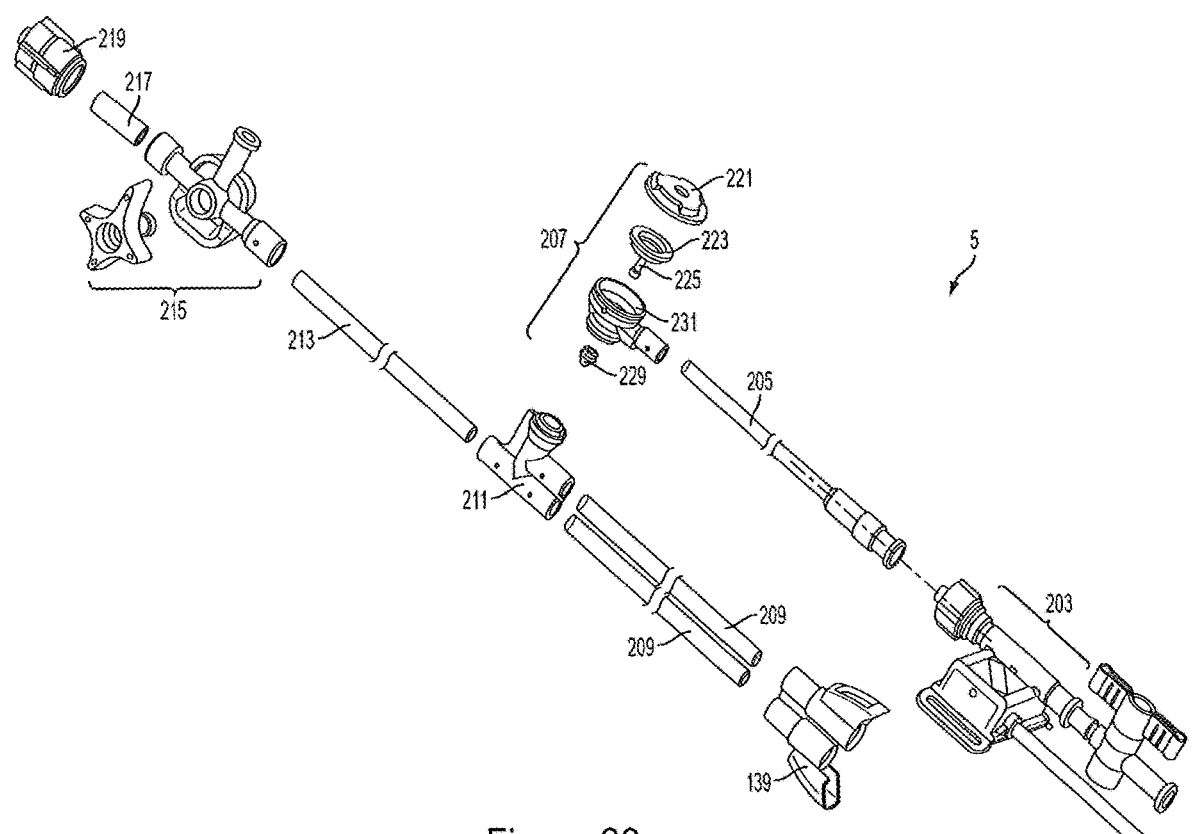
FIG. 29 is an exploded perspective view of the single-use subassembly.

As seen in FIG. 24, the fitting 133 may comprise of a multi-use connector 137 and a single-use connector 139. The multi-use connector 137 may be attached to the multi-use connector 137 which is in fluid communication with the barrel, as seen in FIG. 12. The single-use connector 139 may be attached to the single use tubing set 209, as seen in FIG. 28. The multi-use connector 137 may have securement grooves 141, alignment ridge 143, and female tubing connections 145. The single-use connector 139 may have securement tabs 147, alignment ridge 148, male tubing connections 149, tubing seals 153, and an anti-rotation means 151. The alignment ridges 143, 148 are designed to provide the user with tactile surface when grasping the fitting 133. The alignment ridges 143 of multi-use connector 137 and the alignment ridge 148 of the single-use connector 139 may both have convex, concave, or other mirrored shapes so the user knows by touch or feel that the connectors 137, 139 are properly aligned when connected. The male tubing connections 149 may comprise a tubing seals 153, such as a standard O-ring, to prevent leaking and ensure a fluid tight seals within the fitting 133. The anti-rotation means 151 may be comprised of an additional protrusion or flange extending from the single-use connector 139 that aligns with a slot (not shown) in the multi-use connector 137. The purpose of the anti-rotation means 151 is to provide additional connective support or structure to fitting 133 and prevent unwanted twisting or rotation during high pressure injections.

During use, the user may use the curvature of the alignment ridges 143, 148 to provide tactile feedback that the single-use connector 139 and multi-use connector 137 are properly aligned. As the user pushes the connectors 137, 139 together the male tubing connection 149 will automatically align with the female tubing connection 145 creating a tactile and audio feedback; similarly the anti-rotation means 151 automatically slides within corresponding slot in multi-use connector 137. The securement tabs 147 of the single-use connector 139 slide along the securement grooves 144 of the multi-use connector 137 until the user hears a "click" sound and feels a haptic response that the fitting 133 has been properly connected. To disconnect the fitting 133 the user simply needs to push the tabs 147 in towards the center of the fitting 133 and the pull apart the connectors 137, 139. In an alternative embodiment, the securely tabs 147 may comprise a foot 142 having a notch (not shown). The notch may align with a corresponding tab or extension (not shown) protruding within securement grooves 141 of the multi-use connector 137. When securement tabs 147 are aligned with securement grooves 141 and are pushed together the notch on foot 142 may fit within the protruding tab or extension. This notch and groove fitting may provide additional connective support or structure to fitting by eliminating twisting or rotational movement of the foot 142 and tab 147.

Figure 25:
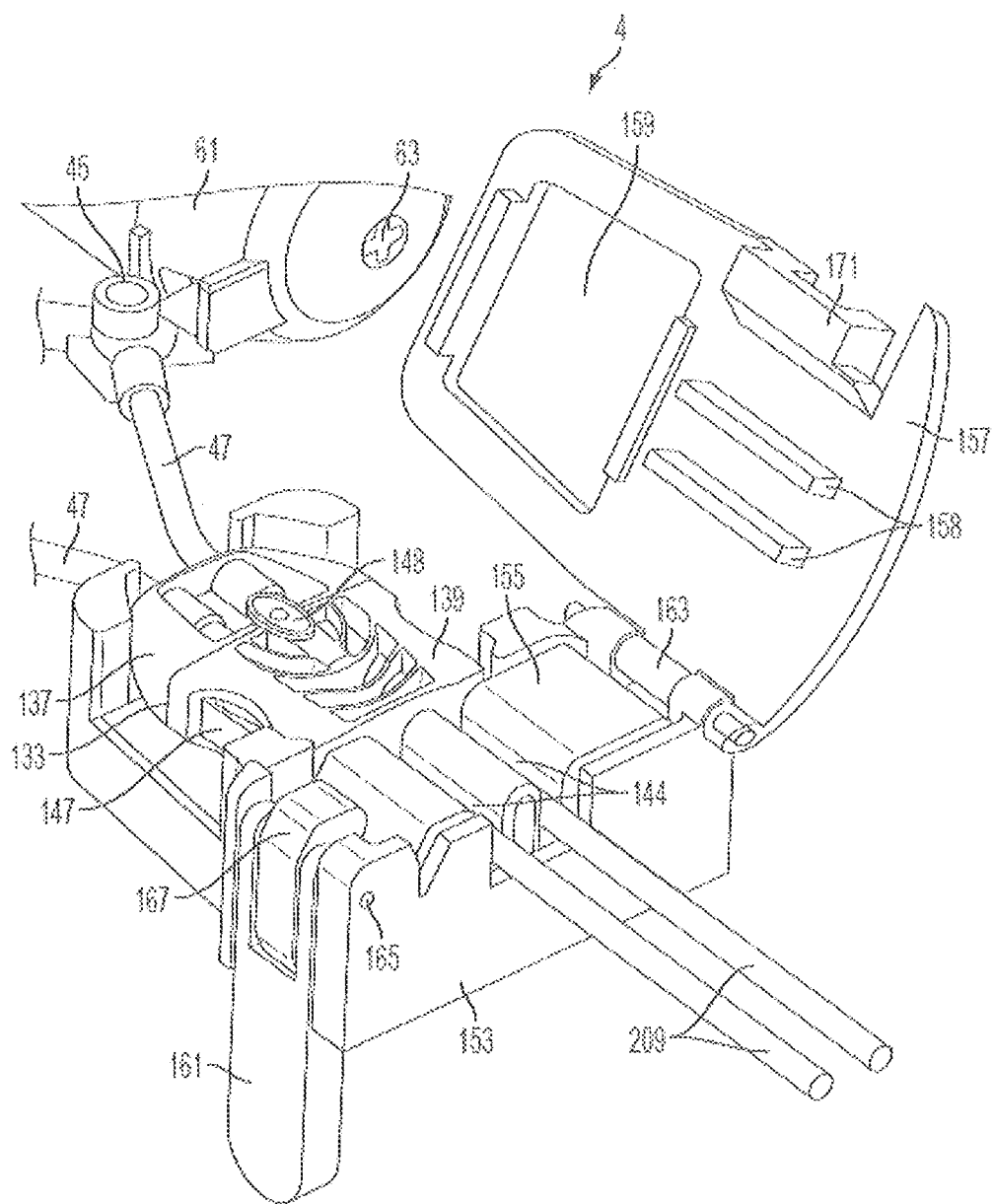
FIG. 25 is a side perspective view of the fitting housing in an open position.
Figure 26:
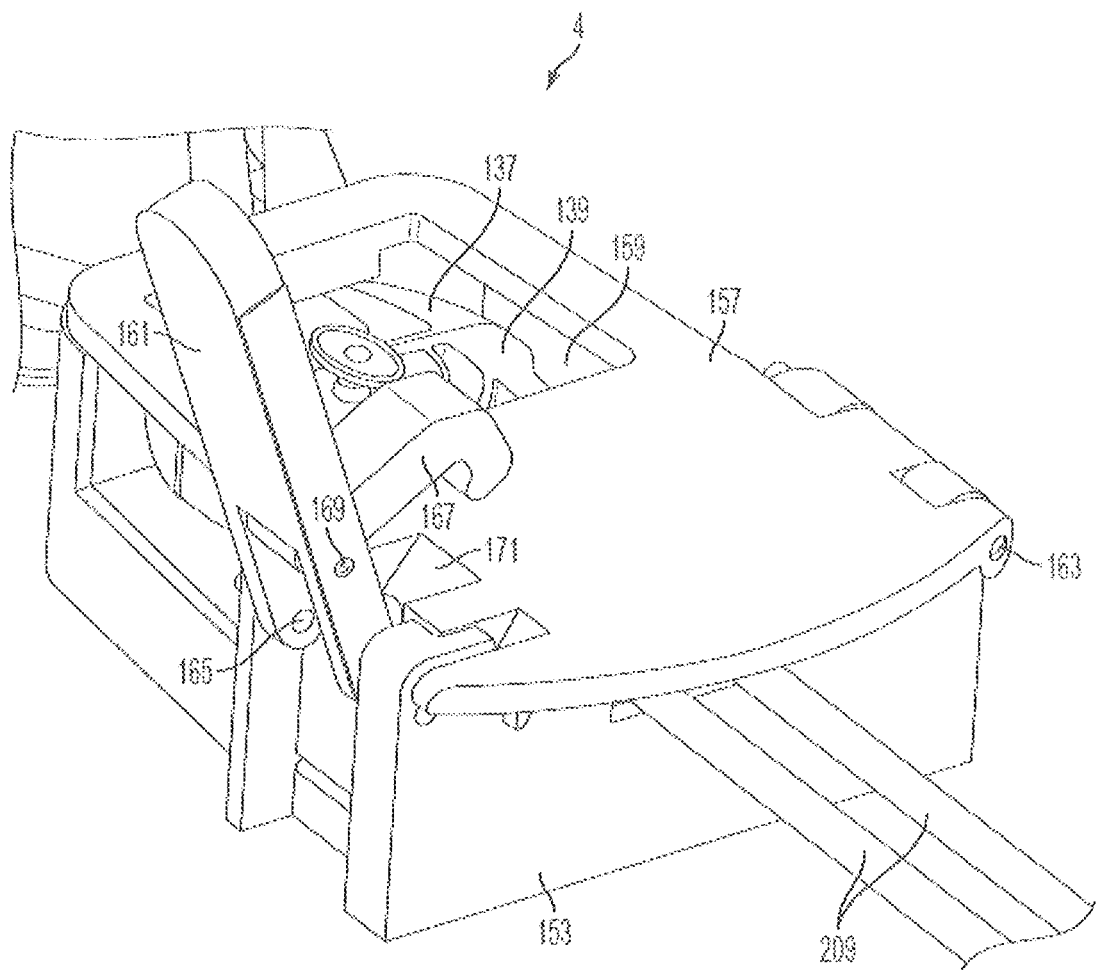
FIG. 26 is a side perspective view of the fitting housing in a closed position.
Figure 27:
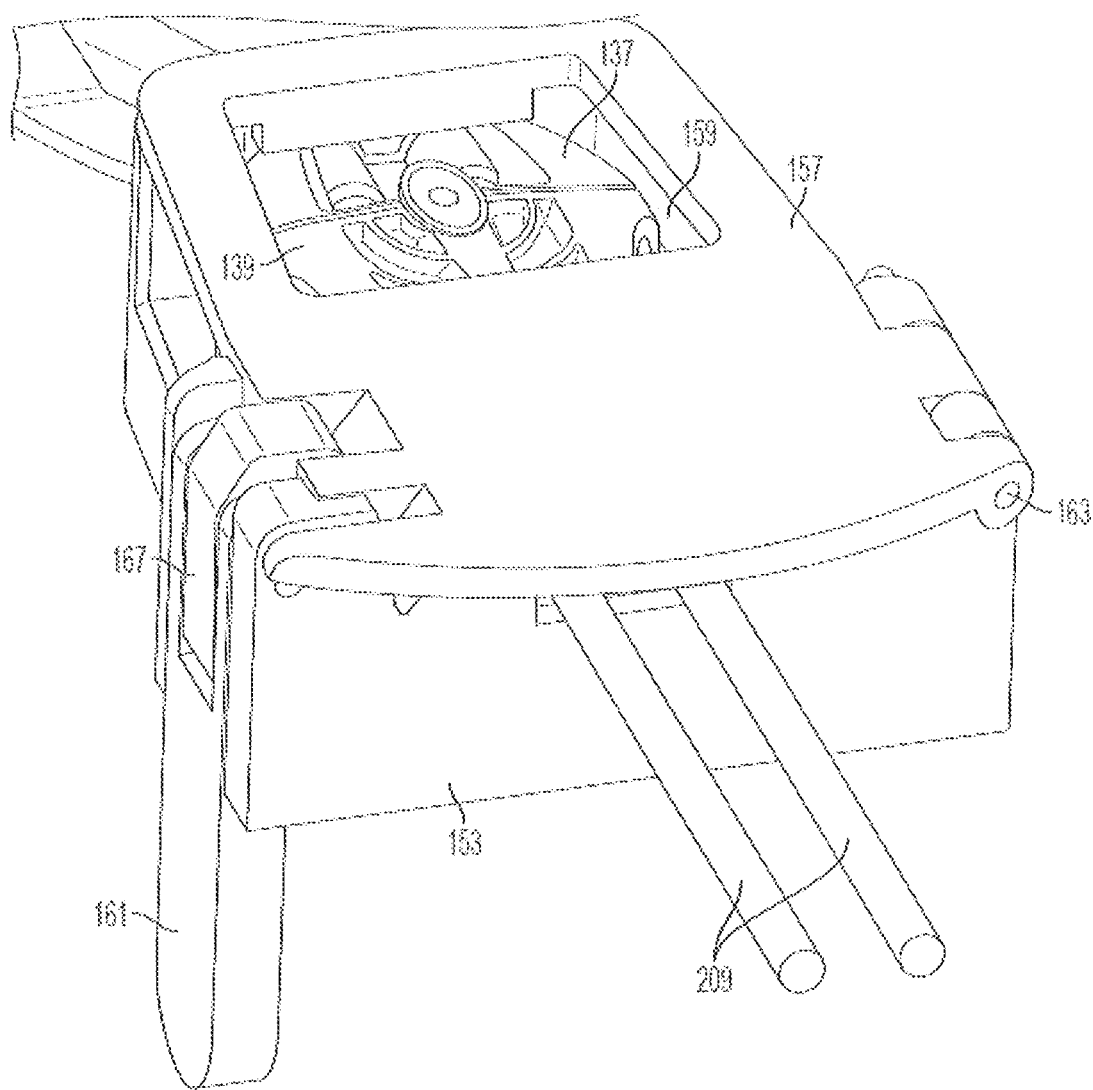
FIG. 27 is a side perspective view of the fitting housing in a locked position.

FIG. 25-27 illustrates the placement of the connection 133 within the housing base 153. House base 153 extends from the injector housing and is used to securely hold the fitting 133 and air sensor 155. Housing base 153 may comprise a seat for the fitting 133, a seat for an air sensor 155, a housing door 157, a viewing window 159, and a locking clamp 161. The purpose of the viewing window 159 is to provide user with visibility of the fitting 133 connection during use. The air sensor 155 may be standard bubble detectors as known in the art and may use ultrasound to detect small amounts of air trapped in tubing 209 of single-use subassembly. If air is detected by sensor 155 in system after purging is complete interface 7 may automatically stop injection to prevent air from being injected into patient. The sensors 155 may include tubing channels 144 to permit proper placement of the single use tubing 209. The housing door 157 may include raised bumps 158 along the inside wall of the door 157. These bumps 158 are designed to align with the tubing channels of the sensor 155 so when the door 157 is closed and in a locked position the bumps 158 ensure the single use tubing 209 remain securely inside slots 144 ensuring the sensors 155 obtain an accurate reading.

The housing door 157 may be connected to housing base 153 via a hinged connector 163 that allows the door 157 to swing open and close. When door 157 is in an open position the fitting 133 may be placed into base 153 and single patient tubing 209 may be placed into air sensor 155 slots 144. After fitting 133 is properly in place the door 157 may be closed and securely locked to base 153 using the clamp 161. The clamp 161 may also be connected to base 153 via a hinged connection 165. The clamp 161 may include a locking means 167 that is connected to the clamp 161 via another hinged connection 169. When the clamp 161 is hinged or pulled upwards into an open position, as seen in FIG. 26, the locking means 167 may align with a notch 171 on the top surface of the housing door 157. As the clamp 161 is pushed downwards the locking means 167 grasps along the door notch 171 and securely locks the door 157 to the base 153, as seen in FIG. 27.

As seen in FIGS. 28-31, the injector system includes a single-use disposable subassembly 5. This single-use subassembly 5 is intended to connect the multi-use subassembly 3 with the procedure catheter (not shown) via fitting 133. The single-use subassembly 5 may comprise a single-use connection 139, pressure transducer 203, pressure monitoring line 205, pressure protection valve 207, co-extruded high pressure tubing 209, a tubing junction 211, high pressure tubing 213, a distal high pressure stopcock 215, catheter connection tubing 217, and a procedure catheter connection 219. An advantage of using the single-use subassembly 5 is to eliminate the risk of infection or contamination of the multi-use subassembly 3. An advantage of single-use 5 subassembly is it may be detached and discarded after each patient, whereas multi-use subassembly may be used for multiple patients, saving user both time and money.

The single-use connection 139 is connected to and in fluid communication with co-extruded high pressure tubing 209 which is able to withstand injection pressure of at least 1,400 psi. Tubing 209 may be a co-extruded dual lumen fused component designed to avoid tangling of individual lines. Proximal end of tubing 209 may be aligned with air sensor 155 to prevent unwanted air being injected into patient. Distal end of tubing 209 is connected to and in fluid communication with a tubing junction 211. The tubing junction 211 is connected to and in fluid communication with both a pressure protection valve 207 and single lumen high pressure braided tubing 213 rated up to at least 1,400 psi. The high pressure braided tubing 213 is connected to and in fluid communication with a distal high pressure stopcock 215. The stopcock 215 may be used to deliver fluids to the catheter, draw blood samples, or remove waste from the system.

The single-use 5 subassembly is able to mix contrast and saline in-line. The co-extruded dual lumen tubing 209 may have separate lumens for contrast fluid and saline fluid. When the co-extruded dual lumen tubing 209 reaches the tubing junction 211 it is at this point that the saline fluid and contrast fluid may be mixed together into the single lumen high pressure braided tubing 213 to form a diluted or mixed solution. For example, if user elects to inject a solution having the ratio of 50% contrast and 50% saline then equal amounts of contrast and saline will be injected from the barrels of multi-use subassembly and travel along the co-extruded dual lumen tubing 209 until the fluids reach tubing junction 211 at which point the two fluids may mix together to form a diluted solution. Alternatively, the user may inject a highly diluted contrast solution, such as 20% contrast and 80% saline, and still be able to achieve high quality images. An advantage of this system is providing the user the able to dilute contrast fluid and still achieve high quality images. Therefore, diluting contrast being injected into the patient with a mixture of saline means less contrast solution may be used during a procedure, and over time this can lead to huge savings in both wasted contrast and money spent on contrast.

These various tubing junctions and connections between different components of the single-use disposable subassembly 6, together with the multi-use subassembly 3, may be permanently secured by various methods known in the art, including, but not limited to, UV bonding, adhesive material, or ultrasound bonding, and intended to withstand injecting pressures of at least 1,500 psi.

The pressure protection valve 207, pressure monitoring line 205 and pressure transducer 203, are described in U.S. Pat. No. 6,896,002, entitled PRESSURE TRANSDUCER PROTECTION VALVE, and U.S. Pat. No. 6,986,742, entitled PRESSURE TRANSDUCER PROTECTION VALVE, and both are incorporated herein by reference. The pressure protection valve 207 is intended for a two-way connection and fluid communication between tubing junction 211 and a disposable pressure transducer 203. Pressure transducer measures the patient's blood pressure.

Figure 30:
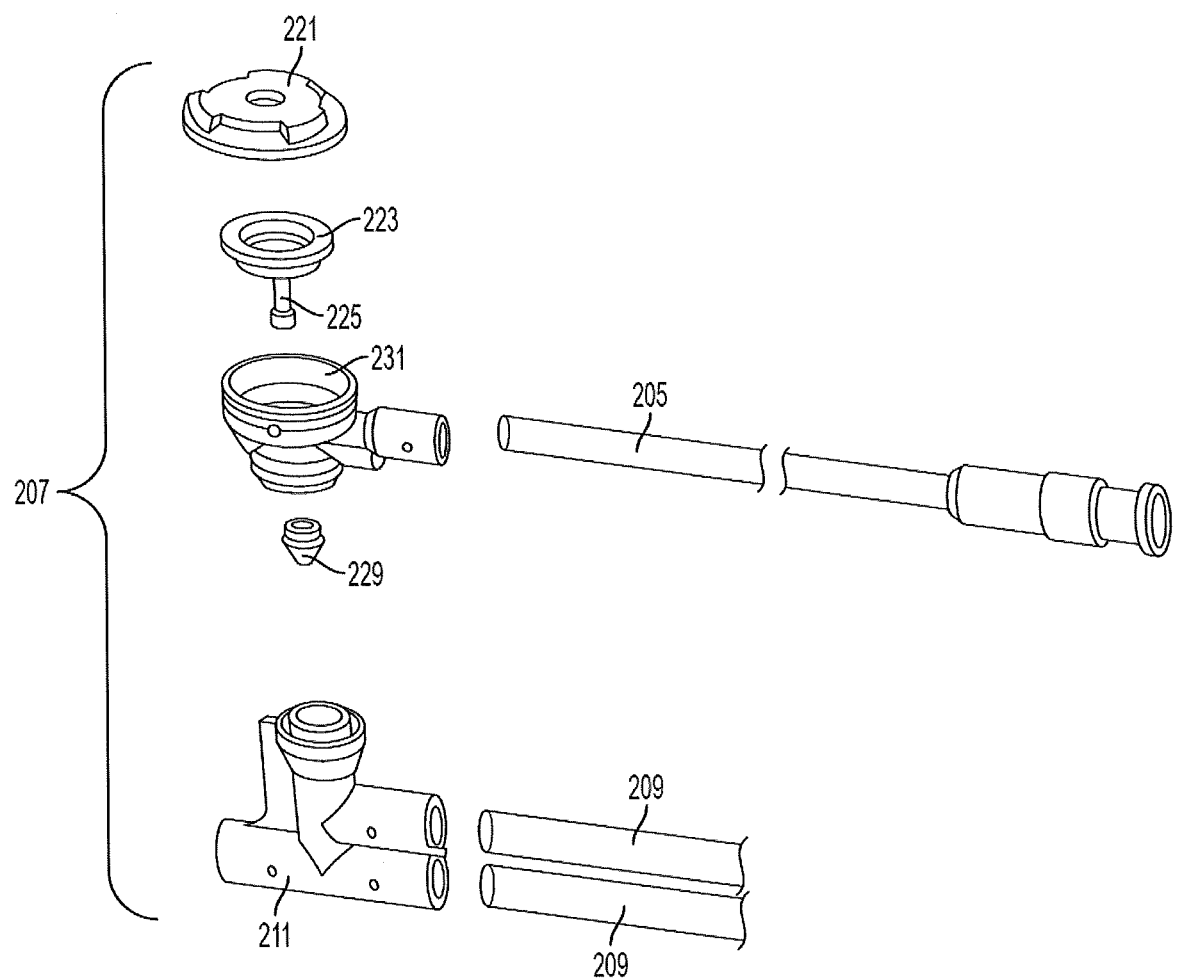
FIG. 30 is an exploded perspective view of the pressure protection valve.
Figure 31:
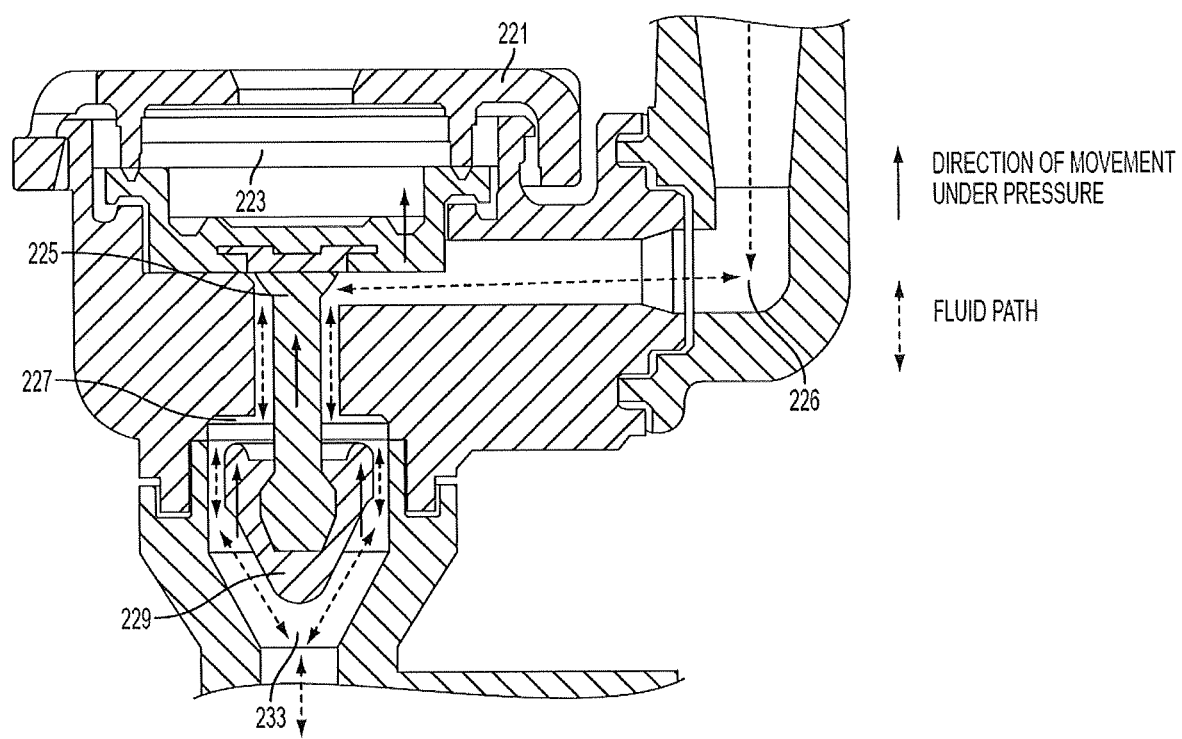
FIG. 31 is a side cross-sectional view of the pressure protection valve.

Referring to FIGS. 30-31, the pressure protection valve 207 includes a cap 221, a flexible diaphragm 223, a stem 225, a sealing surface 227, a body 229, a housing 231, source fluid channel 233 and a pressure transducer tubing connection. The pressure protection valve 207 is activated when a pressure fluctuation exists between source fluid channel 233 and a pressure transducer tubing connection 235 causing the compliant flexible diaphragm 223 to deflect away from its original position towards the channel 233. The top of the integrated stem 225 is connected to the diaphragm 223 and the bottom of the stem 225 is connected to the body 229. The deflection of the diaphragm 223 moves the integrated stem 225 away from the channel 233, causing the body 229 to engage a sealing surface 227 and create pressure isolation between channel 233 and disposable transducer 203. This seal protects the disposable transducer 203 from excessive pressure which may damage or impact the transducer 203. The pressure protection valve 207 may create a seal to protect transducer 203 before fluid pressure in channel reaches a pressure sufficient to damage the transducer. Once pressure of fluid flow through channel 223 is lowered the diaphragm 223 moves back to its original position, thereby separating the body 229 from the sealing surface 227 and re-establishing or opening fluid communication between the transducer 203 and channel 223.

In yet another embodiment of this invention, there may be a need in the art for both the single-use subassembly 5 and multi-use subassembly 3 to be single patient use only. For example, if the fluid source 23, such as the contrast container, is indicated as a single use only then each component of the injector that contacts the fluid may need to be changed after each use. In this embodiment, the components of both the single-use subassembly 5 and multi-use subassembly 5 may remain the same as above except for the fitting 133. In place of the quick connect or snap fit fitting 133 of the previous embodiment, this embodiment may use a standard luer type connection as known in the art or be directly bonded together. The standard fitting connection would fluidly connect the injector tubing 47 of the multi-use subassembly and the proximal end of tubing 210 of the single-use subassembly 5.

Figure 32:
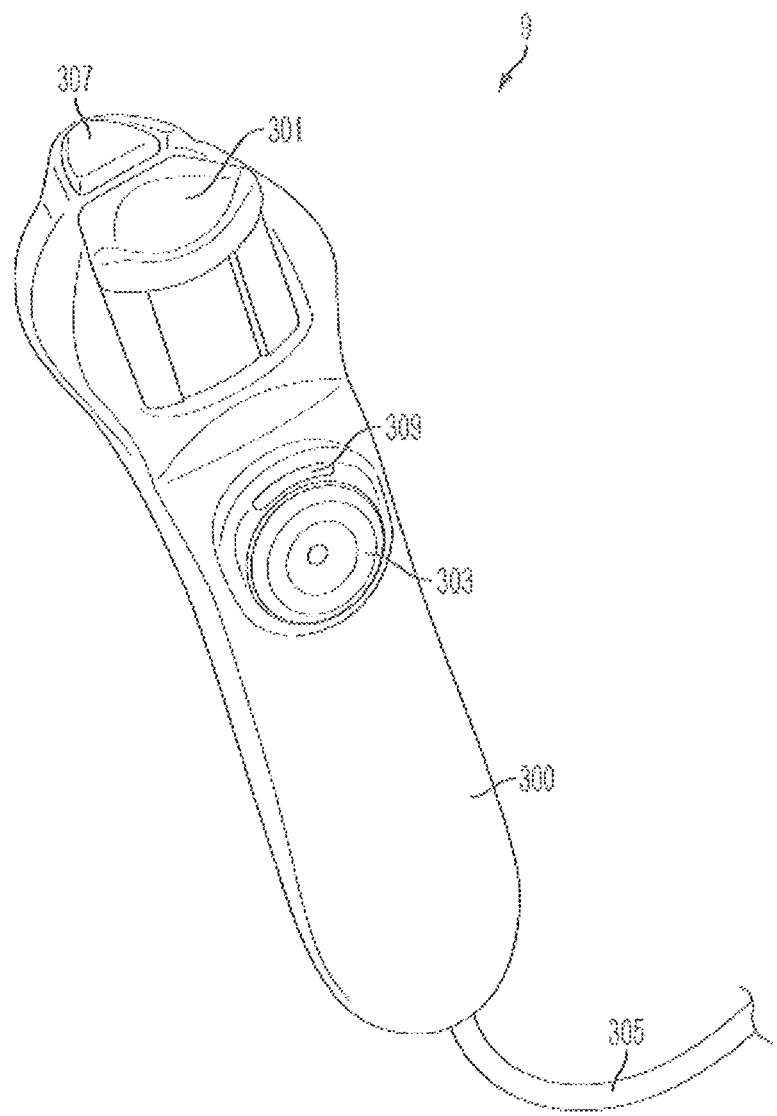
FIG. 32 is a side perspective view of the hand controller.
Figure 33:
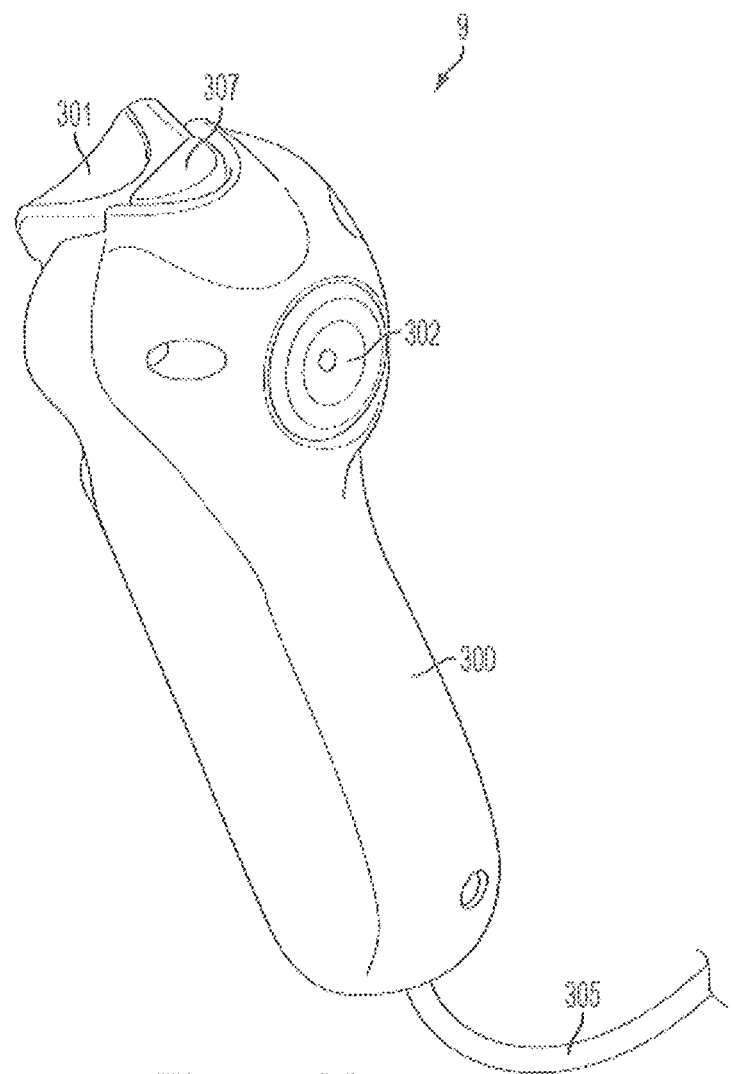
FIG. 33 is a rear perspective view of the hand controller.
Figure 34:
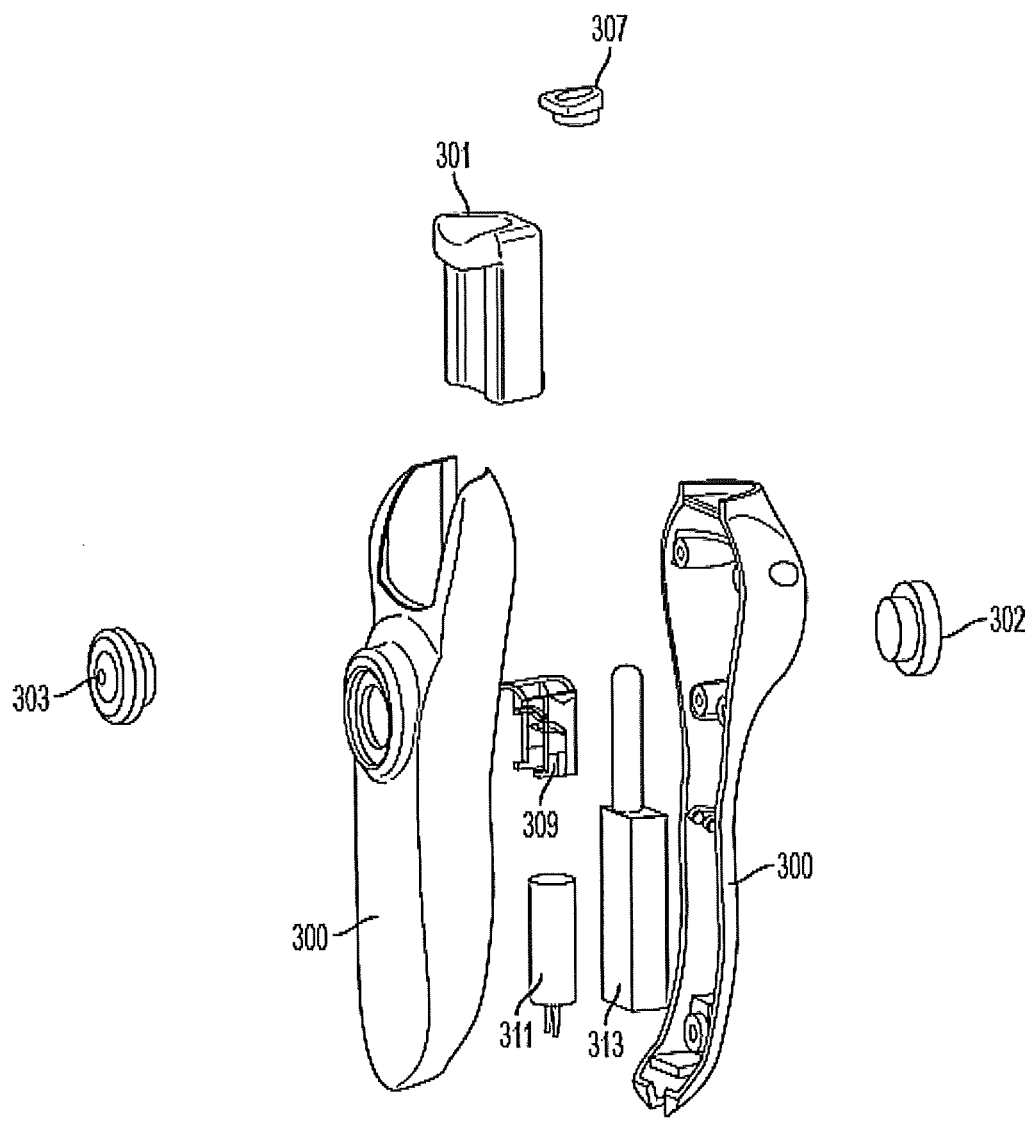
FIG. 34 is an exploded perspective view of the hand controller.
Figure 35:
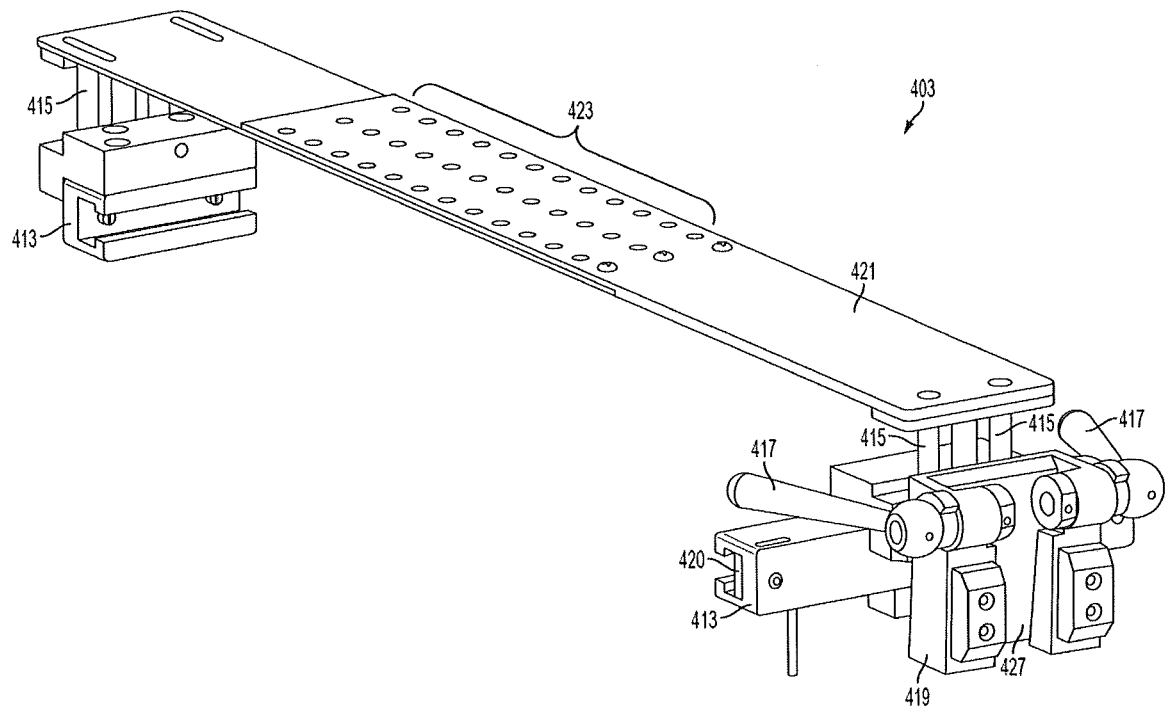
FIG. 35 is a side perspective view of the mounting system.
Figure 36:
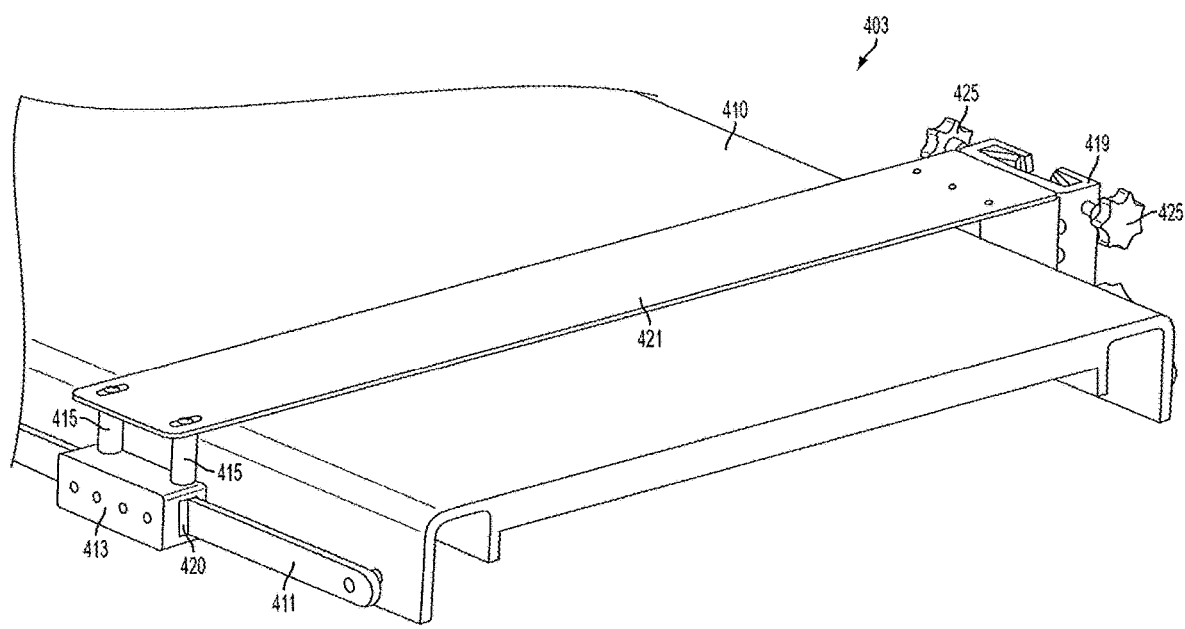
FIG. 36 is a side perspective view of the mounting system securely attached to a bed.

As is shown in FIGS. 32-34, a controller 9 of the invention may include a handle 300, a front actuator 301, rear flush button 302, a selector 303 for selecting a fluid source from which to inject fluid within a patient, a puff button 307 for injection of a small controlled amount of fluid, and a visual identifier 309 to notify user of the type of fluid selected to inject. Controller 9 may also include various internal components including, but not limited to, a tactile feedback means 311 for providing a tactile or haptic response, and a sensor 313 for measuring position of actuator 301. The rear flush button 302 may be used to inject a predetermined amount of fluid, such as saline, to flush the system or procedure catheter. Controller 9 may be used to control the start and stop of injections, flush the tubing lines, deliver a "puff" or selected amount of contrast, select the type of fluid to be injected into the patient, and warn the user when an injection may be dangerous to the patient or system.

FIG. 32 depicts a controller 9 according to certain embodiments of the invention. The controller 9 communicates with the user interface 7 via control cable 305. In certain embodiments, the controller 9 can be connected and disconnected from the control cable 305 via a first connector (not shown) that matches up to a second connector (not shown) on the cable 305. The connection between the first and second connectors can be made using any suitable connection means known in the art, for example male and female mini-DIN connectors. Alternatively, in certain embodiments, the controller 9 communicates wirelessly with user interface 7. Any suitable wireless protocol may be used in the invention, including 802.11(a, b, g, or n) and any other suitable protocols used in the art. In certain embodiments, the controller 9 may be connected to user interface 7 via a network connection, including over the internet. Accordingly, in certain embodiments, controller 9 includes hardware and/or software for transmitting and receiving signals over a network, including wirelessly.

Controller 9 is, in certain embodiments, composed of materials that can be sterilized once or more than once, for example by autoclaving, irradiation, or alcohol swab or immersion, or may be kept sterile during the procedure by placing a protective disposable sleeve over controller 9 during use.

The front actuator 301 may have a finite distance to travel within the controller 9. The user may move or press down on the front actuator 301 in order to cause a corresponding movement of fluid between the injection system and a patient. The depression of the actuator 301 may send an electronic signal to either the user interface or the injector. The relationship between how much the user moves the front actuator 301 and the quantity of fluid that is infused into a patient may be any useful or advantageous relationship, and may depend upon, among other things, the application for which the automated fluid management system is used, the injection mechanism employed by the automated fluid management system, the inputs user selected on the user interface 7, or the preference or selection of the user. In certain embodiments, the mapping between the amount a user moves the front actuator 301 and the quantity of fluid infused is linear (i.e. the transfer function is linear), advantageously permitting the controller to function similarly to an infusion syringe and in a manner that is familiar to physicians and easier to learn. In other embodiments, the mapping between the amount of movement of the front actuator 301 and the quantity infused is non-linear (i.e. the transfer function is nonlinear), permitting the tailoring of fluid delivery to specific uses. For example, if a high power injection of contrast agent is desired, the mapping may be linear over a portion of the travel of the front actuator 301, then exponential over another portion, then linear again.

The controller 9 also includes a selector 303 for selecting one of a plurality of fluid reservoirs within the automated fluid management system from which to infuse fluid into a patient or into which to deposit fluid from a patient. In preferred embodiments, the injector system includes reservoirs for saline and contrast, and the selector permits users to select one of these reservoirs or a mixture of both reservoirs that are mixed inline during fluid delivery.

Controller 9 may provide the user with feedback as to the status of a patient or the automated fluid management system. Feedback may be sent to and received by user in various forms including, but not limited to, audio feedback, visual feedback 309, such as LEDs or flashing lights, tactile or haptic such as resistance in front actuator 301 or vibrations. In one embodiment, front actuator 301 provides the user with position-based feedback as to the level of fluid in the barrel 35 of the multi-use subassembly 3 selected with the selector. The front actuator 301 has a finite travel within the controller, and the position of the actuator along its travel corresponds to the fluid level within the selected barrel 35. The fluid level can be measured in absolute terms, for example in mL, or in relative terms, e.g. percent fullness. In certain embodiments, the fluid level in the barrel 35 maps linearly to the position of the front actuator 301 along its travel, i.e. the transfer function is a linear function. These embodiments permit a user of the controller 9 to receive tactile or haptic feedback from the actuator 301 in a manner similar to the plunger of an infusion syringe in a manual injection system known in the art. For example, tactile or haptic feedback may be felt if distal end of catheter is occluded preventing fluid to flow from injector. These embodiments may advantageously permit new users to rapidly learn how to use controllers 9 of the invention. However, in other embodiments the fluid level will map in a non-linear (e.g. exponential) manner, i.e. the transfer function is non-linear. These embodiments may permit users of controllers to tailor the feedback information provided by the actuator to specific applications.

In certain embodiments, the position of the front actuator 301 and the degree of movement map to fluid level and fluid displacement, respectively, in the same way. For example, the controller 9 may be configured to behave as a 10 cc syringe, so that movement of the actuator 301 along 10% of its total travel results in the infusion of 1 cc of fluid into or out of a patient, and when the actuator 301 is positioned at the midpoint of its travel, the selected barrel 35 will contain 5 ml of fluid. It should be noted that, in an embodiment such as this one, after a user moves the front actuator 301 to cause fluid to be infused into a patient, the user may let go of the front actuator 301 and the it will remain in the position in which the user left it. In other embodiments, however, the mapping of the fluid level in the selected reservoir to the position of the front actuator 301 for the provision of feedback may be different than the mapping of the position of the front actuator 301 to the amount of fluid that is infused into a patient. In these embodiments, after the user releases the front actuator 301, or after the user has stopped applying force to the front actuator 301, the actuator 301 changes position based on the fluid level within the selected barrel to provide position-based feedback of fluid levels. In other embodiments the position of the front actuator 301 and the degree of movement map to velocity based control. For example, the controller 9 may be configured so that at rest and no movement equals zero velocity and full depression on front actuator 301 equates to full velocity of injection. The velocity is based off of flow rates, so if the maximum flow rate is set at 5 mL/sec when front actuator 301 is completely depressed fluid is delivered at the maximum flow rate of 5 mL/sec.

The front actuator 301 of the controller may provide feedback in other ways and for other parameters. In certain embodiments, in addition to providing position-based feedback to users, the front actuator 301 also provides resistance-based feedback to users. The resistance-based feedback may in the form of vibrations, resistance in movement of the front actuator 301, or providing the user with a haptic response such as shaking or jarring of the controller 9. The haptic or tactile feedback, such as vibrations, shaking, or jarring of controller 9, may be generated by the tactile feedback means 311 as seen in FIG. 34. Preferably, resistance based feedback is provided based on a level of fluid pressure within the injector system. For example, the font actuator 301 may resist movement from rest to a relatively high degree, or the controller 9 may begin to vibrate, if the fluid pressure is relatively high within the injector system. For example, if injection begins to approach max pressure limits, the vibrations may increase in frequency and/or intensity. Similarly, front actuator 301 may resist movement from rest very little or not at all, or the controller 9 may begin to vibrate, if the fluid pressure is relatively low. The degree of resistance may be determined by the controller based on relative pressure values or absolute pressure values and, as discussed above, the mapping between pressure and resistance applied may be linear or non-linear. For instance, in certain embodiments, the resistance may be set to a maximum when the pressure reaches or exceeds a certain value, and may be set to zero when the pressure reaches or drops below another value, advantageously mimicking the kind of resistance provided by a standard infusion syringe and catheter set-up, which is familiar to physicians and easy to learn. Alternatively, the resistance may be zero below a particular threshold value, then maximum above that threshold value.

In certain embodiments, the controller 9 provides additional or secondary feedback via other mechanisms, including visual identifiers 309 including LEDs or display screens, and audio feedback including audible alerts.

Controller 9 of the invention can be made any suitable size or shape, and have any suitable actuator mechanism. Controllers 9, actuator 301, and selector 303 may have any suitable form factors. For example, actuators 301 may be made in form factors including plungers, joysticks, rocker switches, toggle switches, paired buttons, scissor handles, trackballs, computer mice, touch wheels, scroll wheels, etc.

In one embodiment (not shown) the controller 9 may have a form factor resembling infusion syringes generally used in the art. It includes multiple ergonomic finger holes into which a user can place fingers or thumbs to advantageously achieve comfortable leverage over the actuator 301. The actuator 301 may be shaped like a syringe plunger, and is operated in a manner similar to the plunger of an infusion syringe: the actuator 301 is pushed inward to cause the system in infuses fluid from a reservoir into a patient.

In yet another embodiment of the controller 9, as seen in FIG. 32, the front actuator 301 may be a depressible button. Controller 9 once again includes a handle 300 optionally ergonomically shaped, permitting users to grip the handle 300 with their fingers and palm while operating the actuator 301, 302 and the selector 303. The front actuator 301 may include a depressible button that may be operatively moveable by the user's thumb. For example, the user may depress or press down on front actuator 301 to cause infusion. The controller 9 may also have a finger-operated rear button actuator 302, as seen in FIG. 33. The rear button actuator 302 may be used in place or in conjunction with front actuator 301, and may cause infusion when depressed by user. The selector 303 preferably includes a button allowing user to choose various options for selecting saline, contrast, or mixture of both. Additionally, the controller 9 may have a puff button 307 that allows the user to inject a defined pre-set amount of fluid, contrast, saline or a mixture of both, every time it is pressed to help visualize where the catheter tip is located in the body. The actuators 301, 302 of this embodiment may provide position-based feedback or resistance-based feedback as disclosed above. The feedback may be created by a motor or spring in the controller body that provides resistance to the actuator. For example, the actuator 301, 302 of this embodiment may be spring loaded so that after being depressed by user the actuator is forced in an upward motion returning to its original state.

Referring now to FIGS. 35-40, the injector system may also include a mounting system. The purpose of the mounting system is to assist the user when transferring the injector housing 13 from a body unit 409 to another surface. In many facilities that use an automated injector system space is limited and many medical personnel are in the room around the injector. Therefore, an advantage of the mounting system is to assist the user in securing the injector housing 13 to a stationary surface, such as a bed 410, wall mount, or ceiling mount, without obstructing the movement of the medical personnel in the room.

The bed mount 403 may include, but not limited to, rail connectors 413, mounting support 415, mount locks 417, mount brace 419, bed support 421, and adjustment means 423. The rail connectors 413 are designed to securely attach the bed mount 403 to the bed rails 411. It is understood that there are many different types or brands of hospital beds 410 and each many have different sized rails 411, therefore it is an advantage of this invention that the rail connectors 413 may be adjustable and able to change sizes to fit various sized bed rails 411. Alternatively, rails connectors 413 may interchangeably fit with the same mounting supports 415 allowing specialized rail connectors 413 to fit a single bed mount 403. The mounting supports 415 are bars or arms that securely connect the rail connectors 413 with the actual bed support 421. The bed support 421 may be comprised of at least one flat bar or arm that extends the width of the bed 410. The bed support 421 may also need to be customized in order to fit various brands or sizes of hospital beds 410, therefore the bed support 421 may have an adjustment means 423 allowing the support to extend or retract for proper fitting. The adjustment means 423 may be a series of screws or bolts that unlock to allow for the bed support 421 to either be extended or retracted and then lock back in place thereby securing the bed support 421. The bed mount 403 may be securely attached to the bed 410 by using the mount locks 417. Mount locks 417 may include, but not limited to, levers, screw locks, or other tightening locks known in the art. The mount brace 419 is used to securely hold and embrace the mounting finger 14, as described in more detail below.

Figure 37:
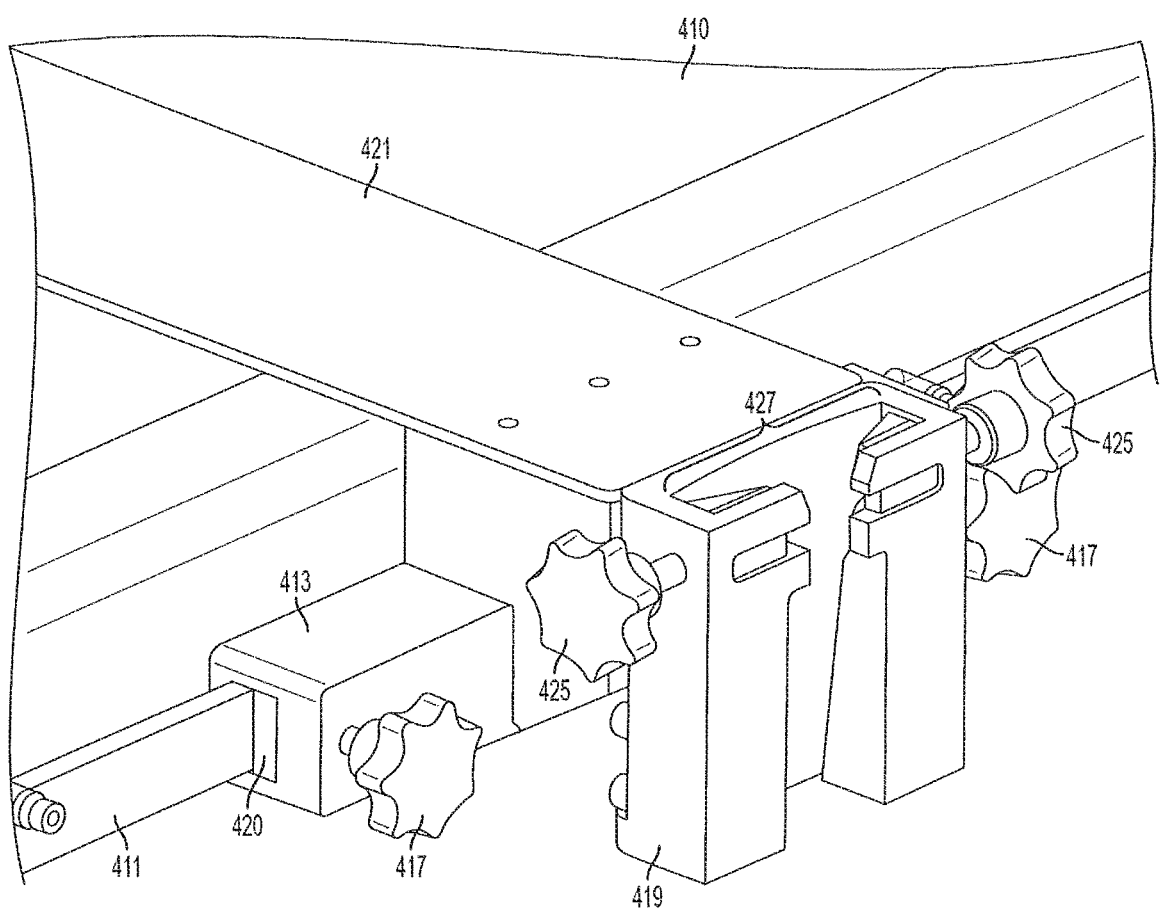
FIG. 37 is a partial side perspective view of the mounting system.

To properly place the bed mount 403 the user may use the adjustment means 423 to extend or retract the bed support 421 so it is properly sized to the bed 410. Next, the rail connectors 413 may be adjusted and slid onto the bed rails 411. The user may use the mounting locks 417 on the rail connector 417 to securely attach the mount 403 to bed 410. For example, as seen in FIG. 37, the mounting locks 417 may include a knob 419 and a locking plate 420. The knob 419 may be turned or rotated which forces the locking plate 420 to move closer to the rail 411, thereby securing the rail connector 413 to the rail 411.

After the mount 403 had been securely attached to the bed 410 the user may then securely attached the injector housing 13 to the mount 403. The top of the connection arm 17 may be securely attached to the bottom of the injector housing 13 (see FIG. 2) and the bottom of the connection arm 17 may be securely attached to the top of the mounting plate 407. The bottom of the mounting plate 407 may be connected to the top of the housing base 405. The mounting plate 407 may have a mounting finger 14 extending off its side. The mounting finger 14 is intended to be sized to securely fit within slot 427 of the mounting brace 419. The mounting finger 14 may have supports 433 extending from the housing base 405 to provide lateral support to finger 14.

Figure 38:
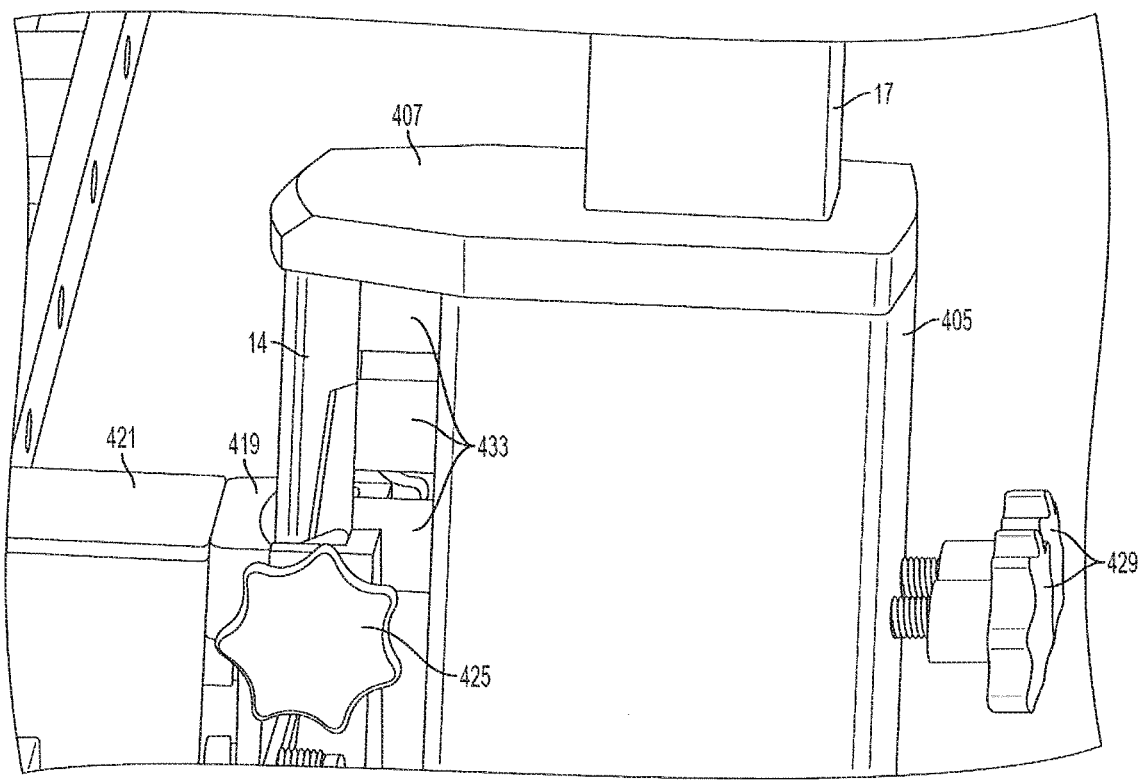
FIG. 38 is a partial side perspective view of the mounting system being attached to the injector housing.
Figure 39:
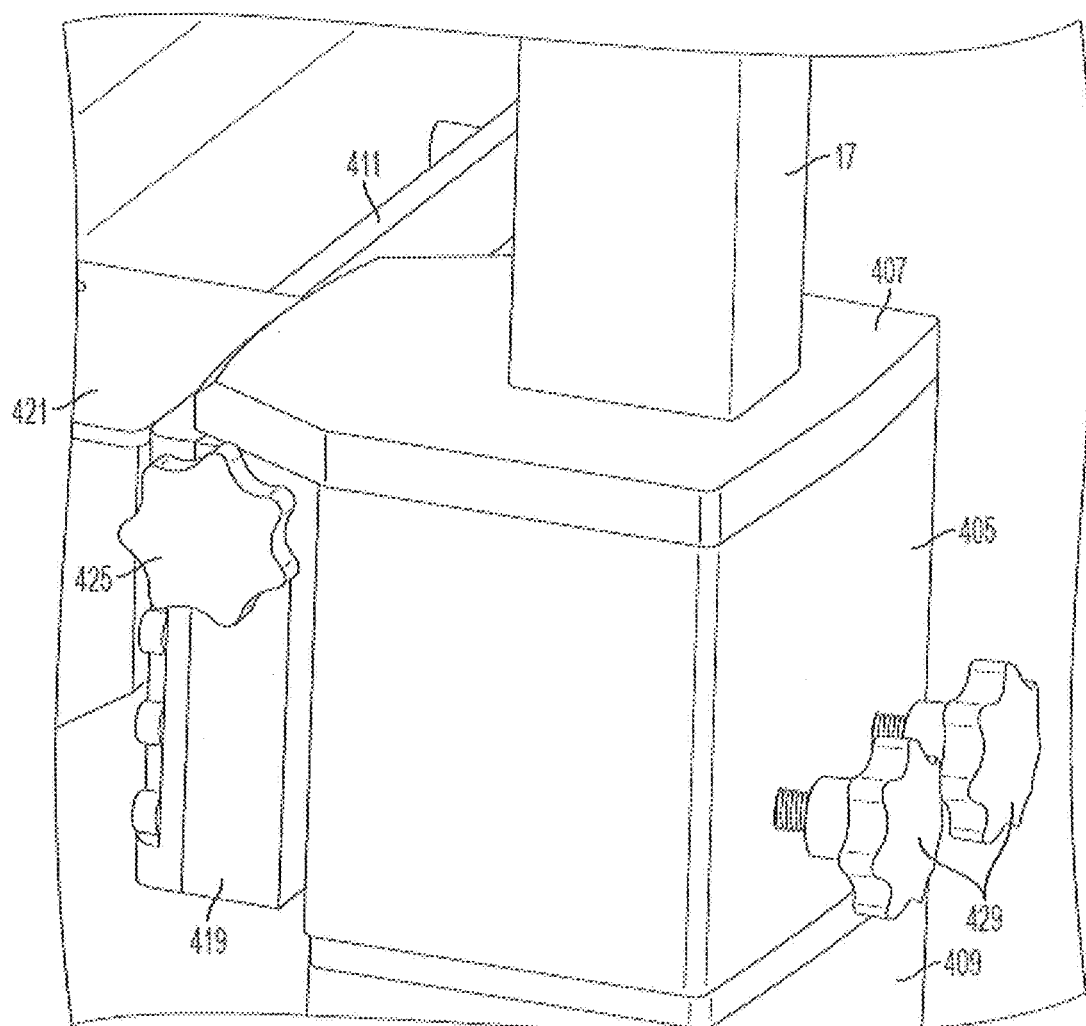
FIG. 39 is a partial side perspective view of the mounting system being attached to the injector housing.
Figure 40:
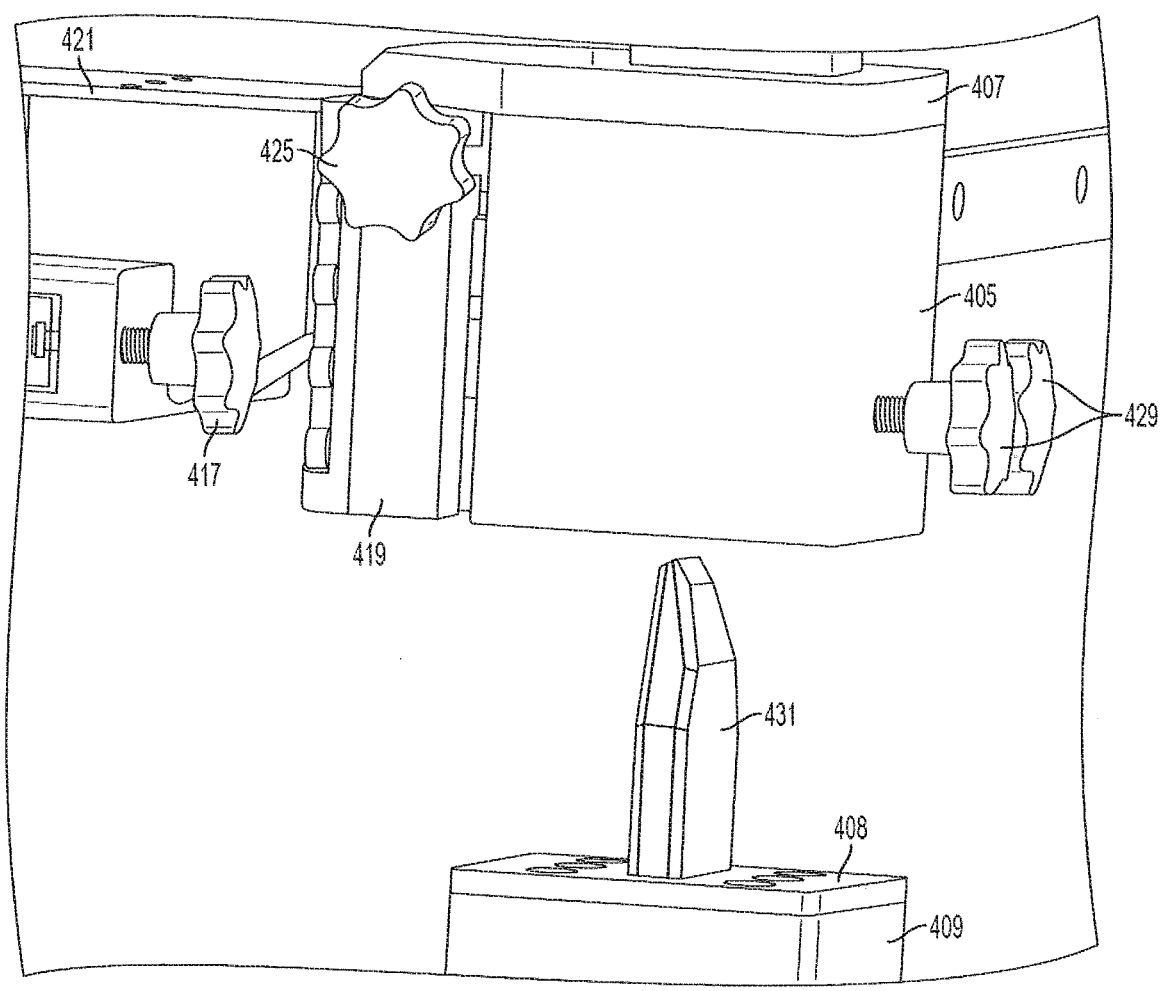
FIG. 40 is a partial side perspective view of the mounting system securely attached the injector housing.

An advantage of this device is the cart 19, as seen in FIG. 2, may have a motorized body 409 or telescoping body, as known in the art, that can extends up and down. As seen in FIG. 40, the top wall 408 of the motorized body 409 may have a base finger 431 that extends into a slot (not shown) of the housing base 405. The base finger 431 may be securely attached to base housing 405 via base locks 429, which may include, but not limited to, levers, screw locks, or other tightening locks known in the art. The user may use the motorized body 409 of the cart 19 to raise the injector housing 13 so the mounting finger 14 is above the mount brace 419. Since the cart 19 may have wheels the user may easily push the cart close to the bed 410 and effortlessly position the mounting finger 14 in place so the tip of the finger 14 is aligned with slot 427 of mounting brace 419, as seen in FIG. 38. Next, the user may lower the motorized body 409 of cart 19 thereby lowering the finger 14 into position so the entire finger 14 is captured within the mounting brace 419, as seen in FIG. 39. Once the finger 14 is positioned inside the brace 419 the user may use the injector locks 425 to securely fasten the finger in place, thereby securing the injector housing 13 to the bed mount 403. After the injector housing 13 is secured to bed mount 403 the user may unlock or loosen the base lock 429 so the motorized body 409 of cart 19 may be lowered down even further, as seen in FIG. 40, completely removing the base finger 431 from the housing base 405.

Once removed, the cart 19 may be moved and stored away providing more free space around the injector for doctors and nurses to walk and work. When the injector housing 13 needs to be moved to another bed the cart 19 may be positioned so the base finger 431 aligns with slot (not shown) of housing base 405. The motorized body 409 may be raised and base finger 431 extends fully into slot. User may secure housing base 405 to body 409 by using the base locks 429. Next, user may unlock the injector locks 425 freeing the mounting plate 407 from the bed mount 403. Finally, user may continue to raise the motorized body 409 until the mounting finger 14 is completely free of mount brace 419, allowing the cart 19 and injector housing 13 to be moved.

As seen in FIG. 41-56, the injector system may comprise of an interactive user interface 7. The interface 7 is intended to control and display various aspects of the injector including, but not limited to, setting injection parameters, automated purging of system, automated injection, displaying real time injection status, and providing a user friendly interface. An advantage of user interface 7 may include a simplified setup procedure or simplified injection procedure. The interface 7 may provide step-by-step prompts or notices that are intended to guide the user through the simplified setup procedures or simplified injection procedures. This simplified setup and injection procedure may decrease the learning curve compared to manual injection systems with manifolds or currently known automated systems. The purpose of the simplified setup procedure or simplified injection procedure is to minimize user interaction with system and automate as many features as possible. The simplified setup procedure may include, but is not limited to, priming the system, steps for attaching the multi-use and single-use subassemblies, and venting the system. The simplified injection procedure may include, but it not limited to, steps for injection of fluids into a patient, auto refill of syringes, and changing system sub-assemblies for the next patient case.

An advantage of minimizing user interaction and automation of system features is to save the user time and also reduce possible user error. Also, by automating certain features, such as priming the system, venting the system, and adjusting contrast to saline ratio, this may minimize the amount of contrast or saline used, thereby decreasing overall contrast waste. The interface 7 may be capable of full automation for certain features, however for safety concerns the interface 7 may require user to confirm certain tasks have in fact been completed. For example, the interface 7 may be capable of fully automating the venting and air purging process, as described below in more detail; however interface 7 may still require user to confirm they have visually inspected all fluid lines and syringes to ensure that no air is present. The purpose of the user confirmation is to provide an additional level of patient safety but still saving user time by automating the process.

Another advantage of interface 7 is to help user be able to adjust contrast to saline mix ratio based on individual patient requirements in order to minimize amount of contrast injected into the patient while achieving clinically acceptable images. Reduction in amount of contrast injected into a patient may help minimize potential for contrast included nephropathy (CIN). In addition, the interface 7 is intended to help user reduce the total contrast used during injection procedures, thereby resulting in total cost savings of over 25% in contrast related expenses for the hospital or user. Another advantage of the interface 7 system is the user has the ability to set patient specific injection parameters, as described in more detail below, which may trigger warning mechanisms when fluid injection maximums have been reached.

The interface 7 may provide the user with multiple mounting options. For example, the interface 7 may be a touchscreen computer housed in a display unit 510 (see FIG. 2). The display unit 510 may be mounted on the injector assembly housing 13 (as seen in FIG. 2) or attached to a hospital bed used for imaging. The display unit 510 may also be attached to a movable arm 11 that folds onto itself to reduce injector footprint when being stored or not in use. The moveable arm 11 may be attached to the injector assembly housing 13 (as seen in FIG. 2) or attached to a hospital bed used for imaging. If the display unit 510 is attached to a moveable arm 11 this may allow interface to be pulled across the patient bed or closer to the user for ease of use and be able to manipulate display unit 510 at varying angles. The display unit 510 may be made of plastics, metals, or various other materials known in the art. The display unit 510 may be capable of contacting various fluids, such as water, saline, contrast, blood, and will withstand high temperatures, resist cracking or damage during normal usage. The display unit 510 may be capable of being cleaned or disinfected with commonly used hospital practices.

For purposes of this application, the terms "code", "software", "program", "application", "software code", "software module", "module", and "software program" are used interchangeably to mean software instructions that are executable by a computer processor as known in the art. The "user" can be a physician or other medical professional.

The interface 7 may be in the form of software that is preloaded onto a touchscreen computer, an application that may be compatible with a smartphone or other portable device, or software that may be transferred onto a touchscreen computer, hospital network, PC or desktop computer. The interface 7 may have backlights that change in brightness so the user can see the interface 7 in a dark room with little or no lighting. The brightness of the backlights may be changed manually by the user or may automatically change depending on the amount of light in the room. The interface 7 may be powered by the injection system and also have a battery backup. The interface 7 may also have an electrical port (such as a USB port as known in the art) or be connected to the internet (either wirelessly or being connected to an Ethernet cable) so that information on the interface 7 may be exported or transferred to another system. For example, the interface 7 may keep a history or summary of injections, as described in more detail below, and user may have ability to copy this injection summary to a portable memory storage unit (such as a USB) or transfer the injection summary over the internet or intranet.

In one embodiment, the interface 7 is on a touchscreen computer with a display screen. The user may control the interface 7 by manually pressing tabs or buttons on the display screen, by remote control, by an application that is compatible with a smartphone or other portable electronic device, or by voice commands. Tabs or buttons may change or alter its appearance to indicate to user that the tab or button has been selected, for example the tabs or buttons upon selection may become highlighted, greyed out, blinking, flashing, or become a visual icon as known in the art. The user may be able to calibrate the interface 7 to change sensitivity levels of the touchscreen display so that system is able to detect the user's touch when wearing gloves, fluids (such as contrast, saline, or blood) is on the screen, or user's hands have become wet. Alternatively, interface 7 may be voice activated or controlled via voice commands so instead of physically pressing a screen or tablet computer user may control interface 7 using a head set.

Figure 41A:
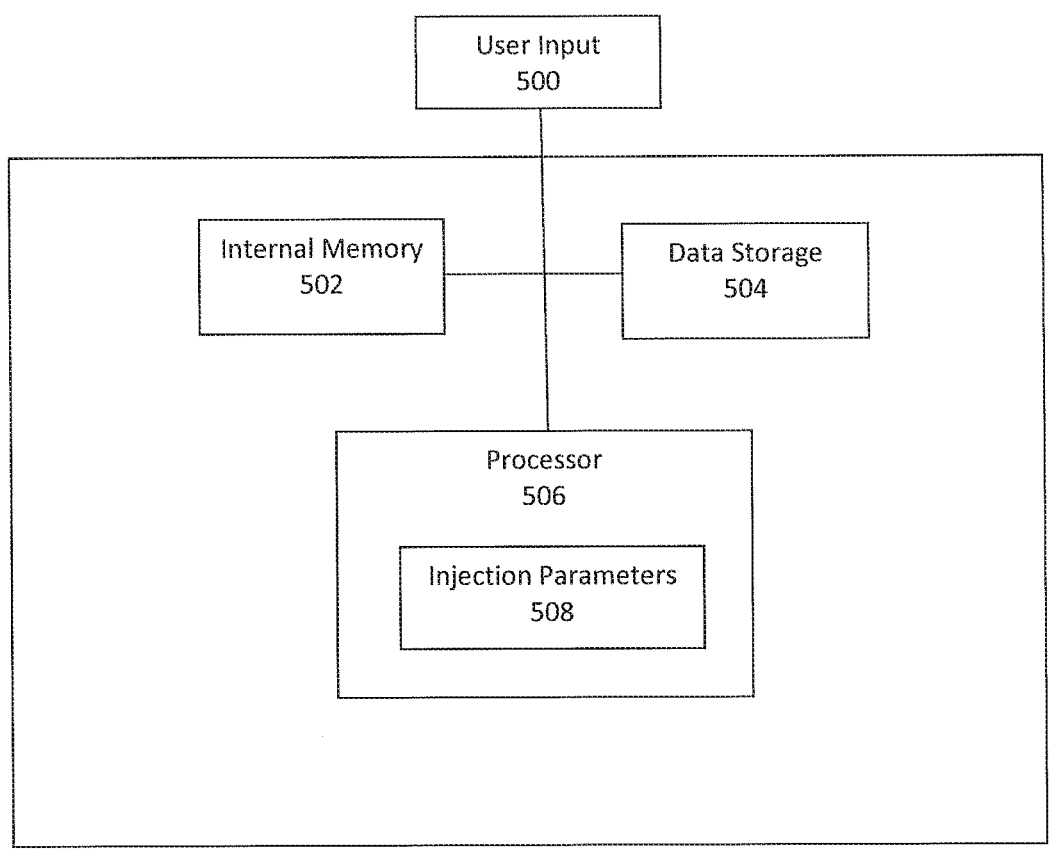
FIG. 41A is a schematic of the interface system of the system of FIG. 2.

As seen in FIG. 41A, a schematic of one embodiment of the interface 7 is shown. The interface 7 may further comprise of an internal memory 502, data storage 504, and a processor 506 or CPU. The internal memory 502 may be used to store user's inputs 500 or selections and transfer this data to the processor 506. Additionally, the user's inputs 500 may also be save in the data storage 504. The data storage 504 may be exported or transferred via an external storage device, such as a USB device, or through an Ethernet cable. After the user's input 500 has been entered and stored a processor 506 may then control the injection parameters 508 of the injection system, as described in more detail below.

The interface 7 may also provide user with visual notifications. For example, the interface 7 software may have integrated visual status notifications that alert user when a change to the system has occurred. The integrated visual status notification may include flashing visual elements on the interface 7 screen, icons or pictures on the interface 7 screen, an LED mounted on the interface 7 housing, or audio notifications. The visual notifications may be used to inform user that the disposable sub-assembly has been properly installed, visualization of the syringes being filled or injected, the system has been armed, the system is injecting, the system has been disarmed, the system has been armed for high flow rate or high volume injections, or that the system is approaching preset maximum flow rate or volume injections based on specific patient criteria.

Figure 41B:
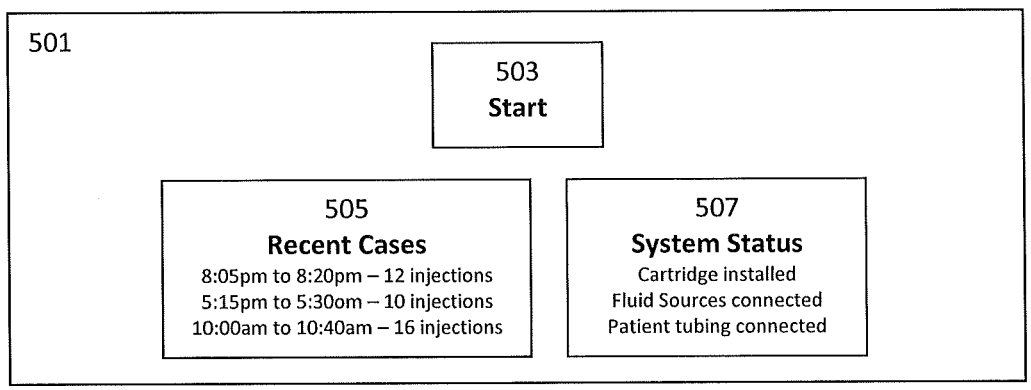
FIG. 41B is an illustration of a Start Screen of the display of the system of FIG. 2.

As seen in FIG. 41B, the start screen 501 is shown having a start tab 503, recent cases tab 505, and a system status tab 507. The recent case tab 505 may include additional text or information about the previous injections performed by the injector. For example, the recent cases tab 505 may include statistics about the previous injections on the start screen 501 and provide user with short summary of the previous injections, such as time of each previous case and number of injections. If the user selects the recent cases tab 505 the display screen may transition the interface 7 to a summary page, as described in more detail below and seen on FIG. 53. The system status tab 507 may include information about which part of the injection system is ready for the procedure. The text in the system status tab 507 may be highlighted or bold to indicate that the particular subassembly has been properly setup. Additionally, the user may be able to select the particular subassembly listed on the status tab 507 to move directly to the setup screen controlling that particular subassembly. Selecting the start tab 503 may transition the interface to the setup screen 509, as seen in FIG. 42.

Figure 42:
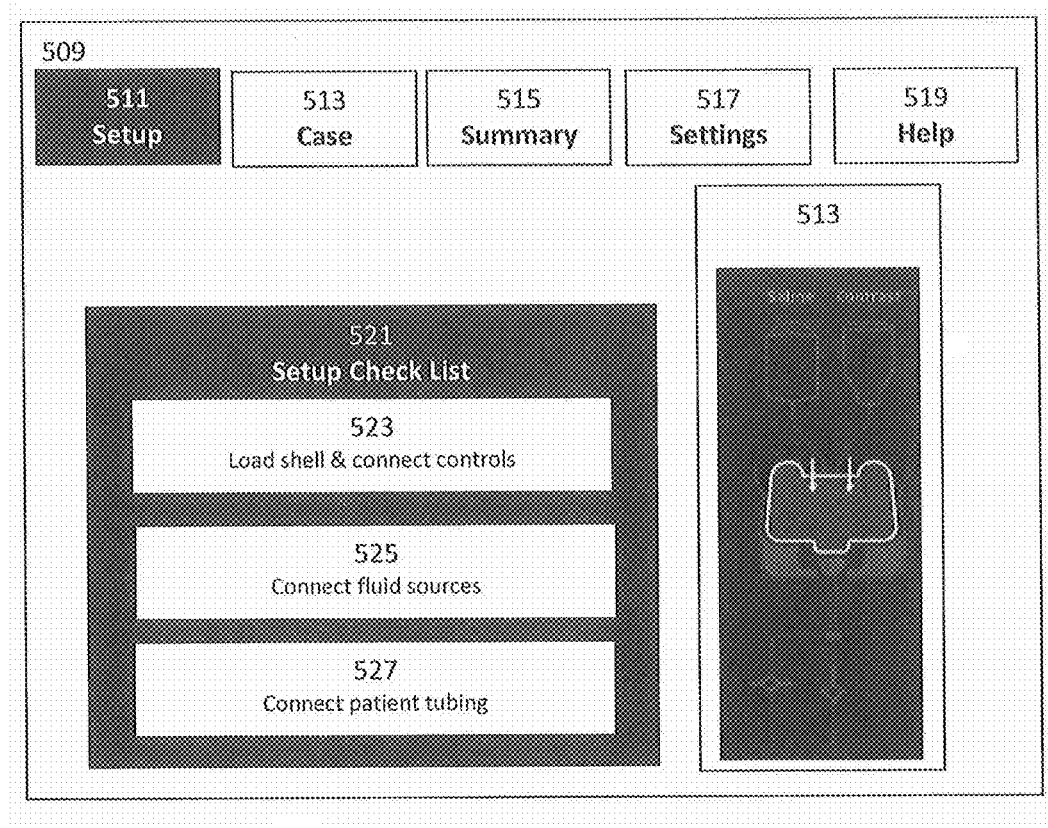
FIG. 42 is an illustration of a Setup Screen of the display of the system of FIG. 2.

Referring now to FIG. 42, the setup screen 509 may comprise several functional tabs, including but not limited to, a setup tab 511, a case tab 513, a summary tab 515, a settings tab 517, and a help tab 719. When the setup tab 511 is selected, as shown in FIG. 42, the tab 511 may become highlighted, greyed out, blink, or otherwise visually indicate to the user that the setup tab 511 has been selected. Upon selection of the setup tab 511 the interface 7 begins a series of prompts to help guide the user in setting up the injector system for use. The prompts may be listed in the check list box 521 containing the individual steps required for properly setting up the injector system for a procedure. For example, the check list box 521 may include, but is not limited to; the following setup prompts, load shell and connect controls 523, connect fluid sources 525, and connect patient tubing 527. Additionally, each individual step may have a corresponding image box 513. The image box 513 may contain a picture, graphic, illustration, or other visual aid to help the user associate the particular step with the injector subassembly or component requiring setup.

Figure 43:
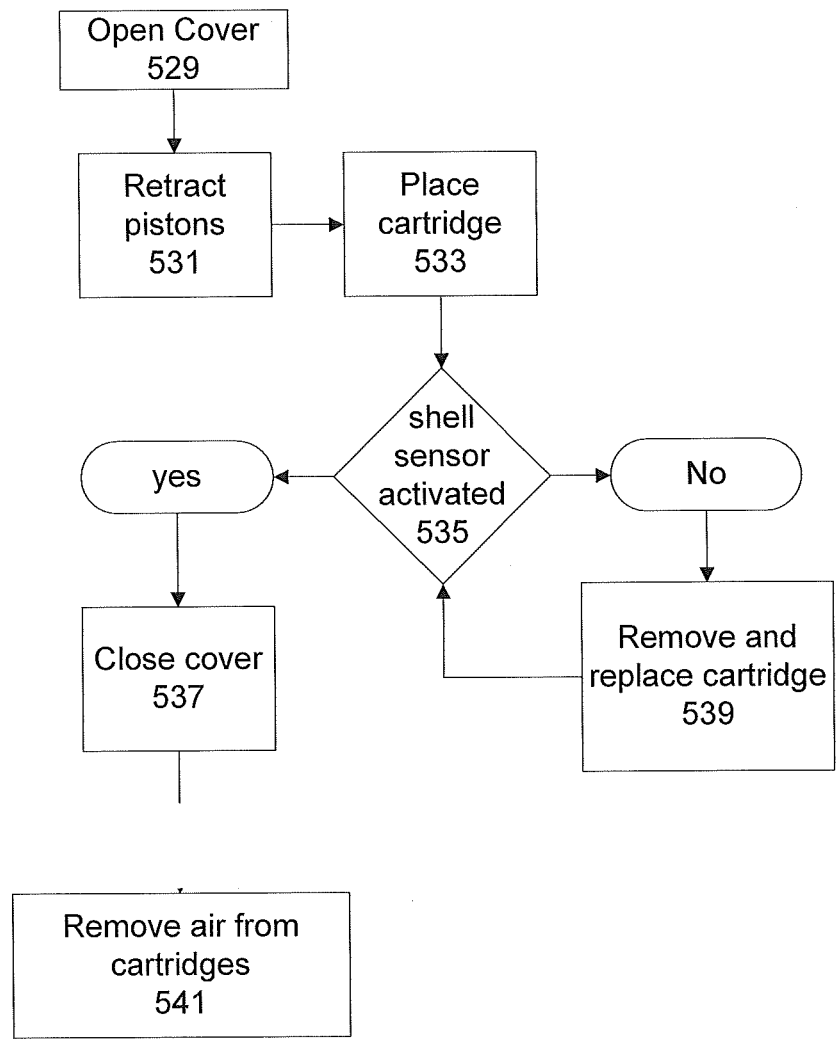
FIG. 43 is a diagrammatic flow chart illustrating the process used to attach the multiple-use subassembly to the injection housing of the system of FIG. 2.

Referring now to FIG. 43, if the user selects the load shell and connect controls 523 prompt the interface will next guide the user through a series of steps as described in the flow chart. Each step in the flow chart may be a separate notice screen, popup window, or other visual aid that is intended to guide the user through various steps in the correct sequence. The interface will prompt user to perform step or will notify user of a step automatically being performed by interface 7. For example, when the load shell and connect controls 523 prompt is selected the first step the interface may indicate the user to perform is open the cover 529. After use has correctly opened the cover, the interface will instruct with the injector system to retract the pistons 531 thereby simultaneously retracting the plungers which are connected to the pistons. Once the pistons have been retracted the interface may inform user to place shell 533 on the injector (as seen in FIG. 22-23A). Once the user has placed the shell 533 on the injector the system will check to determine if the shell sensor has been activated 535. The shell sensor (not shown) may be located on the injector housing and ensures that the user has correctly aligned and placed the shell or detect if any fluid is in the shell. If the sensor fails to detect the presence of the shell the interface will notify user and inform user to remove and replace shell 539. Alternatively, if the sensor detects the presence of fluid in the shell the interface will notify user and inform user to remove and replace shell 539. After sensor has indicated shell is properly in place the interface 7 may notify user to close cover 537 and trigger injector to begin purging or removing air from shells 541. A sensor may detect closing the cover or securement of the latch.

Figure 44:
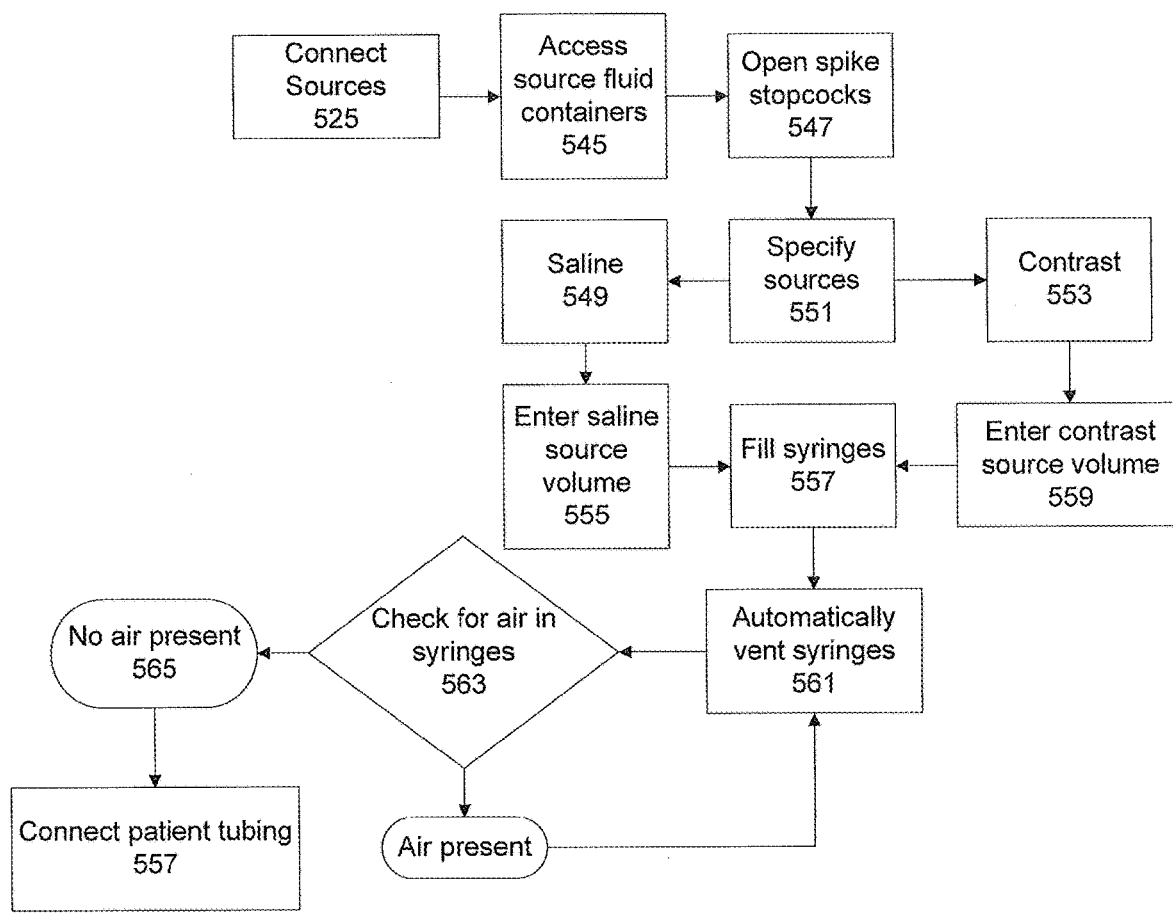
FIG. 44 is a diagrammatic flow chart illustrating the process used to fill and vent the syringes of the multiple-use subassembly of the system of FIG. 2.

Referring now to FIG. 44, if the user selects connect fluid sources 525 prompt the interface may guide the user through a series of steps as described in the flow chart. Each step in the flow chart may be a separate notice screen, popup window, or other visual aid that is intended to guide the user through various steps. The interface may notify user to access source fluid containers 545, then open spike stopcocks 547, and then specify sources 551. The sources may be either saline 549, contrast 553, or any other source (not shown). Once the type of source is selected the user will be prompted to enter either a saline source volume 555 or contrast source volume 559. User may enter volume based on presets or patient specific parameters. After user has entered a source volume 555, 559 the user may select to fill syringe 557. The interface will automatically fill each syringe with the user selected volume. After syringes have been filled to selected volumes the interface may trigger automatic venting of syringes 561 or alternatively the user may manually select to vent syringes on interface (not shown). The system will check for air in syringes and if air is present 559 the system may repeat venting 561 until no air is present 656 at which time interface may notify user to connect patient tubing 557.

Figure 45:
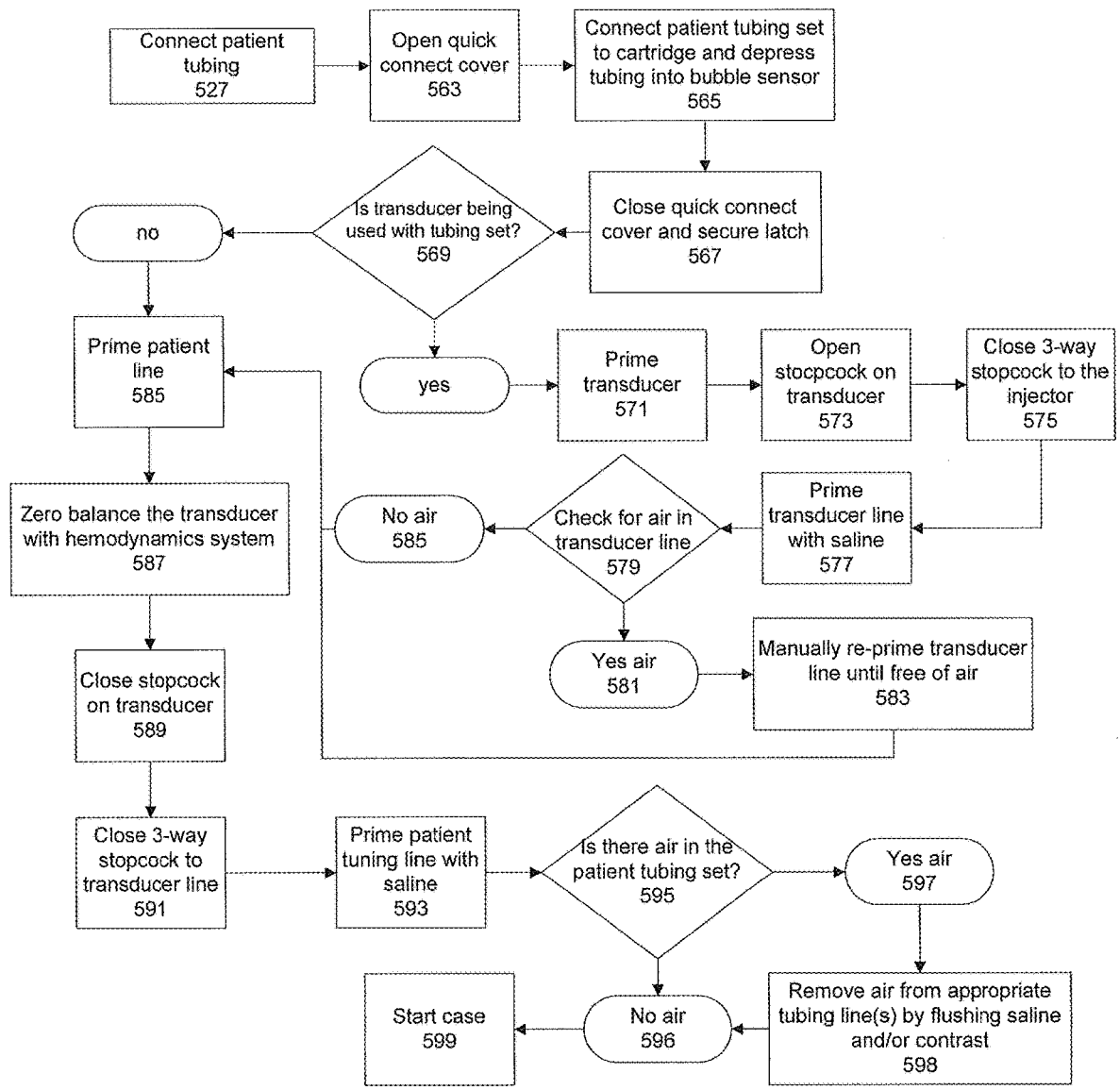
FIG. 45 is a diagrammatic flow chart illustrating the process used to fill and prime the tubing and transducer of the single-use subassembly of the system of FIG. 2.

Referring now to FIG. 45, if the user selects the connect patient tubing 527 prompt the interface may guide the user through a series of steps as described in the flow chart. Each step in the flow chart may be a separate notice screen, popup window, or other visual aid that is intended to guide the user through various steps. First the interface may notify the user to open the quick connect cover 563, then connect patient tubing set to shell and depress tubing into bubble sensor 565, then close quick connect cover and secure latch 567. Once the system has detected the latch has been secured, for example detection by a sensor, the interface may prompt the user to indicate if the transducer is used with the tubing set 569. If a transducer is being used with the tubing set the interface may then prompt user or system to prime transducer 571, open the stopcock on transducer 573, close the three-way stopcock on the injector 575, prime transducer line with saline 577, and check for air in the transducer line 579. If air is present in the transducer line 581 the interface may prompt user to manually re-prime transducer line until it is free of air 583. If no air is present in transducer line 585, or no transducer is being used with the tubing set, the interface may then prompt system to prime the patient line 585, zero balance the transducer with hemodynamics system 587, close the stopcock on transducer 589, close the three-way stopcock to transducer line 591, prime patient tubing line with saline 593, and determine if there is any air in the patient tubing set 595. If air is present in tubing set 597, interface will prompt system to remove air from appropriate tubing line(s) by flushing saline and/or contrast 598. Once no air is present in tubing line 596 the case is ready to start 599 upon users command.

Figure 46:
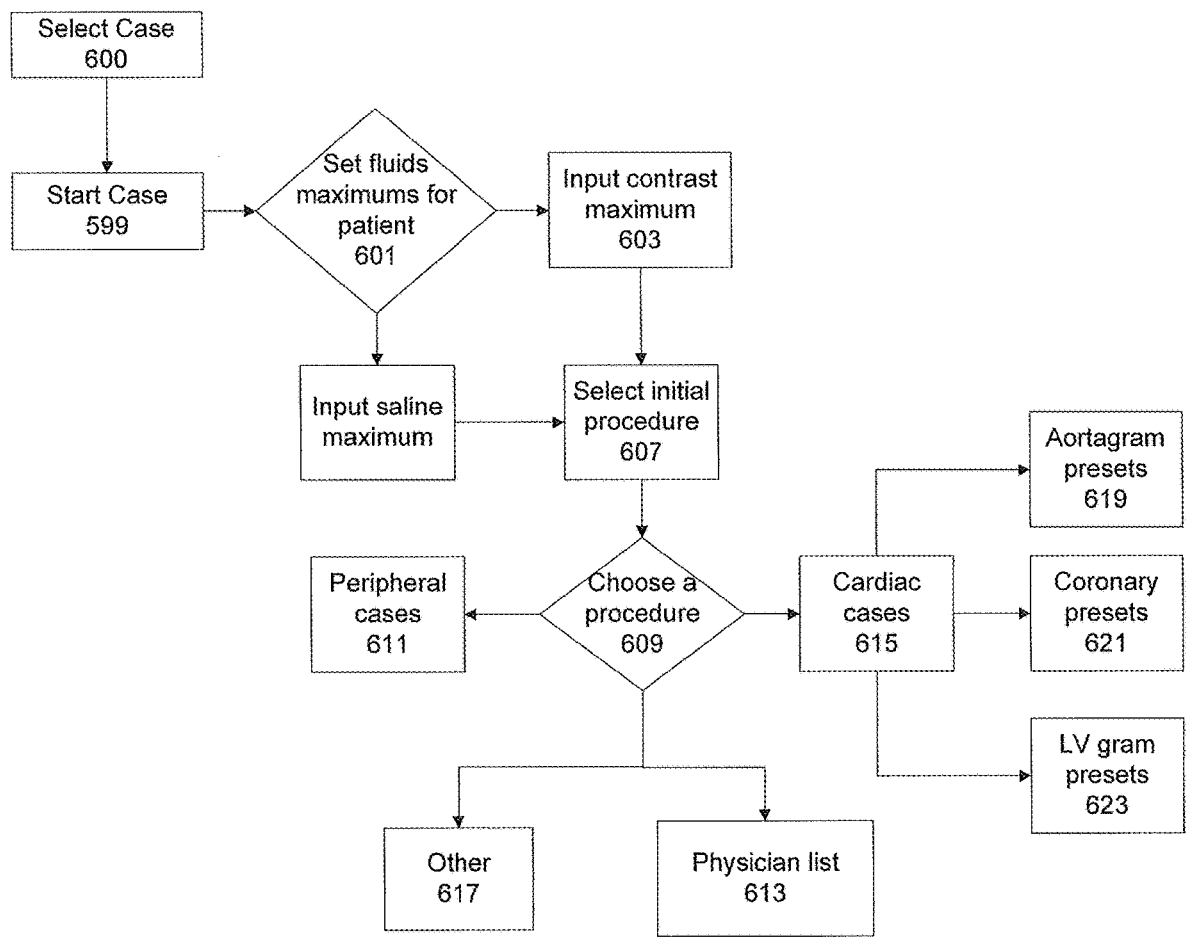
FIG. 46 is a diagrammatic flow chart illustrating the process used to select the procedure type for the system of FIG. 2.

Now referring to FIG. 46, after the injection system and single patient tubing set has been primed the interface may be prompted to help user select the details on the case 600. User may select to start case 599 and interface may prompt to set fluid maximums for patient 601. User may input contrast maximum 603 and saline maximum 605. For example, if the patient suffers from contrast included nephropathy and can only safely withstand a 50 mL of contrast fluid in a 24 hour period then the interface 7 provides user with ability to set the maximum total volume of contrast the system will inject during the procedure to be no more than 50 mL. User may input volume with an onscreen keyboard that indicates. Next, interface may prompt user to select initial procedure type 607 by choosing a procedure 609. The interface may be preloaded with various types of common procedures the injection system may be used for. The interface may provide user with an option of peripheral cases 611, cardiac cases 615, physician case list 613 or other 617 cases. Cardiac cases 615 may include various preset injection parameters depending on the specific type of case, for example interface may prompt user to select from aortagram presets 619, coronary presets 621, and a left ventriculography presets 623. These are merely examples of the type of cardiac preset parameters available to choose from, it is within the scope of this invention that additional procedures may be included in the preset parameter options including, but not limited to, cardiac, catheterization, selective coronary angiography, coronary intervention, coronary angiogram, Chronic Total Occlusion, Transcatheter Aortic Valve Replacement (TAVI/TAVR), and coronary bypass graft angiography. Examples of peripheral cases 611 may include, but not limited to, intravascular ultrasound (IVUS), peripheral angiogram, endovascular aneurism repair, Y-90 mapping, CT cone beam studies, interventions, and any other procedure requiring X-ray imaging of the peripheral. The preset parameter options is intended to be guide for setting up the injection system; each case is unique and may require specific injection parameters so as described in more detail below the user will have the option to change the preset parameters on the dashboard screen prior to starting the case. The physician list 613 may include preset parameters for various physicians using the injector system. Each physician may have unique preset case parameters that they wish to use as defaults. The physician list 613 presets may be changed or updated frequently. Alternatively, interface 7 may provide user an option to skip select case 609 and go directly to dashboard and manually enter injection parameters.

Figure 47:
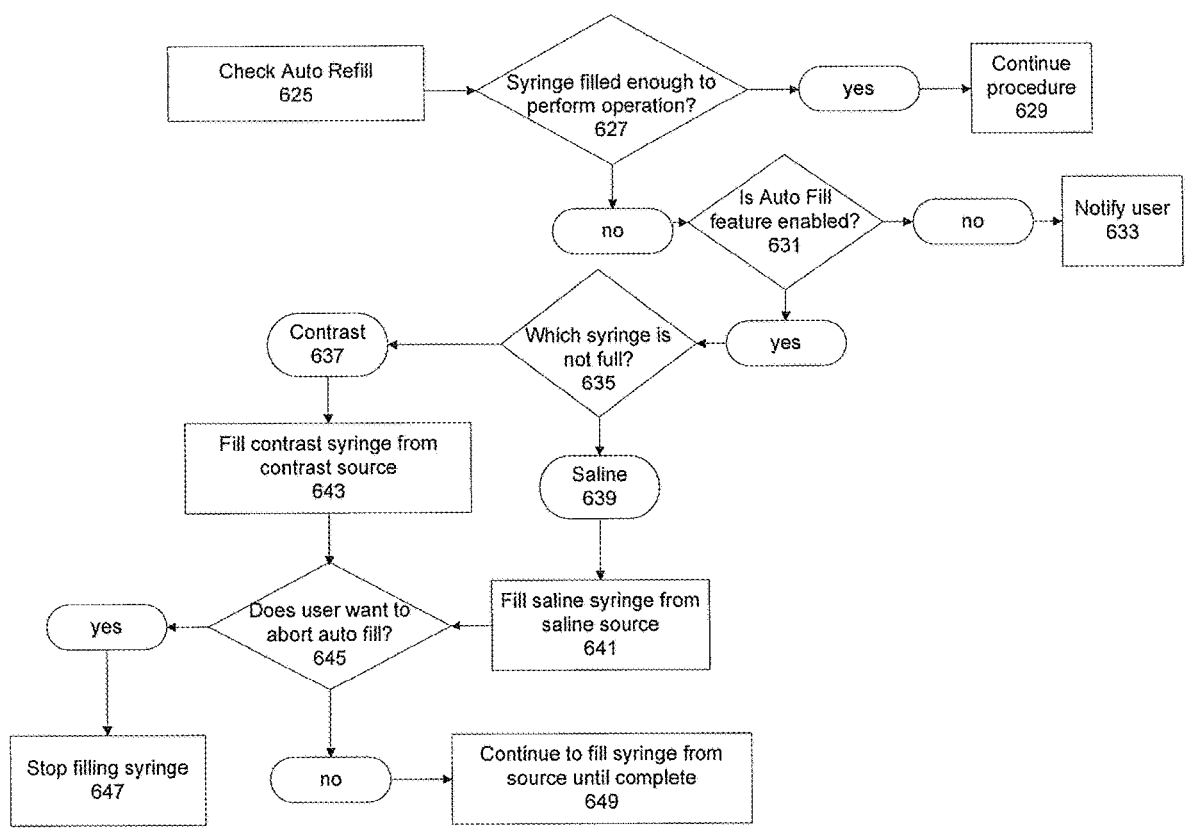
FIG. 47 is a diagrammatic flow chart illustrating the process to automatically fill the syringes of the multiple-use subassembly of the system of FIG. 2.

Referring now to FIG. 47, the system may also include an auto refill option. The purpose of the auto refill option is to provide user with the ability to input minimum syringe barrel volumes at which the system will automatically replenish the syringes with fluid from the sources. The auto refill option may provide user with ability to set maximum fluid volumes. The auto refill option may also provide user with ability to set minimum volumes for each syringe. For example, if the user selects the auto refill option so each syringe has a minimum volume of 25 mL and after 5 injections the contrast syringe volume falls to 15 mL the system will detect that the total volume in contrast syringe has dropped below 25 mL and automatically refill the contrast syringe to either the total possible volume syringe is capable of holding, such as 100 mL, or with 10 mL of fluid. The interface 7 may notify user that the auto refill is taking place but because the user has preprogrammed the auto refill option the contrast syringe will be filled automatically. An advantage to the auto refill feature is to save the user time between injections and provide the user with the ability quickly do additional injections that may not have been planned at end of the procedure if needed. Also, if user is performing multiple large volume injections the auto refill option pervades user with ability to continue performing such injections without stopping the case to manually fill syringes. Another advantage of the auto refill option is to provide the ability to continue performing injections once the desired volume in syringe has been met.

To set the auto refill option the interface may first check auto refill 625 has been selected by user. If user does intend to use auto refill option, the interface may prompt system to determine if syringe is filled enough to perform the intended operation 627. If so, the procedure may continue 629 and there is no need for refill. If not, the interface may prompt system to confirm auto refill has been enabled 631. If auto fill has not been enabled the interface may notify user 633. If auto fill has been enabled the system may determine which syringe is not full 635. If contrast is not full 637 the system may be prompted to fill contrast syringe from contrast source 643 until proper volume has been reached. If saline is not full 639 the system may be prompted to fill saline syringe from saline source 641. The interface may then prompt user to determine if user wants to abort auto fill 645, if so the system will stop filing syringe 647, if not system will continue to fill syringes from source until complete 649.

Figure 48:
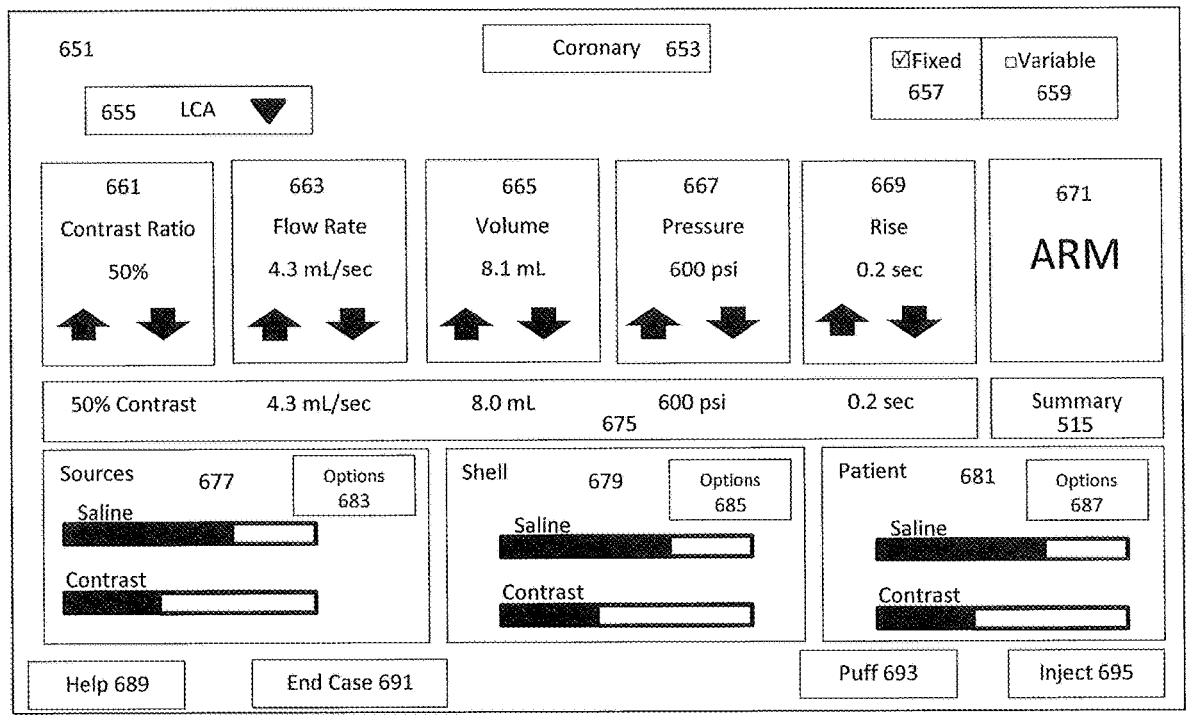
FIG. 48 is an illustration of a Dashboard Screen of the display of the system of FIG. 2.

After the injection system has been set up, primed, case selected, and the user is ready to begin the procedure, the user interface will transition to a dashboard screen 651 as shown in FIG. 48. The parameters on the dashboard screen 651 may be preset depending on the type of procedure user selects 609 during injection setup (as seen in flowchart of FIG. 46). The dashboard screen 651 provides user with the option to change all of the injection parameters previously described above and additional parameters including, but not limited to, fixed 657 or variable 659 injection speeds, the type of procedure 655, the contrast ratio 661, the flow rate 663, the volume 665, the pressure 667, the rise time 669, source options 683, shell options 685, patient options 687, summary 515, help 689, puff injection 693, end case 691, or arm 671 the system for injection. The dashboard screen 652 may also provide a parameter summary box 675 that provides user with clarification on the currently set injection parameters.

Advantages of the dashboard screen 651 include providing the user with the ability to easily and quickly modify various preset parameters of the injection that were populated based on type of case selected, determine if the system is armed or disarmed, and visually see what the current volume status is of each syringe and/or source. The dashboard screen 651 may include the type of case, for example if user selected a cardiac case and specifically a coronary procedure then the case type 653 may be depicted as a coronary procedure. Also included may be a specific case type tab 655 indicating the type of case about to be performed, for example if user is going to perform a left coronary artery injection. User may have the option to perform either fixed 657 or variable 659 speed injections. The dashboard screen 651 may provide user with visualization and accessibility to control various injection parameters, including but not limited to, contrast ratio 661, flow rate 663, volume 665, pressure 667, and rise time 669. Each injection parameter may include arrows or other markers indicating the user's ability to easily change the preset or previously set parameter. For example, if the preset parameter for a coronary procedure of contrast ratio is 50% contrast and 50% saline, but a patient is susceptible to complications arising from excess contrast, such as contrast included nephropathy (CIN) as described above, the user may decide to change the contrast ratio 661 to 20% contrast and 80% saline thereby decreasing amount of contrast needed during the injection but enough contrast to still provide a clear medical image. To accomplish this change the user may press the arrows or markers contained within the contrast ratio 661 tab and interface may prompt user with a pop-up window that will allow user to change the contrast to saline ration from 50/50 to the desired ratio. The injection system is capable of injecting 100% contrast and 0% saline, 100% saline and 0% contrast, or any other conceivable ratio of contrast and saline therebetween. The dashboard screen 651 may include a tab detailing the sources 667 and options 683 to change the source ranges, shell 679 and options 685 to change the shell ranges, and patient 681 and options to change the patient ranges, as described in more detail below and seen in FIG. 50-52. Dashboard screen 651 may also include a help tab 689, an end case tab 691, a puff tab 693, and an inject tab 695. The system provides for a hand controller, as previously described above, to control puff and fluid injections, however the user may also use the puff tab 693 or inject tab 695 in place of the hand controller. The dashboard may also include an arm tab 671 that the user may press once the injection parameters have been properly set and the system is now ready to start the procedure.

Figure 49:
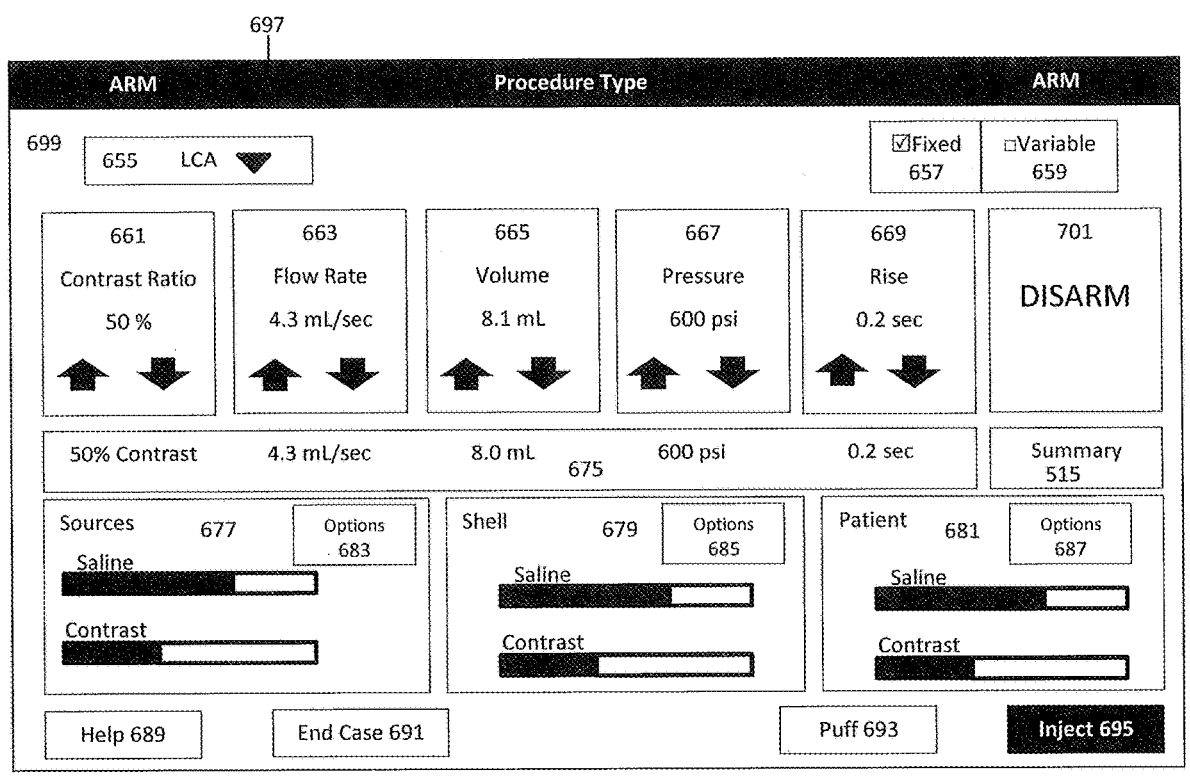
FIG. 49 is an illustration of an Armed Dashboard Screen of the display of the system of FIG. 2.

Referring now to FIG. 49, upon arming the system the interface may change to an armed dashboard screen 699. The armed dashboard screen 699 may have many of the same features and tabs as the previously described unarmed dashboard screen 651; however the armed screen 699 may include a notification bar 697 upon the top portion of the screen. The notification bar 697 and inject button 695 may be highlighted, blinking, flashing, include flashing text or visual indications, or otherwise indicate the system has been armed and is ready for injection. The armed dashboard screen 669 may also include a disarm tab 701 when selected would cause interface to switch back to the unarmed dashboard screen 651 of FIG. 48.

Referring now to FIG. 50-FIG. 52, the interface allows user to change various aspects of the shell option screen 685, source option screen 683, and patient option screen 687. The shell option screen 685 may include an information tab 703 indicating how long ago the current shell of the multiple-use subassembly was installed or the number of cases the shell has performed. For example, if each shell is intended to be used for either up to 100 hours or a total of 5 patient cases, the information tab 703 may be changed or customized to indicate the appropriate indicator. The shell of the multi-use subassembly may include a limit on number of uses, for example up to five patients, or limit on total usage time, for example up to 12 hours. The limit on shell usage may be preset from the manufacturer or changed by the user. Other shell options include changing the saline vent 705, purge 707, or fill 709 parameters, and changing the contrast vent 711, purge 713, or fill 715 parameters. The saline vent 705, contrast vent 711, include retracting the plunger in the saline or contrast syringe to various positions in order to vent each syringe of air, as described in more detail above and seen in FIG. 19. The purge 707, 713 options may flush system with fluid to remove any trapped air in-line and fill lines with desired fluid. The fill 709, 715 options includes filling either the contrast syringe or saline syringe with fluid from the fluid source. Shell option screen 685 may also allow user to change the status of the auto refill option 719, which was previously discussed, or indicate to the system that the shell is to be removed 721. Source option screen 683 provide user with ability to edit parameters 723 of saline source or edit parameters 725 of the contrast source, such as the volume of new contrast or saline source, or indicate sources need to be replaced 727. Patient option screen 687 allows user to change parameters for amount of maximum saline volume 729 or maximum contrast volume 731 the system can inject into the patient.

Figure 53:
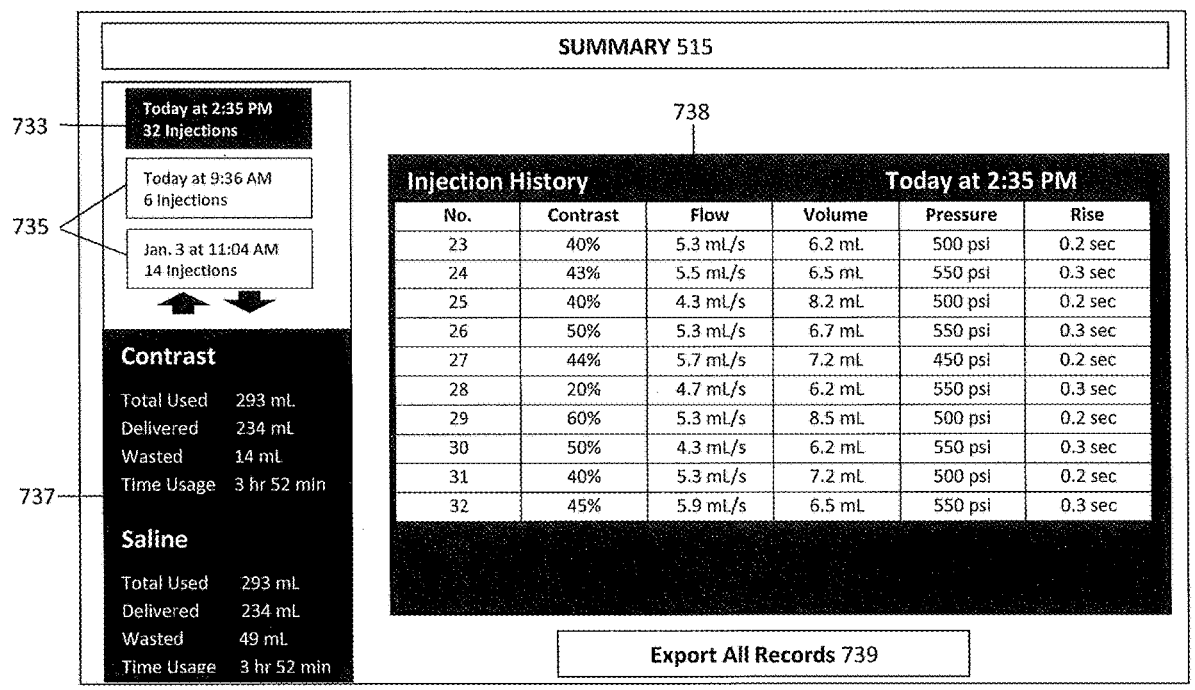
FIG. 53 is an illustration of a Summary Screen of the display of the system of FIG. 2.

Referring now to FIG. 53, one embodiment of the summary screen 515 is shown. The summary screen 515 may include a current injection summary 733, past injections summary 735, fluid summary 737 and an injection history 738. The current injection summary 733 may include time/date and number of injections for the current case, the past injection summary 735 may include time/date and number of injections for previous cases. The fluid summary 737 may include details about the saline and contrast for either the current injection summary 733 or past injection summary 735; such details may include as total amount of fluid used, total amount of fluid delivered to patient, total amount of fluid wasted (i.e., not delivered to patient but still used), and total usage time. The injection history 738 may include a table or chart depicting the injection parameters compared with what the injection system actually performed, the table may be sortable and include, but is not limited to, the number of injection performed, ratio of contrast, flow, volume, date of injection, time of injection, name of procedure type, patient characteristics, and pressure and rise time for each injection. The injection history 739 may also be exported 739 to any computer readable format or mobile application. The summary screen 515 may be access from the setup screen 509, the dashboard screen 651, or the armed dashboard screen 699.

Figure 54:
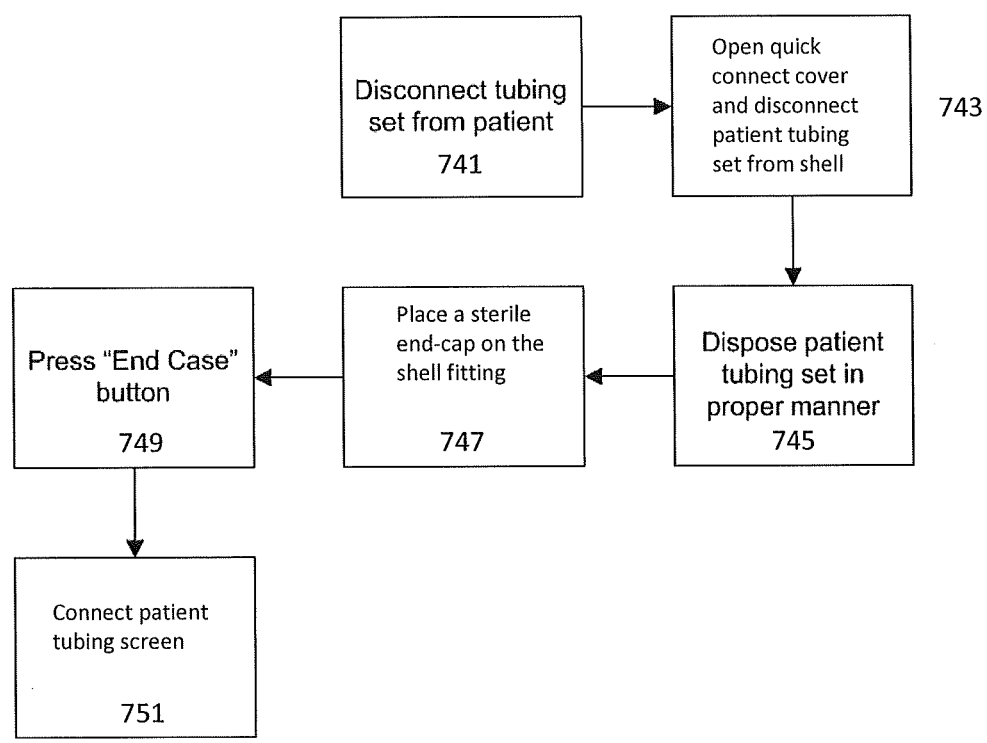
FIG. 54 is a diagrammatic flow chart illustrating the process to remove the multiple-use subassembly of the system of FIG. 2.

Referring now to FIG. 54, after the case is complete the user may select to end case 691 from either dashboard 651 or armed dashboard 699 screen. After case has been ended the interface 7 will then the user through the sequence of post procedure steps, in which in which the interface 7 may guide the user to first disconnect the tubing set from the patient 741. Next, open quick connect cover and disconnect patient tubing set from shell 743, dispose patient tubing set in proper manner 745, place a sterile end-cap on the shell fitting 747, press end case button 691 (as seen in FIG. 48-49) 749, and switch to connect patient tubing screen 751 to prepare for next case. Alternatively, if injection system is intended for single patient use only the sequence to end case 691 may include removal of the patient tubing and multi-use subassembly. Additionally, the interface 7 may notify user that after a certain number of patient uses, injections or total usage time the multi-use subassembly needs to be replaced.

Figure 55:
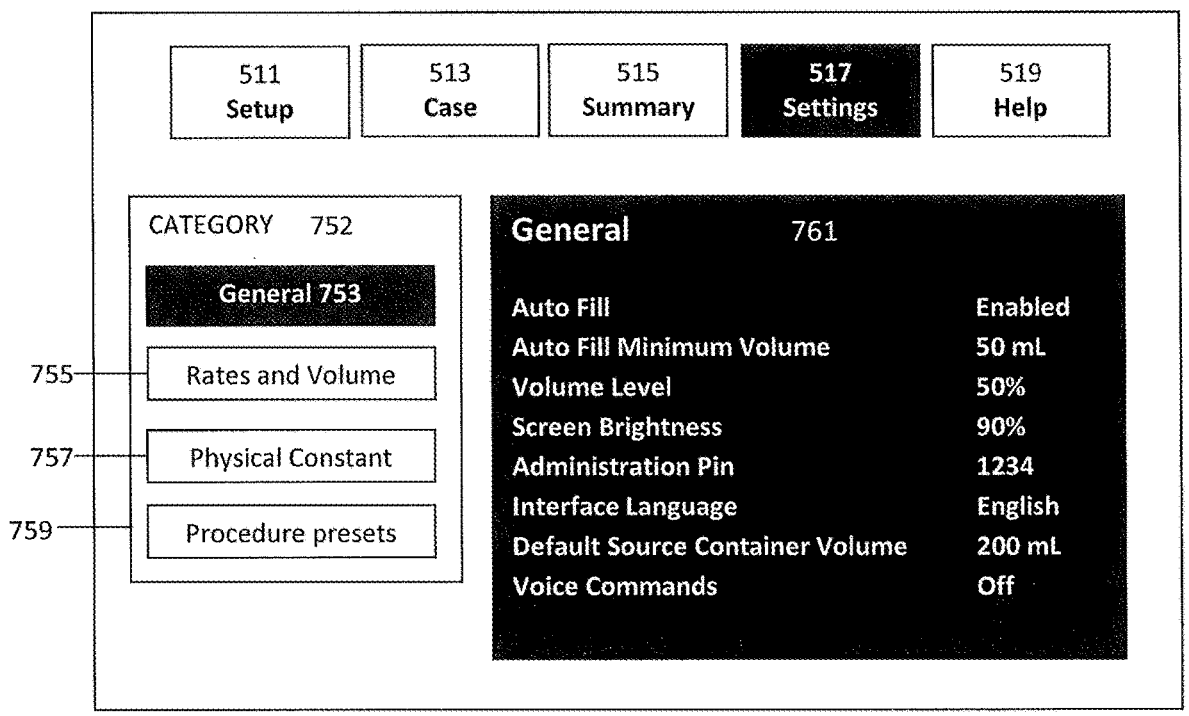
FIG. 55 is an illustration of a Settings Screen of the display of the system of FIG. 2.

Referring now to FIG. 55, the setting screen 517 is shown having a category tab 752 and a detailed information tab 761. The purpose of the setting screen 517 is to provide user with access to the current injector setting information and the ability to modify the settings. Possible system settings that may be modified through setting screen 517 may include auto fill status, minimum auto fill volumes, volume level, and system interface settings such as screen brightness, voice command, and default language. The setting screen 517 may have a category tab 752 which may include a general information selection tab 753 (which when selected prompts the generation information tab 761 as shown); a rates and volume tab 755, a physical content tab 757, and a procedure preset tab 759. Additionally, setting screen 517 options may be password protected to prevent unintended changes to presets. For example, system may prevent selected users from changing settings including, but not limited to, fill rate, priming volumes, procedure types, preset injection parameters for individual physicians, or any other preset injection parameter.

Figure 56:
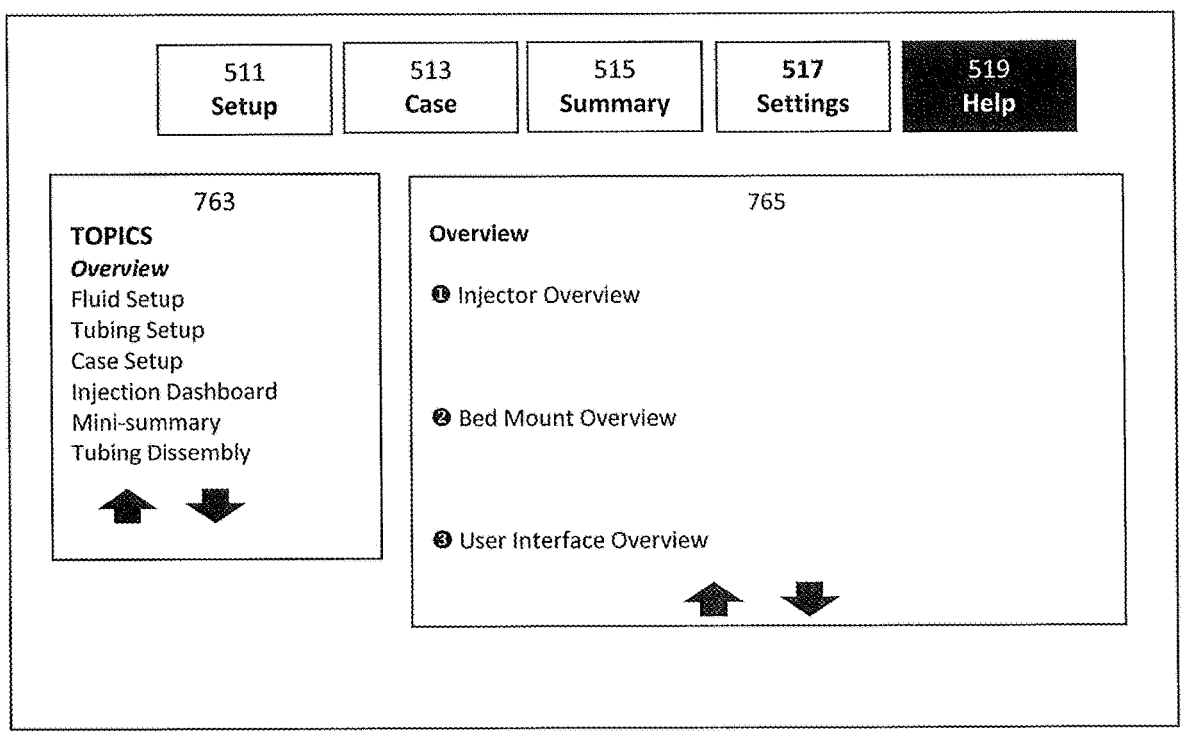
FIG. 56 is an illustration of a Help Screen of the display of the system of FIG. 2.

Referring now to FIG. 56, the help screen 518 is shown having a topics tab 763 and a detailed information tab 765. The topics tab 763 may include various topics or aspects of the injector that user may need help with. The detailed information tab 765 may contain a user manual, or other helpful hints, tips and help information to walk user through general issues or troubleshooting topics. Detailed information may include videos, audio step-by-step instructions, or live user support.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

It will be apparent to those skilled in the art that various modifications and variations can be made in the structure and methodology of the present invention. Thus, it is intended that the present invention cover such modifications and variations provided that they come within the scope of the appended claims and their equivalents.

The invention claimed is:

1. A method to provide injection system parameters for injecting a fluid into a patient, comprising:
    placing a multi-use subassembly into an injector housing, the multi-use subassembly comprising a first fluid barrel and a second fluid barrel, a first valve and a second valve, the injector housing comprising a first valve actuator and a second valve actuator;
    selecting on a first screen of a user interface a contrast-to-saline ratio of the fluid to be injected by adjusting a percentage of the contrast contained within the fluid and adjusting a percentage of the saline contained within the fluid so that the fluid to be injected is a mixture of both contrast and saline, the first valve actuator moves the first valve to a first valve fill position to fill the first fluid barrel with saline and the second valve actuator moves the second valve to a second valve fill position to fill the second fluid barrel with contrast in order to obtain the selected contrast-to-saline ratio of the fluid to be injected;
    displaying a second screen of the user interface which is different from the first screen, the second screen having an option to inject the fluid into the patient, selection of the inject option resulting in the first valve actuator to move the first valve to a first inject position and the second valve actuator to move the second valve to a second inject position in order to inject the fluid.

2. The method of claim 1, further comprising notifying a user with a visual notification after receiving the user selection.

3. The method of claim 2, wherein the visual indication comprises either a disposable sub-assembly has been properly installed, the injection system has been armed, the injection system is performing an injection, or the injection system has been disarmed.

4. The method of claim 1, wherein the user interface further comprises a display unit that is attached to the injection system or a bed rail.

5. The method of claim 4, wherein the display unit is attached to the bed rail or injector system by a movable arm.

6. The method of claim 5, further comprising the steps of:
    pulling the moveable arm closer to the user; and
    folding the movable arm.

7. The method of claim 1, further comprising displaying on the first screen of the user interface a plurality of selectable options for controlling the injection system.

8. The method of claim 7, wherein the user selection for one of the selectable options further comprises a volume option, pressure option, and a rise time option.

9. The method of claim 7, wherein the user selection for one of the selectable options further comprises a cardiac procedure option, a peripheral procedure option, or a physician list option.

10. The method of claim 9, wherein changing a system parameter or setting includes a preset injection parameter being populated.

11. The method of claim 7, wherein the plurality of selectable options for controlling the injection system comprises the contrast-to-saline ratio and at least one of the following: flow rate, volume, pressure, or rise time.

* * * * *